(12) United States Patent
Zhou et al.

(10) Patent No.: US 10,072,022 B2
(45) Date of Patent: Sep. 11, 2018

(54) ORIDONIN ANALOGS, COMPOSITIONS, AND METHODS RELATED THERETO

(71) Applicant: THE BOARD OF REGENTS OF THE UNIVERSITY OF TEXAS SYSTEM, Austin, TX (US)

(72) Inventors: Jia Zhou, League City, TX (US); Chunyong Ding, Galveston, TX (US); Qiang Shen, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/635,454

(22) Filed: Jun. 28, 2017

(65) Prior Publication Data
US 2017/0313716 A1  Nov. 2, 2017

Related U.S. Application Data

(60) Division of application No. 14/875,428, filed on Oct. 5, 2015, now Pat. No. 9,725,460, which is a continuation-in-part of application No. PCT/US2014/033111, filed on Apr. 5, 2014.

(60) Provisional application No. 61/808,753, filed on Apr. 5, 2013.

(51) Int. Cl.
*C07D 493/18* (2006.01)
*C07D 491/08* (2006.01)
*C07D 311/78* (2006.01)
*C07D 405/04* (2006.01)
*C07D 493/08* (2006.01)
*C07D 498/08* (2006.01)
*C07D 513/08* (2006.01)
*C07D 515/08* (2006.01)

(52) U.S. Cl.
CPC .......... *C07D 493/18* (2013.01); *C07D 311/78* (2013.01); *C07D 405/04* (2013.01); *C07D 491/08* (2013.01); *C07D 493/08* (2013.01); *C07D 498/08* (2013.01); *C07D 513/08* (2013.01); *C07D 515/08* (2013.01)

(58) Field of Classification Search
CPC .. C07D 493/18; C07D 311/78; C07D 405/04; C07D 515/08; C07D 491/08; C07D 498/08; C07D 513/08; C07D 493/08
See application file for complete search history.

(56) References Cited

U.S. PATENT DOCUMENTS

| | | | |
|---|---|---|---|
| 2003/0035851 A1 | 2/2003 | Chen | 424/728 |
| 2006/0052438 A1 | 3/2006 | Ho et al. | 514/453 |
| 2010/0228014 A1 | 9/2010 | Liu et al. | 536/18.1 |

FOREIGN PATENT DOCUMENTS

| | | |
|---|---|---|
| CN | 1255502 A | 6/2000 |
| CN | 101525338 A | 9/2009 |
| CN | 101723951 A | 6/2010 |
| WO | WO 2014/047780 | 4/2014 |
| WO | WO/14/165841 | 10/2014 |

OTHER PUBLICATIONS

Li, C., "Oridonin: An active diterpenoid targeting cell cycle arrest, apoptotic and autophagic pathways for cancer therapeutics." The international journal of biochemistry & cell biology 43.5 (2011): 701-704.*
Abelson, "Medicine from plants", *Science*, 247: 513, 1990.
Bogdanowicz-Szwed and Palasz, "Hetero-Diels-Alder Reaction of 3-Aryl-2-benzoyl-2-propenenitriles with Enol Ethers. Synthesis of 2-Alkoxy-3, 4-dihydro-2H-pyran-5-carbonitriles", *Monatsh. Chem.*, 128: 1157-72, 1997.
Bohanon et al. "Enhanced anti-fibrogenic effects of novel oridonin derivative CYD0692 in hepatic stellate cells" Mol Cell Biochem, 2015 J Surg Res, 199(2):441-9. (2015).
Cousins et al. "Effects of lanthanide complexes on the facial reactivity of 2-(2',3',4',6'-tetra-O-acetyl-β-D-glucopyranosyloxy) benzaldehyde in hetero-Diels-Alder reactions and a model to account for such effects", *Chem. Commun.*, 2171-72, 1997.
Ding et al. "Novel Nitrogen-Enriched Oridonin Analogues with Thiazole-Fused A-Ring: Protecting Group-Free Synthesis, Enhanced Anticancer Profile, and Improved Aqueous Solubility" *J. Med. Chem.* 56: 5048-5058, 2013.
Ding et al. "Oridonin Ring A-Based Diverse Constructions of Enone Functionality: Identification of Novel Dienone Analogues Effective for Highly Aggressive Breast Cancer by Inducing Apoptosis" *J. Med. Chem.*, 56: 8814-8825, 2013.
Ding et al. "Overcoming synthetic challenges of oridonin A-ring structural diversification: regio- and stereoselective installation of azides and 1,2,3-triazoles at the C-1, C-2, or C-3 position" *Organic Letters* 15(14):3718-3721, 2013.
Ding et al. "ent-Kaurane-based regio- and stereoselective inverse electron demand hetero-Diels-Alder reactions: synthesis of dihydropyran-fused diterpenoids", *Org Biomol Chem*, 12(42):8442-52, 2014.
Fujita et al., "The antitumor and antibacterial activity of the Isodon diterpenoids", *Chem. Pharm. Bull.*, 24(9):2118-27, 1976.
Gallier et al. "Hetero-Diels-Alder reactions of cyclic ketone derived enamide. A new and efficient concept for the asymmetric Robinson annulation", *Org. Lett.*, 11: 3060-63, 2009.
Gizecki et al. "First asymmetric synthesis of a 6-alkoxy-5,6-dihydro-1,3-oxazine: a promising enantioselective route to beta-amido aldehydes", *Org. Lett.*, 2: 585-88, 2000.
Han et al. "An asymmetric ent-kauranoid dimer from *Isodon rubescens* var. *lushanensis*" *Tetrahedron Letters*, 46: 5373-5375, 2005.
Han et al. "Novel ent-kaurane dimers from *Isodon rubescens* var. *rubescens*" *Tetrahedron Letters*, 45: 2833-2837, 2004.

(Continued)

*Primary Examiner* — John Matthew Mauro
(74) *Attorney, Agent, or Firm* — Norton Rose Fulbright US LLP

(57) ABSTRACT

Certain embodiments are directed to oridonin analogs or derivatives. In certain aspects, the derivatives are used as anticancer or anti-inflammatory agents.

8 Claims, 16 Drawing Sheets

(56) References Cited

OTHER PUBLICATIONS

Hong et al. "Dimeric ent-Kaurane Diterpenoids from Isodon excisus" *J. Nat. Prod.*, 74: 2382-2387, 2011.
Huang et al., "ent-Kaurane Diterpenoids from Isodon albopilosus", *J Nat. Prod.*, 68(12):1758-62, 2005.
Huang, SX et al. "Bisrubescensins A-C: Three New Dimeric ent-Kauranoids Isolated from Isodon rubescens" *Org. Lett.* 8(6): 1157-1160, 2006.
Huang, SX et al. Cytotoxic ent-kauranoid derivatives from Isodon rubescens, *Tetrahedron*, 62:4941-4947, 2006.
International Search Report and Written Opinion issued in PCT/US2014/033111, dated Aug. 29, 2014.
Johnson et al. "Facial selectivity in the cycloaddition of heterodienes to carbohydrate cyclic ketene acetals. A novel synthesis of disaccharide derivatives", *Chem. Commun.*, 1019-20, 1998.
Li et al. Synthesis and Biological Evaluation of Novel Furozan-Based Nitric Oxide-Releasing Derivatives of Oridonin as Potential Anti-Tumor Agents, *Molecules*, 17: 7556-7568, 2012.
Li et al. "Biomimetic syntheses of (−)-gochnatiolides A-C and (−)-ainsliadimer B", *J Am. Chem. Soc.*, 134: 12414-17, 2012.
Li et al. "A biomimetic total synthesis of (+)-ainsliadimer A", *Org. Lett.*, 12: 4284-87, 2010.
Li et al., "Cytotoxic ent-kaurene diterpenoids from Isodon phyllostachys", *Phytochemistry*, 13: 1336-40, 2006.
Li et al., "Oridonin: An active diterpenoid targeting cell cycle arrest, apoptotic and autophagic pathways for cancer therapeutics", *The International Journal of Biochemistry & Cell Biology.*, 43:701-04, 2011.
Messer et al. "Elaboration of D-(−)-ribose into a tricyclic, natural product-like scaffold", *J Org. Chem.*, 69: 8558-60, 2004.
Na et al., "A Novel Asymmetric ent-Kauranoid Dimer from Isodon enanderianus", *Chinese Journal of Chemistry.*, 20: 884-86, 2002.
Nagashima et al., "Novel cytotoxic kaurane-type diterpenoids from the New Zealand Liverwort *Jungermannia* species", *Tetrahedron*, 61:4531-44, 2005.
Newman, "Natural products as leads to potential drugs: an old process or the new hope for drug discovery?", *J Med. Chem.*, 51:2589-99, 2008.
Pellissier, "Asymmetric hetero-Diels-Alder reactions of carbonyl compounds", *Tetrahedron*, 65: 2839-77, 2009.
Shen et al., "Maoecrystal M: A Naturally Occurring Symmetric Ent-Kaurane Dimer from Rabdosia Eriocalyx", *Phytochemistry*, 35: 725-29, 1994.
Turov et al. "Features of the Reaction of Heterocyclic Analogs of 2'-Alkoxy-Chalcones with Lanthanide Shift Reagents", *Chemistry of Heterocyclic Compounds*, 40: 986-91, 2004.
Turov et al. "Conformational Mobility of Substituted 2-Methoxychalcones under the Action of Lanthanide Shift Reagents", *Russ. J Org. Chem.*, 41: 47-53, 2005.
Uroos and Hayes "Synthesis of the spirochroman core of dihypoestoxide and stereochemical proposal for the natural product", *Org. Lett.*, 12: 5294-97, 2010.
Wada et al. "(E)-2-Oxo-1-sulfonyl-3-alkenes as Reactive Hetero 1,3-Dienes. Absolutely endo-Selective Hetero Diels-Alder Reactions with Vinyl Ethers in the Presence of a Lewis Acid Catalyst", *Chem. Lett.*, 145-48, 1994.
Wada et al. "Exclusively endo-Selective Lewis Acid-Catalyzed Hetero Diels-Alder Reactions of (E)-1-Phenylsulfonyl-3-alken-2-ones with Vinyl Ethers", *Tetrahedron*, 5: 1205-20, 1996.
Xu et al., *Acta Pharmacologica Sinica*, 27(12):1642-46, 2006.
Xu et al., "Synthesis and biological evaluation of novel 1-O- and derivatives of oridonin as potential anticancer drug candidates", *Bioorg. Med.Chem. Lett.*, 18:4741-44, 2008.
Yin et al., "Study on the Constituents of Rabdosia rubescens Hemsl" *J Chin. Pharm. Univ.*, 34: 302-4, 2003. (English Abstract).
Zhang et al., *Chin. Pharm. J.*, 38:817-20, 2003. (English Translation).
Zhao et al. "ent-Kaurane Diterpenoids from Isodon pharicus" *J. Nat. Prod.*, 72: 988-993, 2009.
Zhou WS & Cheng YX, *Acta Chim. Sinica*, 48:1185-1190, 1990. (English Abstract).
Zhou et al., "Oridonin, a diterpenoid extracted from medicinal herbs, targets AML1-ETO fusion protein and shows potent antitumor activity with low adverse effects on t(8;21) leukemia in vitro and in vivo", *Blood*, 109:3441-50, 2007.
Chen, et al., "Targeting XBP1-mediated beta-catenin expression associate with bladder cancer with newly synthetic oridonin analogues." Oncotarget. 7(35): 56842-56854, 2016.
Ding, et al., "Discovery and development of natural product oridonin-inspired anticancer agents." European J Med Chem. 122:102-117, 2016.
Wu, et al., "A new oridonin analog suppresses triple-negative breast cancer cells and tumor growth via the induction of death receptor 5" Cancer Letters. 380:392-402, 2016.
Extended European Search Report in European Application No. 14778536.4 dated Nov. 8, 2016.
Fujita, et al., "Longikaurin A and B: new, biologically active diterpenoids from Rabdosia longituba" J Chem Society. 5:205-27, 1980.
First Office action in Chinese Application No. 201480031904.9 dated Nov. 11, 2016.
International Search Report and Written Opinion in International Application No. PCT/US2016/055468 dated Mar. 16, 2017.

* cited by examiner

ORIDONIN ANALOGS, COMPOSITIONS, AND METHODS RELATED THERETO

This application is a divisional from U.S. Ser. No. 14/875,428 filed Oct. 5, 2015, which is a continuation-in-part of International Application No. PCT/US2014/03311 filed Apr. 5, 2014, which claims priority to US 61/808,753 filed Apr. 5, 2013. Each of which is incorporated herein by reference in its entirety.

STATEMENT REGARDING FEDERALLY FUNDED RESEARCH

This invention was made with government support under P30 DA028821 awarded by the National Institute of Health. The government has certain rights in the invention.

BACKGROUND

Certain embodiments are directed to the fields of chemistry and oncology. Certain aspects are directed to anti-cancer and anti-inflammatory compounds.

Natural products have a profound impact upon both chemical biology and drug discovery, and the great structural diversity of natural products at various levels has always served medicinal chemists as a source of inspiration in their search for new molecular entities with pharmacological activity (Newman, *J. Med. Chem.* 2008, 51:2589-99). Natural tetracyclic diterpenoids, especially ent-kaurane diterpenoids with an enone system in ring D such as oridonin (1) and eriocalyxin B, constitute an important class of natural products which exhibit considerable pharmacological activities including anti-tumor and anti-inflammatory effects (Nagashima et al., *Tetrahedron* 2005, 61:4531-44; Huang et al., *J. Nat. Prod.* 2005, 12:1758-62; Li et al., *Phytochemistry* 2006, 13:1336-40).

Structurally, the highly oxygenated oridonin, belonging to 7,20-epoxy-ent-kaurane-type diterpenoid, is primarily characterized with an α,β-unsaturated ketone moiety in ring D and a 6-hydroxyl-7-hemiacetal group, which is stereochemically rich and densely functionalized. To date, reported structure modifications are primarily focused on the 1-O and 14-O positions, likely due to synthetic ease (Xu et al., *Bioorg. Med. Chem. Lett.* 2008, 18:4741-44). There remains a need for development of additional oridonin analogs.

SUMMARY

Oridonin is a natural product (isolated from the herb rabdosia rubescens) that is used in Chinese traditional medicine for its antitumor, antibacterial, antiviral, and anti-inflammatory effects. Certain embodiments are directed to oridonin analogs or derivatives. In certain aspects, the derivatives are used as anticancer or anti-inflammatory agents.

Certain embodiments are directed to compounds having the general formula of Formula Ia, Ib, Ic, or Id:

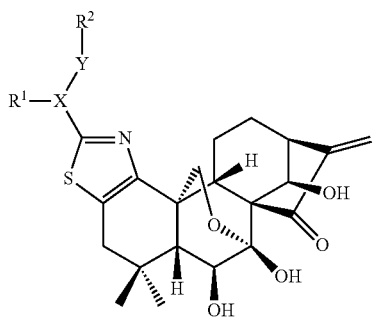
Formula Ia

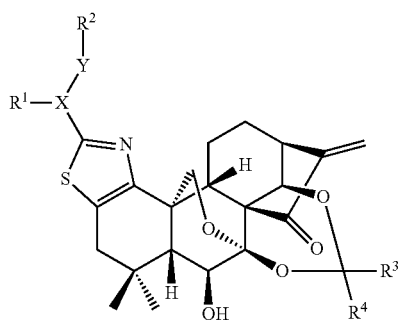
Formula Ib

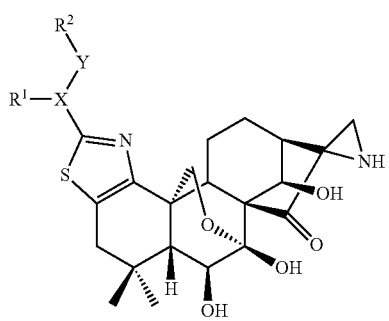
Formula Ic

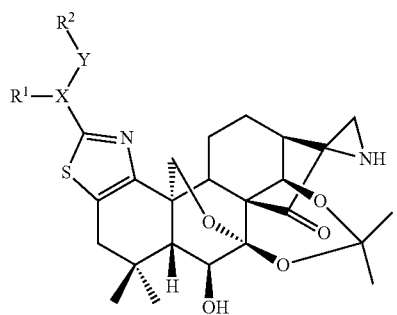
Formula Id where X is C or N; Y is $C_n$, and n is 0, 1, 2, 3, 4, or 5; and $R^1$ and $R^2$ are independently hydrogen, oxo, nitro, halo, mercapto, cyano, azido, amino, imino, azo, —C(NH)(NH$_2$), sulfonyl, sulfinyl, sulfo, thioyl, methyl, ethyl, C2-C6 alkyl, C1-C6 alkoxy, C1-C6 hydroxyalkyl, C1-C6 carboxylate, C1-C6 carboxyl, C3-C5 alkenyl, C2-C4 carbonyl, C2-C4 aldehyde, C2-C8 heteroalkyl, C1-C6 alkylsulfonyl, C1-C6 alkylhalide, substituted or unsubstituted 3 to 8 membered cycloalkyl, substituted or unsubstituted 3 to 8 membered heterocycle, substituted or unsubstituted aryl, substituted or unsubstituted heteroaryl. In certain aspects, $R^1$ and $R^2$ can optionally form a substituted or unsubstituted 3 to 8 membered heterocyle or 3 to 9 membered cycloalkyl.

$R^3$ and $R^4$ are independently hydrogen, hydroxy, methyl, ethyl, C3-C5 alkyl, C1-C5 hydroxyalkyl, a substituted or unsubstituted aryl, or a substituted or unsubstituted heteroaryl.

Certain aspects are directed to compounds of Formula Ia where X is N; n is 0, 1, or 2; and $R^1$ is hydrogen. In a further aspect $R^2$ is hydrogen, C1-C4 alkyl, C2-C4 aldehyde, C1-C4 alkynyl (wherein the double bond is at C1-C2, C2-C3, or C3-C4), —C(NH)(NH$_2$), or 3 to 7 membered cycloalkyl. In certain aspect $R^1$ and $R^2$ form a 4 to 6 member cycloalkyl or heterocyclyl.

In certain aspects X is C, n is 0, and $R^1$ is hydrogen and $R^2$ is hydrogen, C1-C4 alkyl.

In certain aspects a compound of Formula I is (6S,7S,7aR,10R,12bR,15R)-6,7,15-trihydroxy-2,5,5-trimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-19); (5aR,6S,7S,7aR,10S,12aS,12bR,15R)-2-amino-6,7,15-trihydroxy-5,5-dimethyl-9-methylene-5,5a,6,7,10, 11,12,12a-octahydro-4H-7,12b-(epoxymethano)-7a,10-methanocyclohepta[7,8]naphtho[1,2-d]thiazol-8(9H)-one(CYD-5-41); (5aR,6S ,7S,7aR,10S,12aS,12bR,15R)-6,7,15-trihydroxy-5,5-dimethyl-2-(methylamino)-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-5-54); (6S ,7S,7aR, 10R,12bR,15R)-2-(cyclohexylamino)-6,7,15-trihydroxy-5,5-dimethyl-9-methylene-5,5a, 6,7,10, 11,12,12a-octahydro-4H-7,12b-(epoxymethano)-7a,10-methanocyclohepta[7,8]naphtho[1,2-d]thiazol-8(9H)-one (CYD-6-17-2); (5aR,6S ,7S,7aR,10S,12aS,12bR,15R)-2-(allylamino)-6,7,15-trihydroxy-5,5-dimethyl-9-methylene-5,5a,6,7,10, 11,12,12a-octahydro-4H-7,12b-(epoxymethano)-7a,10-methanocyclohepta[7,8]naphtho[1,2-d]thiazol-8(9H)-one (CTD-6-18); (6S ,7S,7aR,10R,12bR,15R)-6,7,15-trihydroxy-5,5-dimethyl-9-methylene-2-((2-(piperidin-1-yl)ethyl)amino)-5,5a,6,7,10,11,12,12a-octahydro-4H-7,12b(epoxymethano)-7a,10-methanocyclohepta[7,8]naphtho[1,2-d]thiazol-8(9H)-one (CYD-6-20); N-((6S ,7S,7aR, 10R,12bR,15R)-6,7,15-trihydroxy-5,5-dimethyl-9-methylene-8-oxo-5,5a,6,7,8,9,10,11,12,12a-decahydro-4H,7,12b-(epoxymethano)-7a,10-methanocyclohepta[7,8]naphtho[1,2-d]thiazol-2-yl)acetamide (CYD-6-21); (6S ,7S,7aR,10R,12bR,15R)-2-(azepan-1-yl)-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-26-2); (5aR,6S ,7S,7aR,10S,12aS,12bR,15R)-2-(butyl amino)-6,7,15-trihydroxy-5,5-dimethyl-9-methylene-5,5a,6,7,10,11,12,12a-octahydro-4H,7,12b-(epoxymethano)-7a,10-methanocyclohepta[7,8]naphtho[1,2-d]thiazol-8(9H)-one (CYD-6-28); 1-((5aR,6S,7S,7aR,10S,12aS,12bR,15R)-6,7,15-trihydroxy-5,5-dimethyl-9-methylene-8-oxo-5,5a,6,7,8,9,10,11,12,12a-decahydro-4H-7,12b-(epoxymethano)-7a,10-methanocyclohepta[7,8]naphtho[1,2-d]thiazol-2-yl)guanidine (CYD-6-29); or (5aR,6S ,7S,7aR,10S,12aS,12bR,15R)-6,7,15-trihydroxy-2-(isopropylamino)-5,5-dimethyl-9-methylene-5,5a,6,7,10,11,12,12a-octahydro-4H-7,12b-(epoxymethano)-7a,10-methanocyclohepta[7 8]naphtho[1,2-d]thiazol-8(9H)-one (CYD-6-30).

Certain aspects are directed to compounds of Formulas Ic or Id where X is N; Y is C$_n$, and n is 0, 1, 2, 3, or 4; $R^1$ is hydrogen; and $R^2$ is hydrogen, methyl, C2 alkenyl, or C6 cycloalkyl.

Certain embodiments are directed to compounds having the general formula of Formula IIa or IIb or IIc or IId or IIe or IIf or IIg or IIh or IIi or IIj:

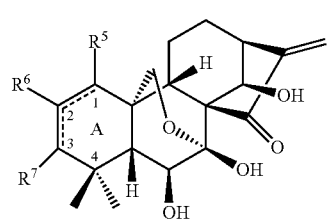

Formula IIa

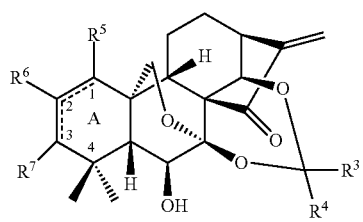

Formula IIb

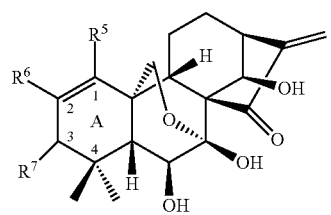

Formula IIc

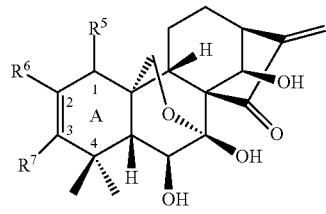

Formula IId

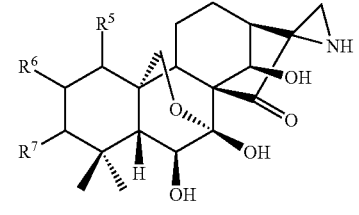

Formula IIe

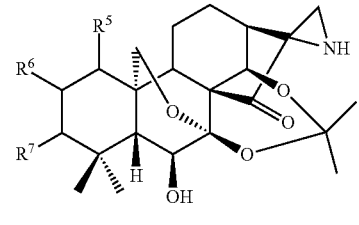

Formula IIf

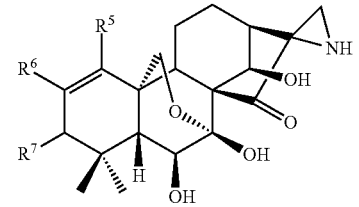

Formula IIg

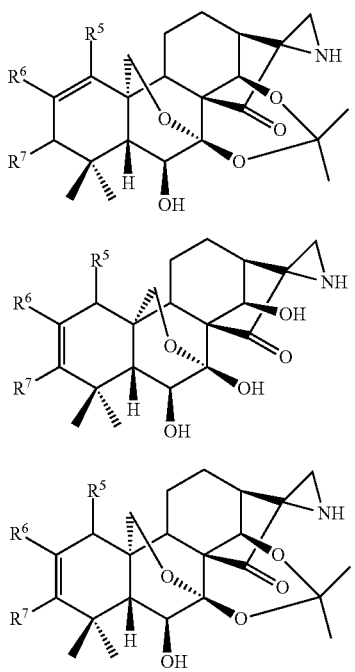

where R⁵, R⁶, and R⁷ are independently hydrogen, oxo, nitro, halo, mercapto, cyano, azido, amino, imino, azo, sulfonyl, sulfinyl, sulfo, thioyl, methyl, ethyl, hydroxyl, $NR^8R^9$, C1-C6 carboxyl, C1-C6 hydroxyalkyl, C1-C6 aldehyde, C2-C6 ketone, C1-C6 ester, C1-C6 alkyl, C1-C6 heteroalkyl, C1-C6 alkoxy, C1-C6 alkenyl; C1-C6 alkylsulfonyl, substituted or unsubstituted 3 to 6 membered cycloalkyl, substituted or unsubstituted 3 to 6 membered heterocyclyl, substituted or unsubstituted membered aryl, substituted or unsubstituted membered heteroaryl, substituted or unsubstituted triazole, substituted or unsubstituted 3 to 6 membered spiro-cycloalkyl, or substituted or unsubstituted 3 to 6 membered spiro-heterocycle; and R⁸ and R⁹ are independently hydrogen, oxo, nitro, halo, mercapto, cyano, azido, amino, imino, azo, sulfonyl, sulfinyl, sulfo, thioyl, methyl, ethyl, hydroxyl, C1-C6 carboxyl, C1-C6 hydroxyalkyl, C1-C6 aldehyde, C2-C6 ketone, C1-C6 ester, C1-C6 alkyl, C1-C6 heteroalkyl, C1-C6 alkoxy, C1-C6 alkenyl, C1-C6 alkylsulfonyl, substituted or unsubstituted 3 to 8 membered cycloalkyl, substituted or unsubstituted 3 to 8 membered heterocyclyl, substituted or unsubstituted aryl, substituted or unsubstituted heteroaryl, substituted or unsubstituted triazole, substituted or unsubstituted 3 to 6 membered spiro-cycloalkyl, or substituted or unsubstituted 3 to 6 membered spiro-heterocycle. In certain aspects the A ring is saturated, has a double bond between positions 1 and 2, or has a double bond between positions 2 and 3. In certain aspects R³ and R⁴ are as described above for Formula Ib.

In certain aspects the compound having R⁶ and R⁷ as hydrogen when R⁵ is oxo can be specifically excluded from compounds of Formula IIa, Formula IIb, and Formula IId.

In certain aspects one or more of R⁵, R⁶, or R⁷ is oxo. In certain aspects R⁵, R⁶, or R⁷ are nitro, cyano, azido, amino, imino, azo, $NR^8R^9$, substituted or unsubstituted triazole, substituted or unsubstituted 3 to 8 membered N containing heterocycle, or substituted or unsubstituted 3 to 8 membered N containing heteroaryl, wherein R⁸ and R⁹ are independently hydrogen or C1-C4 alkyl. In a further aspect a substituted triazole has an aryl or heteroaryl substituent. In certain aspects R⁵, R⁶, or R⁷ is substituted or unsubstituted spiro-tetrahydrofuran or spiro-furan. In a further embodiment the tetrahydrofuran or furan comprises a C1-C3 alkoxy substituent. In certain aspects the A ring is saturated, or has a double bond between positions 1 and 2, or has a double bond between positions 2 and 3.

In certain aspects R⁵ and R⁶ of Formula IIc are as described for Formula IIa with the exception that they cannot be substituted or unsubstituted spiro-cycloalkyl, or substituted or unsubstituted spiro-heterocycle. R⁷, R⁸, and R⁹ are as described for Formula IIa.

In certain aspects R⁶ and R⁷ of Formula IId are as described for Formula IIa with the exception that R⁶ and R⁷ cannot be substituted or unsubstituted spiro-cycloalkyl, or substituted or unsubstituted spiro-heterocycle.

In certain aspects a compound of Formula II is (3S,3aR, 3a¹R,6aR,7S,7aR,11aR,11bS)-7-hydroxy-5,5,8,8-tetramethyl-15-methylene-2,3,3a,7,7a,8,9,11b-octahydro-1H-6a,11a-(epoxymethano)-3,3a¹-ethanophenanthro[1,10-de][1,3]dioxin-14-one (CYD-6-75); (4aR,5S,6S,6aR,9S, 11aS,11bR,14R)-5,6,14-trihydroxy-4,4-dimethyl-8-methylene-4,4a,5,6,9,10,11,11a-octahydro-3H-6,11b-(epoxymethano)-6a,9-methanocyclohepta[α]naphthalen-7(8H)-one (CYD-6-82); (3S,3aR,3a¹R,6aR,7S,7aS,9S,11aR,11bS)-7,9-dihydroxy-5,5,8,8-tetramethyl-15-methylene-2,3,3a,7,7a,8,9,11b-octahydro-1H-6a,11a-(epoxymethano)-3,3a¹-ethanophenanthro[1,10-de][1,3]dioxin-14-one (CYD-6-81); (3S,4aS,5S,6S,6aR,9S,11aS,11bR,14R)-3,5,6,14-tetrahydroxy-4,4-dimethyl-8-methylene-4,4a,5,6,9,10,11,11a-octahydro-3H-6,11b-(epoxymethano)-6a,9-methanocyclohepta[α]naphthalen-7(8H)-one (CYD-6-90); (3S,3aR,3a¹R,6aR,7S,7aS,11aR,11bS)-7-hydroxy-5,5,8,8-tetramethyl-15-methylene-3,3a,7,7a,8,11b-hexahydro-1H-6a,11a-(epoxymethano)-3,3a¹-ethanophenanthro[1,10-de][1,3]dioxine-9,14(2H)-dione (CYD-6-86); (4aS,5S,6S,6aR,9S, 11aS,11bR,14R)-5,6,14-trihydroxy-4,4-dimethyl-8-methylene-4,4a,5,6,9,10,11,11a-octahydro-3H-6,11b-(epoxymethano)-6a,9-methanocyclohepta[α]naphthalene-3,7(8H)-dione (CYD-6-93); (3S,3aR,3a¹R,6aR,7S,7aR, 11aS,11bS,Z)-10-((dimethylamino)methylene)-7-hydroxy-5,5,8,8-tetramethyl-15-methyleneoctahydro-1H-6a,11a-(epoxymethano)-3,3a¹-ethanophenanthro[1,10-de][1,3]dioxine-11,14(2H)-dione (CYD-6-77); (3S,3aR,3a¹R,6aR,7S,7aR,11aS,11bS,Z)-7-hydroxy-10-(hydroxymethylene)-5,5,8,8-tetramethyl-15-methyleneoctahydro-1H-6a,11a-(epoxymethano)-3,3a¹-ethanophenanthro[1,10-de][1,3]dioxine-11,14(2H)-dione (CYD-6-91); (3S,3aR,3a¹R,6aR,7S,7aR,11aS,11bS)-7-hydroxy-5,5,8,8-tetramethyl-15-methylene-11,14-dioxo-2,3,3a,7,7a,8,11,11b-octahydro-1H-6a,11a-(epoxymethano)-3,3a¹-ethanophenanthro[1,10-de][1,3]dioxine-10-carbaldehyde (CYD-6-92); (1aR,3aR,4S,5S,5aR,8S,10aS,10bS,10cS,13R)-4,5,13-trihydroxy-3,3-dimethyl-7-methylenedecahydro-1aH-5,10b-(epoxymethano)-5a,8-methanocyclohepta[7,8]naphtho[1,2-b]oxiren-6(2H)-one (CYD-7-23-1) and (1S,2S,4aR,5S,6S,6aR,9S,11aS,11bS,14R)-1,2,5,6,14-pentahydroxy-4,4-dimethyl-8-methylenedecahydro-1H-6,11b-(epoxymethano)-6a,9-methanocyclohepta[a]naphthalen-7(8H)-one (CYD-7-23-2); (3S,3aR,3a¹R,6aR,7S,7aR,10S,11S,11aS,11bS)-10-azido-7,11-dihydroxy-5,5,8,8-tetramethyl-15-methylenedecahydro-1H-6a,11a-(epoxymethano)-3,3a¹-ethanophenanthro[1,10-de][1,3]dioxin-14-one (CYD-7-42); or (3S,3aR,3a¹R,6aR,7S,7aR,10S,11S,11aS,11bS)-7,11-dihydroxy-5,5,8,8-tetramethyl-15-methylene-10-(4-phenyl-1H-1,2,3-triazol-1-yl)decahydro-1H-6a,11a-(epoxymethano)-3,3a¹-ethanophenanthro[1,10-de][1,3]dioxin-14-one (CYD-7-54).

Certain aspects are directed to compounds of Formula IIe or IIf or IIg or IIh or IIi, or IIj where $R^5$ is a hydrogen or hydroxyl or carbonyl; $R^6$ is hydrogen; and and $R^7$ is hydrogen or a carbonyl.

Certain embodiments are directed to compounds having the general formula of Formula IIIa or IIIb:

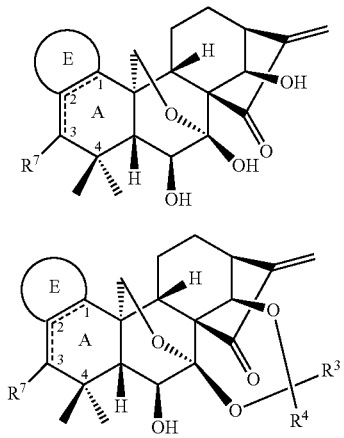

Formula IIIa

Formula IIIb where ring E is a substituted or unsubstituted 3 to 8 membered heterocycle having 1, 2, or 3 heteroatoms; substituted or unsubstituted 3 to 8 membered cycloalkyl; substituted or unsubstituted aryl; substituted or unsubstituted heteroaryl having 1, 2, or 3 heteroatoms; and $R^7$ is hydrogen, hydroxyl, oxo, nitro, halo, mercapto, cyano, azido, amino, imino, azo, sulfonate ester, sulfonyl, sulfinyl, sulfo, thioyl, methyl, ethyl, C3-C5 alkyl, C3-C5 alkenyl, C2-C4 ketone, substituted or unsubstituted 3 to 8 membered cycloalkyl, substituted or unsubstituted 3 to 8 membered heteroalkyl. In certain aspects ring A is saturated, or has a double bond between the 1 and 2 position or the 2 and 3 position. In certain aspects $R^7$ can optionally form a polycyclic moiety with ring E.

In certain aspects the E ring is a substituted or unsubstituted 3 to 8 membered heterocycle having 1, 2, or 3 heteroatoms. In other aspects the E ring is a substituted or unsubstituted heteroaryl having 1, 2, or 3 heteroatoms.

In a further aspect the E ring is substituted or unsubstituted aziridine, azirine, oxirane (epoxide), oxirene, thirane, thirene, azetidine, oxetane, thietane, azete, oxete, thiete, diazetidine, dioxetane, ditietane, pyrrolidine, pyrrole, tetrahydrofuran, furan, thiolane, thiophene, priperidine, pyridine, oxane, pyran, thiane, thiopuran, imidazole, imidazolidine, oxazolidine, oxazoledioxalane, triazole, oxadiazole, or thiodiazole. In certain aspects the E ring is an oxo substituted thiete.

In certain aspects $R^7$ is sulfonate ester. In a further aspect the sulfonate ester is bonded to the E ring forming a polycyclic moiety.

In certain aspects a compound of Formula III is (1aR,3aR,4S,4aR,4a¹R,7aR,8S,10aS,10bS,10cS)-4-hydroxy-3,3,6,6-tetramethyl-13-methylenedecahydro-1aH-4a,10b-(epoxymethano)-4a¹, 8-ethanooxireno[2',3':5,6]phenanthro[1,10-de][1,3]dioxin-14-one (CYD-7-9); (1aR,2R,3aR,4S,4aR,4a¹R,7aR,8S,10aS,10bS,10cS)-2,4-dihydroxy-3,3,6,6-tetramethyl-13-methylenedecahydro-1aH-4a,10b-(epoxymethano)-4a¹,8-ethanooxireno[2', 3': 5,6]phenanthro[1,10-de][1,3]dioxin-14-one (CYD-7-19); or (1aR,2R,3aR,4S,5S,5aR,8S,10aS,10bS,10cS,13R)-2,4,5,13-tetrahydroxy-3,3-dimethyl-7-methylenedecahydro-1aH-5,10b-(epoxymethano)-5a,8-methanocyclohepta[7,8]naphtho[1,2-b]oxiren-6(21/)-one (CYD-7-27).

Certain embodiments are directed to compounds having the general formula of Formula IVa or IVb:

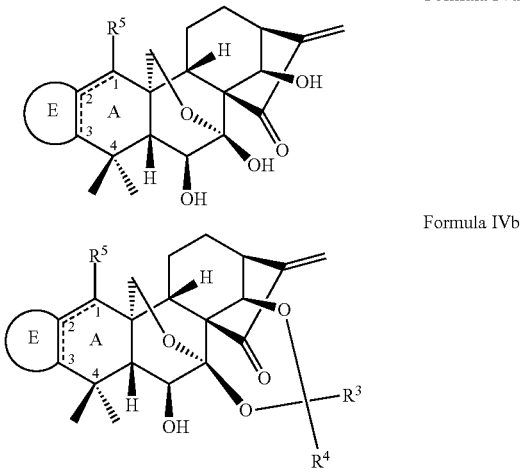

Formula IVa

Formula IVb where ring E is as described in Formula IIIa. $R^5$ is hydrogen, hydroxyl, oxo, nitro, halo, mercapto, cyano, azido, amino, imino, azo, sulfonate ester, sulfonyl, sulfinyl, sulfo, thioyl, methyl, ethyl, C3-C5 alkyl, C3-C5 alkenyl, C2-C4 ketone, substituted or unsubstituted 3 to 8 membered cycloalkyl, substituted or unsubstituted 3 to 8 membered heteroalkyl. Ring A has no double bonds, a double bond between the 1 and 2 position, or the 2 and 3 position. In certain aspects $R^5$ can optionally form a polycyclic moiety with ring E. In certain aspects $R^3$ and $R^4$ are as described for Formula Ib.

In a further aspect the E ring is substituted or unsubstituted aziridine, azirine, oxirane (epoxide), oxirene, thirane, thirene, azetidine, oxetane, thietane, azete, oxete, thiete, diazetidine, dioxetane, ditietane, pyrrolidine, pyrrole, tetrahydrofuran, furan, thiolane, thiophene, priperidine, pyridine, oxane, pyran, thiane, thiopuran, imidazole, imidazolidine, oxazolidine, oxazoledioxalane, triazole, oxadiazole, or thiodiazole. In certain aspects the E ring is an oxo substituted thiete.

Certain embodiments are directed to compounds having the general formula of Formula Va or Vb or Vc or Vd:

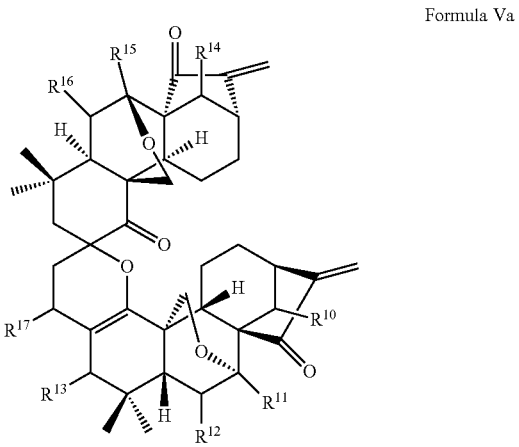

Formula Va

-continued

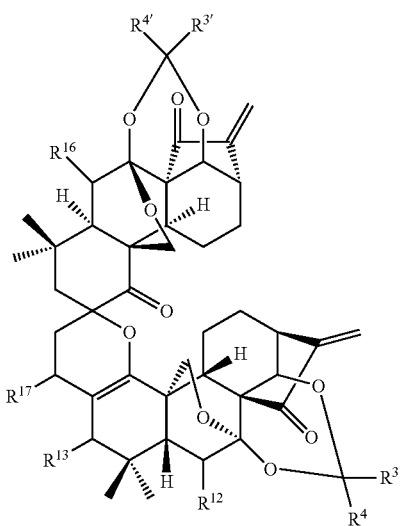

Formula Vb

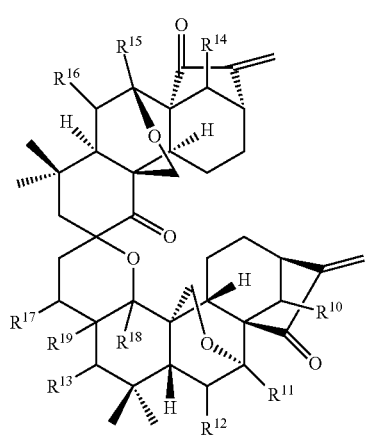

Formula Vc

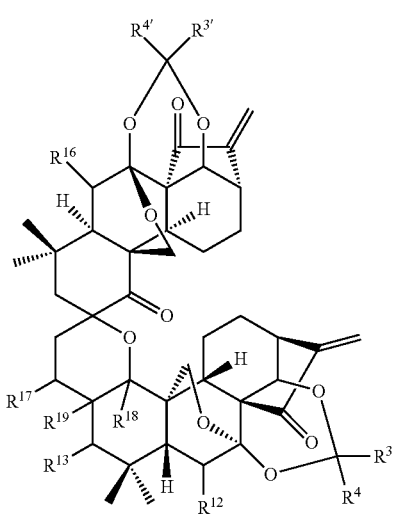

Formula Vd where $R^{10}$, $R^{11}$, $R^{12}$, $R^{13}$, $R^{14}$, $R^{15}$, $R^{16}$, $R^{17}$, $R^{18}$, and $R^{19}$ are independently hydrogen, oxo, nitro, halo, mercapto, cyano, azido, amino, imino, azo, sulfonyl, sulfinyl, sulfo, thioyl, methyl, ethyl, hydroxyl, C1-C6 carboxyl, C1-C6 alkyl, C1-C6 heteroalkyl, C1-C6 alkoxy, C1-C6 alkenyl, C1-C6 alkylsulfonyl, substituted or unsubstituted 3 to 8 membered cycloalkyl, or substituted or unsubstituted 3 to 8 membered heterocyclyl. $R^3$, $R^{3'}$, $R^4$ and $R^{4'}$ are as described for $R^3$ and $R^4$ in Formula Ib.

In certain aspects $R^{18}$ and $R^{19}$ can bridged by an oxygen to form an epoxide.

In certain aspects a compound of Formula V is (2R,4aR, 5S,6S,6aR,6a'R,7'S,8'S,8a'R,9S,11aS,11bS,11'S,13a'S, 13b'S,14R,16'R)-5,6,7', 8',14,16'-hexahydroxy-4,4,6',6'-tetramethyl-8,10'-dimethylene-4,4a,5,6,6',6a',7',8',9, 10,11, 11a,11',12',13'13a'- hexadecahydro-3'H-spiro[6,11b-(epoxymethano)-6a,9-methanocyclohepta[α]naphthalene-2, 2'-8,13b-(epoxymethano)-8a,11-methanocyclohepta[3,4] benzo[1,2-h]chromene]-1,7,9'(3H,4'H,5'H,8H,10'H)-trione (CYD-5-40-2), or (2R,4aR,4a'R,5'S,6aR,6'S,6a'R,7S,8S, 8aR,9'S,11S,11a'S,11b'S,13aS,13bS,13cR,14'R,17R)-5',6',7, 8,14',17-hexahydroxy-4',4',6,6-tetramethyl-8',10-dimethylenehexadecahydro-3H-spiro[4a,13c-epoxy-8,13b-(epoxymethano)-8a,11-methanocyclohepta[3,4]benzo[1,2-h]chromene-2,2'-6,11b-(epoxymethano)-6a,9-methanocyclohepta[α]naphthalene]-1',7',9(3'H,4H,5H,8'H, 10H)-trione (CYD-6-39).

Certain embodiments are directed to compounds having the general formula of Formula VIa or VIb:

Formula VIa

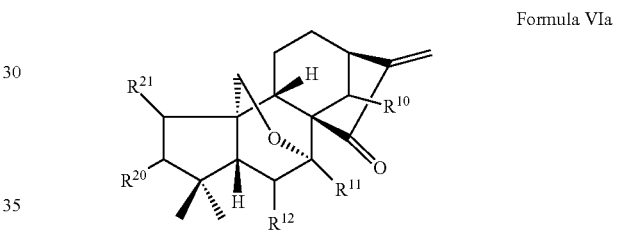

Formula VIb

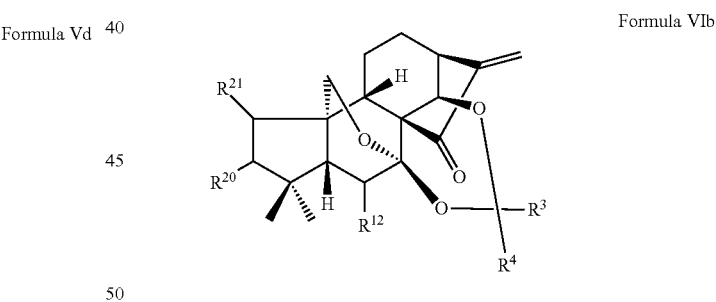

where $R^{10}$, $R^{11}$, $R^{12}$, $R^{20}$, and $R^{21}$ are independently hydrogen, oxo, nitro, halo, mercapto, cyano, azido, amino, imino, azo, carbamoyl, sulfonyl, sulfinyl, sulfo, thioyl, methyl, ethyl, hydroxyl, C1-C6 carboxyl, C1-C6 alkyl, C1-C6 heteroalkyl, C1-C6 alkoxy, C1-C6 alkenyl, C1-C6 alkylsulfonyl, substituted or unsubstituted 3 to 8 membered cycloalkyl, or substituted or unsubstituted 3 to 8 membered heterocyclyl. In certain aspects $R^{20}$ and $R^{21}$ can optionally form a substituted or unsubstituted 3 to 8 membered cycloalkyl, or substituted or unsubstituted 3 to 8 membered heterocyclyl. $R^3$ and $R^4$ are as described for Formula Ib.

Certain embodiments are directed to compounds having the general formula of Formula VIIa or VIIb:

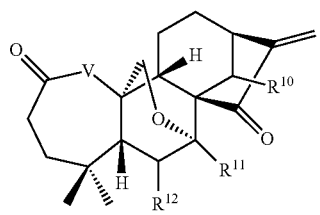

Formula VIIa

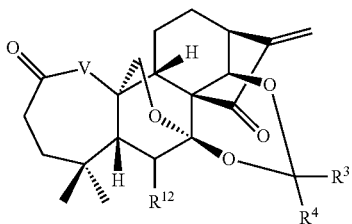

Formula VIIb where V is O or $NR^{22}$; $R^{10}$, $R^{11}$, and $R^{12}$ are as described in Formula VI; and $R^{22}$ is hydrogen, oxo, nitro, halo, mercapto, cyano, azido, amino, imino, azo, sulfonyl, sulfinyl, sulfo, thioyl, methyl, ethyl, hydroxyl, C1-C6 carboxyl, C1-C6 alkyl, C1-C6 heteroalkyl, C1-C6 alkoxy, C1-C6 alkenyl, C1-C6 alkylsulfonyl, substituted or unsubstituted 3 to 8 membered cycloalkyl, or substituted or unsubstituted 3 to 8 membered heterocyclyl. $R^3$ and $R^4$ are as described for Formula Ib.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

Throughout this application, the term "about" is used to indicate that a value includes the inherent variation of error for the device, the method being employed to determine the value, or the variation that exists among the study subjects.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living mammalian organism, such as a human, monkey, cow, sheep, goat, dogs, cat, mouse, rat, guinea pig, or species thereof. In certain embodiments, the patient or subject is a primate. Non-limiting examples of human subjects are adults, juveniles, infants and fetuses.

The use of the word "a" or "an" when used in conjunction with the term "comprising" in the claims and/or the specification may mean "one," but it is also consistent with the meaning of "one or more," "at least one," and "one or more than one."

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

I. Oridonin and Related Compounds

Figure 1:
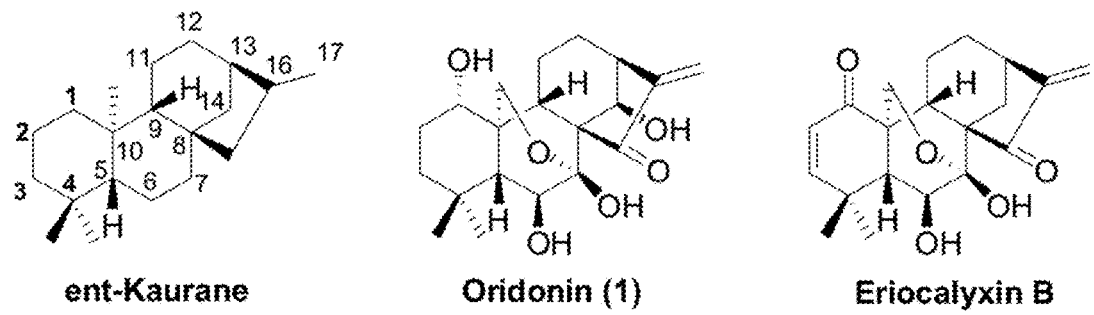
FIG. 1. Representative molecules of the tetracyclic diterpenes.

Oridonin, an ent-kaurane diterpenoid isolated from plants of genus *Isodon* (*Rabdosia*), has been widely used by the local people in China for the treatment of respiratory and gastrointestinal bacterial infections, inflammation, and various cancers for many years (Fujita et al., *Chem. Pharm. Bull.* 1976, 24(9):2118-27; Yin et al., *J. Chin. Pharm. Univ.* 2003, 34, 302-4). Of particular interest is its unique, safe anticancer pharmacological profile (Abelson, *Science* 1990, 247: 513-15). Increasing evidence has suggested that oridonin may improve the survival rates of cancer patients through hampering the progression of tumor, mitigating tumor burden, and alleviating cancer syndrome (Li et al., *The International Journal of Biochemistry & Cell Biology.* 2011, 43:701-04). For example, oridonin not only induced typical mitochondrial apoptosis in acute myeloid leukemic cells with an $IC_{50}$ value of 2 μM, but also exhibited substantial anti-leukemia activities with a low side-effect in murine models (15 mg/kg) (Zhou et al., *Blood* 2007, 109:3441-50). Oridonin was also demonstrated to inhibit tumor cell proliferation and induce cancer cell death by regulating a series of transcription factors, protein kinases as well as pro- and/or anti-apoptotic proteins (Li et al., *The International Journal of Biochemistry & Cell Biology.* 2011, 43:701-04; Zhang et al., *Chin. Pharm.* 1 2003, 38:817-20; Huang et al., *J. Nat. Prod.* 2005, 12:1758-62). However, its relatively moderate potency, limited aqueous solubility, and bioavailability hampered oridonin use in the clinic (Zhang et al., *Chin. Pharm.* 1 2003, 38:817-20; Xu et al., *Acta Pharmacologica Sinica* 2006, 27(12):1642-46).

Oridonin has elicited a great deal of interest due to its biological role, safe pharmacological profile, and its densely functionalized, stereochemistry-rich frameworks. The inventors have taken advantage of oridonin, a naturally abundant and large-scale commercially available ent-kaurane diterpenoid, as a basic template to construct a natural product-like compound library through diversity-oriented synthesis for identifying anti-cancer drugs. A compound library of novel oridonin analogs have been designed, synthesized and pharmacologically evaluated by following approaches including, but not limited to oridonin ring A-based diversity-oriented synthesis including enone functionalization, heteroaromatic cycle-fused construction, ring expansion and contraction, and diversity-oriented functionalization at C-14 position.

Oridonin analogs are described herein. The analogs described can be used for the treatment of human cancer and inflammation. A series of oridonin analogs have been synthesized and tested in breast, pancreatic, and prostate cancer cell lines. A number of the compounds are effective in suppressing cell growth. The molecules described herein may be used as preventive and therapeutic agents for various cancers including but not limited to breast cancers, pancreatic cancer, brain tumors, head/neck cancer, prostate and lung cancers, as well as inflammation.

A series of nitrogen-containing oridonin analogs with thiazole-fused ring A were prepared starting from oridonin through a protecting group-free synthetic strategy. Incorporating a substituted thiazole-fused moiety into oridonin not only enhanced the anticancer activity, but also significantly improved aqueous solubility. Most of these analogs such as compounds CYD-5-54, CYD-6-30, CYD-6-28, CYD-6-17-2, and CYD-6-18 have exhibited potent anti-proliferation effects against cancer cell lines, especially breast cancer cells including estrogen receptor (ER)-negative breast cancer cell MDA-MB-231, with low micromolar to nanomolar $IC_{50}$ values (Table 1).

TABLE 1a

Effects of oridonin analogues on proliferation of human breast, pancreatic cancer and prostate cancer cell lines.

| Compound | Structure | $IC_{50}$ (μM)[a] | | | | |
| --- | --- | --- | --- | --- | --- | --- |
| | | Breast cancer | | Pancreatic cancer | | Prostate cancer |
| | | MCF-7 | MDA-MB-231 | AsPC1 | Panc-1 | DU145 |
| Oridonin | 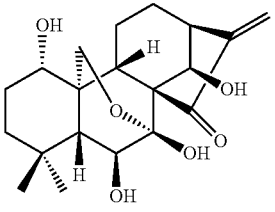 | 6.64 | 29.42 | 34.47 | 13.37 | 14.23 |
| CYD-6-19 | 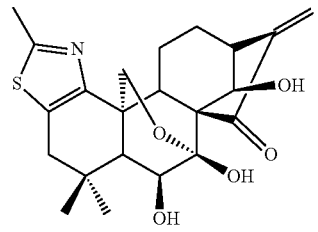 | 2.63 | 6.88 | 6.46 | 7.83 | 7.63 |

TABLE 1a-continued

Effects of oridonin analogues on proliferation of human breast, pancreatic cancer and prostate cancer cell lines.

| Compound | Structure | IC$_{50}$ (μM)$^a$ | | | | |
| --- | --- | --- | --- | --- | --- | --- |
| | | Breast cancer | | Pancreatic cancer | | Prostate cancer |
| | | MCF-7 | MDA-MB-231 | AsPC1 | Panc-1 | DU145 |
| CYD-5-41 | | 1.02 | 3.24 | 5.58 | 6.13 | 3.46 |
| CYD-5-54 | | 1.28 | 2.06 | 1.84 | 2.33 | 4.05 |
| CYD-6-30 | | 0.82 | 0.28 | 1.45 | 3.27 | 5.31 |
| CYD-6-28 | | 0.59 | 1.06 | 1.39 | 4.01 | 4.22 |

TABLE 1a-continued

Effects of oridonin analogues on proliferation of human breast, pancreatic cancer and prostate cancer cell lines.

| Compound | Structure | IC$_{50}$ (μM)$^a$ | | | | |
|---|---|---|---|---|---|---|
| | | Breast cancer | | Pancreatic cancer | | Prostate cancer |
| | | MCF-7 | MDA-MB-231 | AsPC1 | Panc-1 | DU145 |
| CYD-6-17-2 | | 0.94 | 0.83 | 1.65 | 3.74 | 1.82 |
| CYD-6-26-2 | | 1.15 | 6.82 | 2.30 | 6.29 | 4.74 |
| CYD-6-20 | | 1.00 | 1.83 | 1.10 | 1.54 | 1.16 |
| CYD-6-19 | | 0.18 | 0.18 | 1.05 | 1.1 | 1.18 |

TABLE 1a-continued

Effects of oridonin analogues on proliferation of human breast, pancreatic cancer and prostate cancer cell lines.

| | | IC$_{50}$ (μM)$^a$ | | | | |
|---|---|---|---|---|---|---|
| | | Breast cancer | | Pancreatic cancer | | Prostate cancer |
| Compound | Structure | MCF-7 | MDA-MB-231 | AsPC1 | Panc-1 | DU145 |
| CYD-6-21 | | 1.99 | 6.82 | 4.83 | 6.71 | 6.34 |
| CYD-6-29 | | 3.43 | >10$^b$ | >10 | 15.44 | 35.86 |

$^a$Breast cancer cell lines: MCF-7, MDA-MB-231. Pancreatic cancer cell lines: ASPC1, MiaPaCa-2 and Panc-1. Prostate cancer: DU145. Software: MasterPlex ReaderFit 2010, MiraiBio, Inc.
$^b$If a specific compound is given a value >10, indicates that a specific IC$_{50}$ cannot be calculated from the data points collected, meaning 'no effect'.

TABLE 1b

Antiproliferative effects of representative triazolesubstituted analogues against human breast cancer cell lines IC50 (μM)$^a$

| Compounds | MCF-7 | MDA-MB-231 |
|---|---|---|
| Oridonin | 6.6 | 29.4 |
| CYD-7-86 | 0.38 | 0.48 |
| CYD-7-90 | 2.1 | 1.8 |

TABLE 1b-continued

Antiproliferative effects of representative triazolesubstituted analogues against human breast cancer cell lines IC50 (μM)[a]

| Compounds | MCF-7 | MDA-MB-231 |
|---|---|---|
| CYD-7-82 | 2.3 | 1.8 |
| CYD-8-3 | 2.0 | 1.1 |
| CYD-8-5 | 1.9 | 3.5 |

[a]Breast cancer cell lines: MCF-7 and MDA-MB-231. Software: MasterPlex ReaderFit 2010, MiraiBioi, Inc. Values are mean ± SE of three independent experiments.

TABLE 1c

Antiproliferative Effects of Oridonin and the Dieone Analogues against Human Breast Cancer Cell Lines

| Compound | MCF-7 | MDA-MB-231 |
|---|---|---|
| Oridonin | 4.36 ± 1.41 | 28.0 ± 1.40 |
| CYD-6-25 | 0.56 ± 0.31 | 3.49 ± 1.21 |
| CYD-6-58 | 1.31 ± 0.25 | 2.23 ± 0.68 |
| CYD-6-92 | 1.28 ± 0.47 | 3.46 ± 1.33 |
| CYD-7-13 | 10.2 ± 3.07 | >30 |
| CYD-7-5 | >30 | >30 |

TABLE 1c-continued

Antiproliferative Effects of Oridonin and the Dieone Analogues against Human Breast Cancer Cell Lines

| Compound | MCF-7 | MDA-MB-231 |
|---|---|---|
| CYD-6-86 | 0.98 ± 0.19 | 5.6 ± 1.06 |
| CYD-6-93 | 3.48 ± 2.16 | 9.39 ± 0.48 |

[a]Breast cancer cell lines: MCF-7 and MDA-MB-231. Software: MasterPlex ReaderFit 2010, MiraiBio, Inc. Values are the mean ± SE of three independent experiments. If a specific compound is given a value >30, it indicates that a specific IC50 cannot be calculated from the data points collected, meaning "no effect".

TABLE 1d

Growth Inhibitory Effects of Oridonin and the Selected Dienone Analogues against Drug-Resistant Breast Cancer MCF-7/ADR Cells

| Compound | IC50 (μM)[a] |
|---|---|
| Oridonin | >30 |
| CYD-6-25 | 5.03 ± 1.91 |
| CYD-6-58 | 5.82 ± 2.12 |
| CYD-6-92 | 6.55 ± 0.96 |
| CYD-6-86 | 6.02 ± 1.28 |

[a]Breast cancer cell line: MCF-7.ADR. Software: MasterPlex ReaderFit 2010, MiraiBio, Inc. Values are the mean ± SE of three independent experiments. If a specific compound is given a value >30, it indicates that a specific IC50 cannot be calculated from the data points collected, meaning "no effect".

Figure 2:
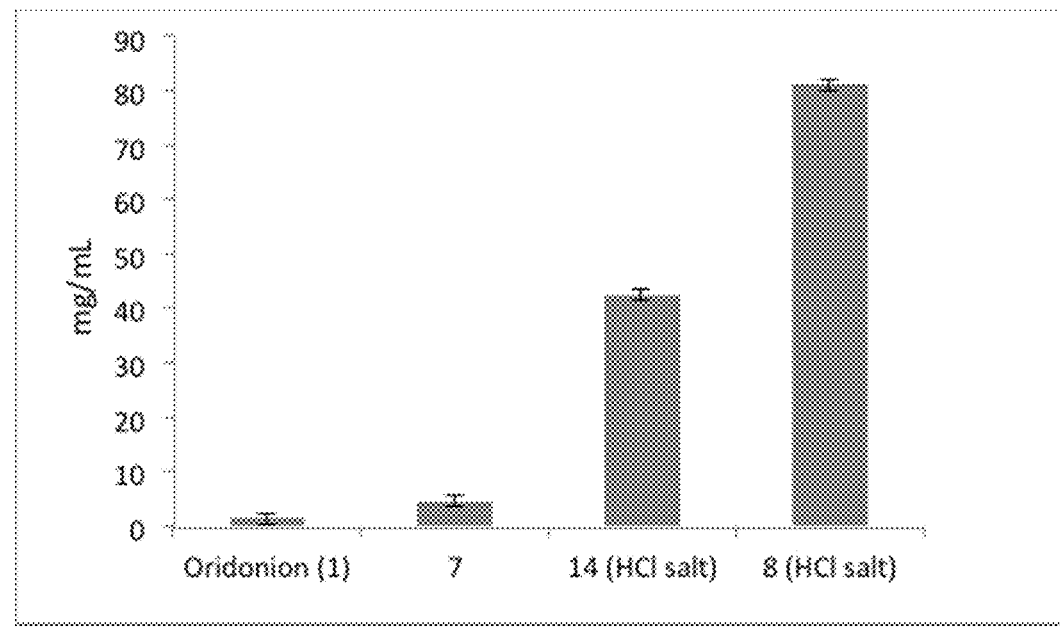
FIG. 2. Aqueous solubility of oridonin analogs. Compounds 7 (CYD-6-19), 14 (CYD-6-18) and 8 (CYD-5-54) showed significantly improved solubility compared with oridonin. Compounds 14 (HCl salt) and 8 (HCl salt) are soluble in water at a concentration of 42.38 mg/mL and 81.15 mg/mL, respectively, which are approximately 32- and 62-fold better than oridonin (1.29 mg/mL).

Moreover, these thiazole-fused oridonin derivatives have improved aqueous solubility in comparison with oridonin. The aqueous solubility of analog CYD-6-19 with 2-methyl thiazole moiety was determined to be 4.47 mg/mL, and the N-alkyl derivatives CYD-6-18 and CYD-5-54 in the form of HCl salt demonstrated a solubility with a saturated concentration of 42.38 mg/mL and 81.15 mg/mL, respectively, indicating 32-fold to 62-fold improvement in comparison with that of oridonin (1.29 mg/mL) (FIG. 2). Some other analogs such as compounds CYD-6-20 and CYD-6-29 (HCl salt) possess an even superior aqueous solubility greater than 100 mg/mL.

Figure 3A:
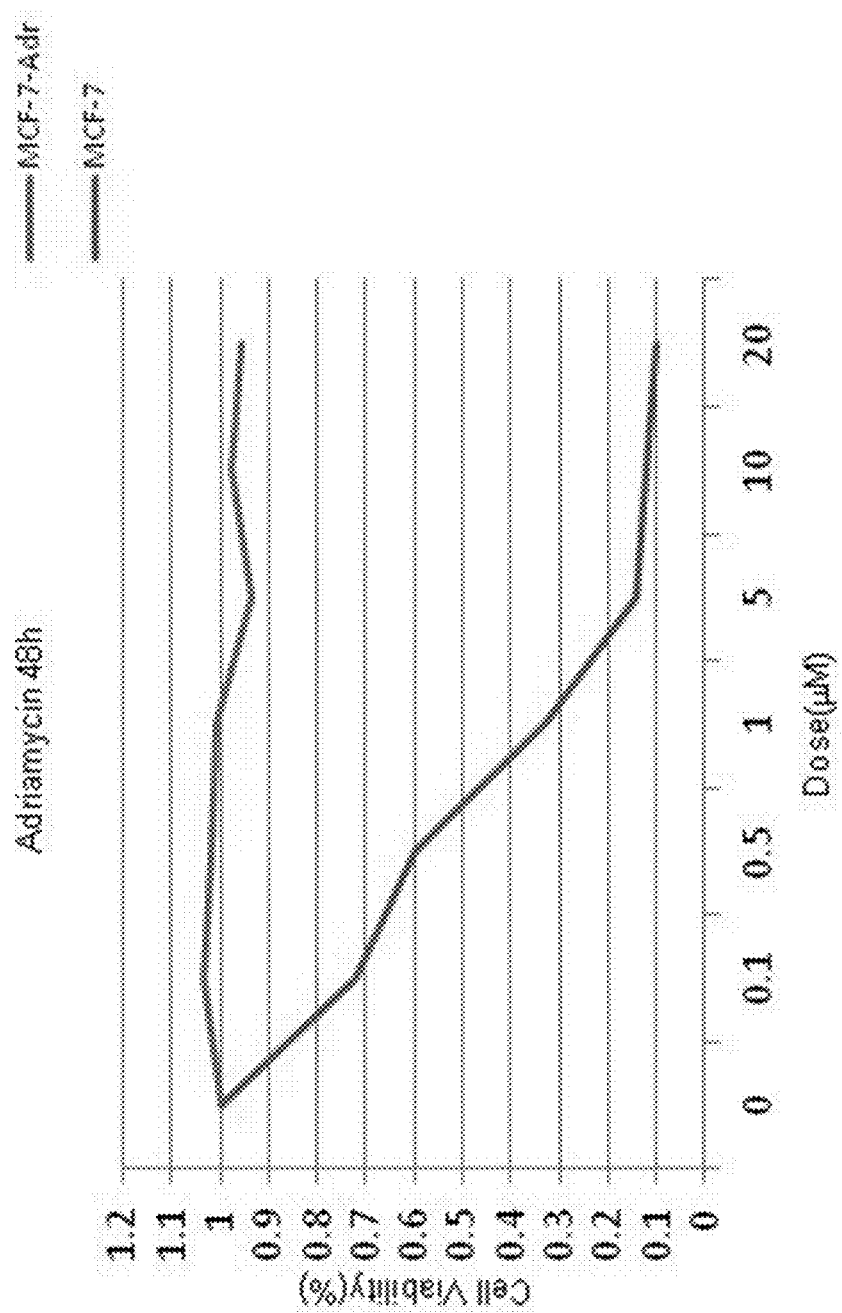
FIGS. 3A-3B. Effects of oridonin and its analogues on growth in drug-resistant MCF-7 cells.
Figure 3B:
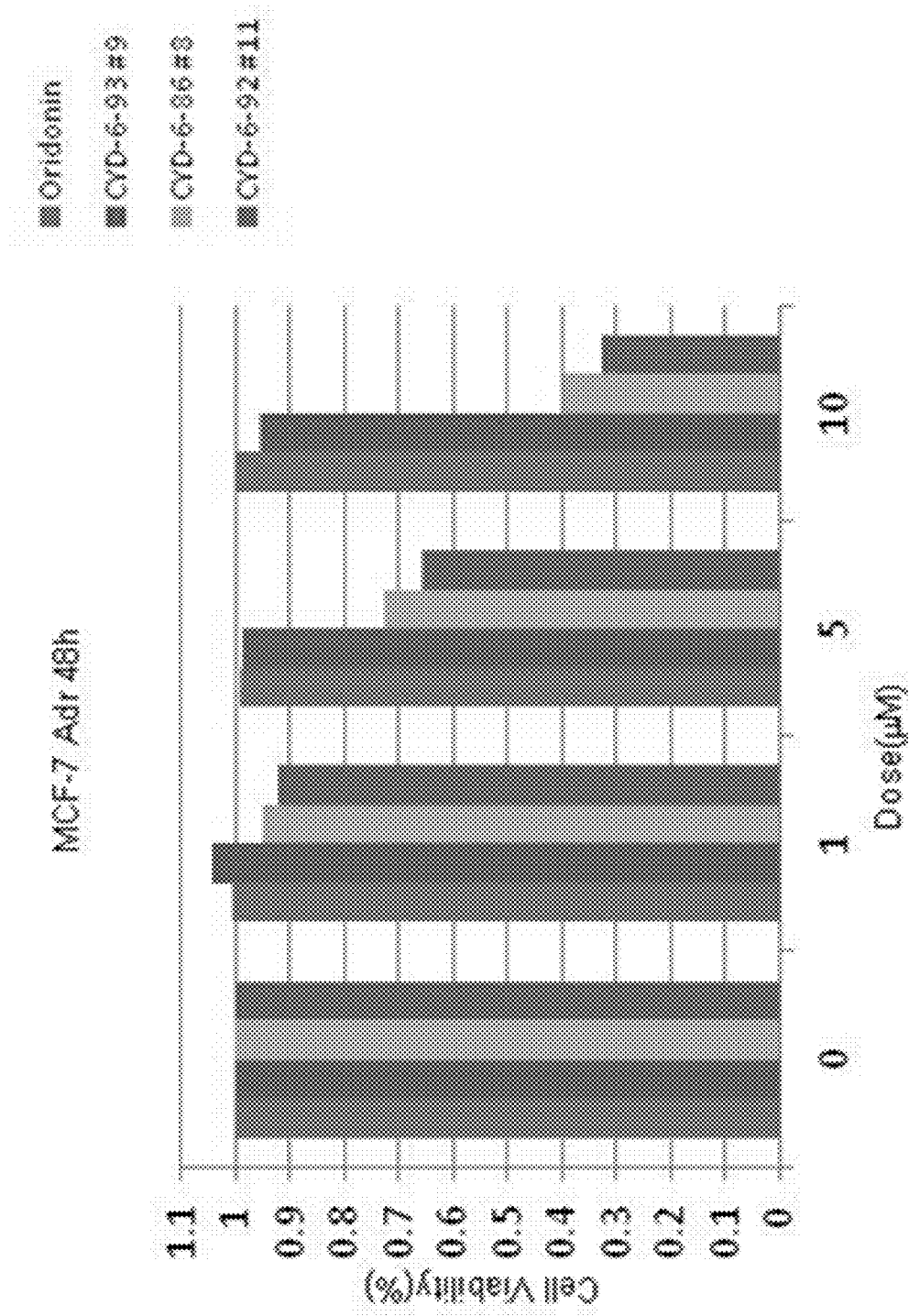
Figure 4:
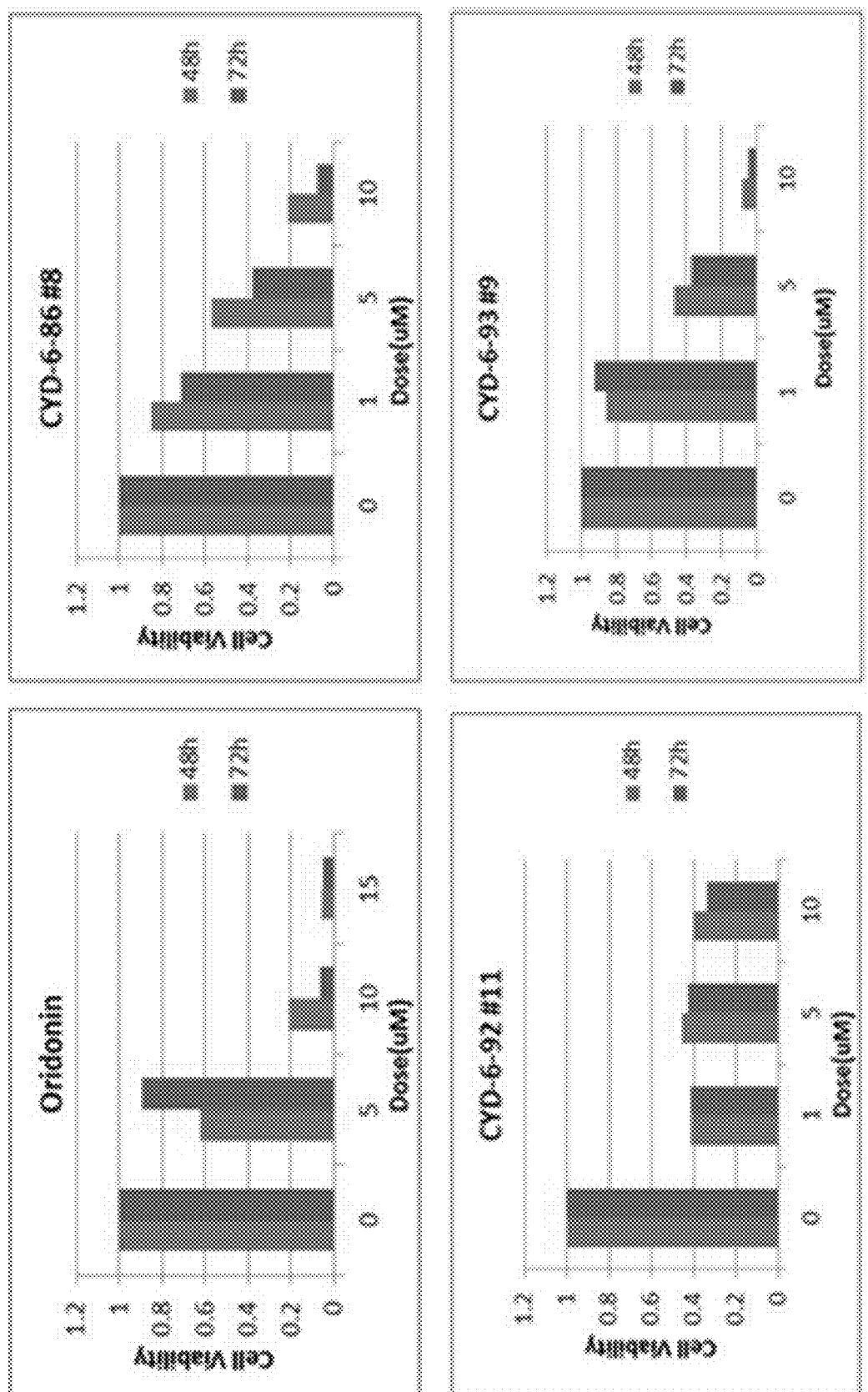
FIG. 4. Effects of oridonin and its analogues on growth in mammary epithelial MCF-10A cells.

A number of dienone analogs such as CYD-6-86, and CYD-6-92 have been identified with potent anti-proliferation effects against breast, pancreatic, and prostate cancer cell lines with low micromolar to nanomolar $IC_{50}$ values (Table 2). Moreover, oridonin analogs described herein significantly induce apoptosis against estrogen receptor (ER)-negative including triple-negative, and drug-resistant breast cancer cells (FIG. 3), while displayed less toxicity towards mammary epithelial cells (FIG. 4) when compared with oridonin.

TABLE 2a

Effects of A-ring modified oridonin analogues on proliferation of human breast, pancreatic cancer and prostate cancer cell lines.

| Compound | Structure | IC$_{50}$ (μM)[a] | | | |
| --- | --- | --- | --- | --- | --- |
| | | Breast cancer | | Pancreatic cancer | |
| | | MCF-7 | MDA-MB-231 | AsPC1 | Panc-1 |
| Oridonin | 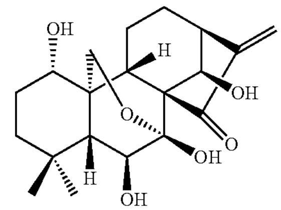 | 6.64 | 29.42 | 34.47 | 13.37 |
| CYD-6-75 | 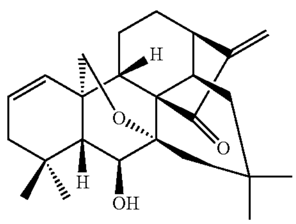 | 0.95 | 3.95 | 6.78 | 7.25 |
| CYD-6-82 | 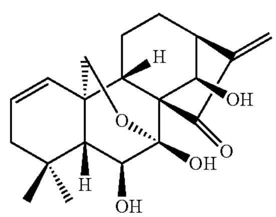 | 0.79 | 3.90 | 1.09 | 1.19 |
| CYD-6-25 | 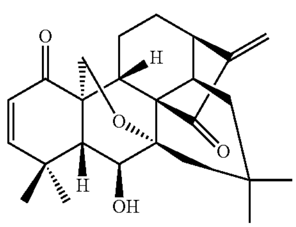 | 1.10 | 5.60 | 8.82 | 7.93 |
| CYD-6-58 | 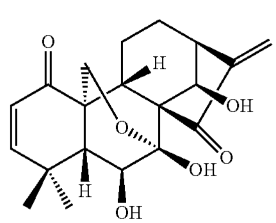 | 0.95 | 3.56 | 2.99 | >10 |
| CYD-6-81 | 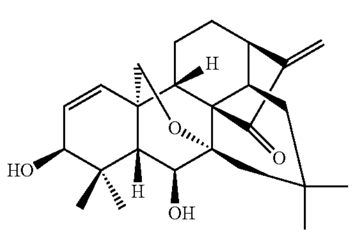 | 2.56 | 10.49 | >10[b] | 5.24 |

TABLE 2a-continued

Effects of A-ring modified oridonin analogues on proliferation of human breast, pancreatic cancer and prostate cancer cell lines.

| Compound | Structure | IC$_{50}$ (μM)$^a$ | | | |
| --- | --- | --- | --- | --- | --- |
| | | Breast cancer | | Pancreatic cancer | |
| | | MCF-7 | MDA-MB-231 | AsPC1 | Panc-1 |
| CYD-6-90 | 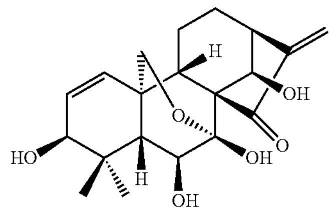 | 1.21 | 26.06 | >10 | >10 |
| CYD-6-86 | 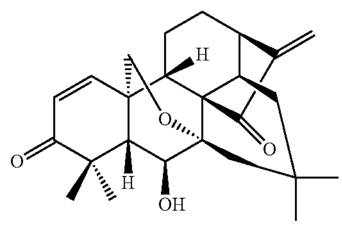 | 0.86 | 4.39 | 0.81 | 6.49 |
| CYD-6-93 | 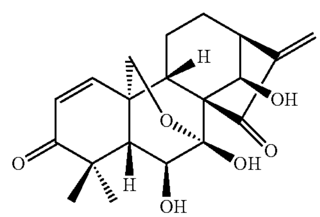 | 0.71 | 10.29 | 10.17 | 9.67 |
| CYD-6-77 | 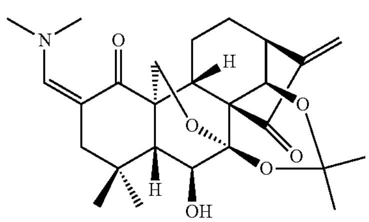 | 9.07 | 164.63 | 11.81 | >10 |
| CYD-6-92 | 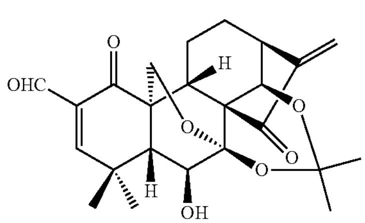 | 1.46 | 6.09 | 3.57 | 5.35 |
| CYD-7-5 | 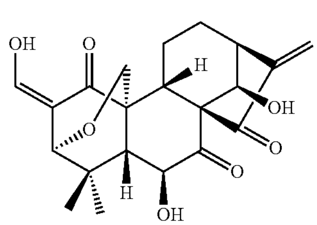 | >10 | >10 | >10 | >10 |

TABLE 2a-continued

Effects of A-ring modified oridonin analogues on proliferation of human breast, pancreatic cancer and prostate cancer cell lines.

| Compound | Structure | IC$_{50}$ (μM)[a] | | | |
| --- | --- | --- | --- | --- | --- |
| | | Breast cancer | | Pancreatic cancer | |
| | | MCF-7 | MDA-MB-231 | AsPC1 | Panc-1 |
| CYD-5-40-2 | 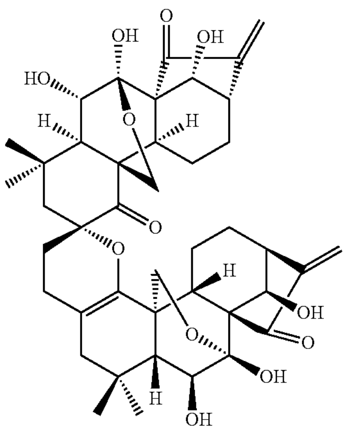 | 4.82 | 9.64 | 10.21 | 8.07 |
| CYD-6-39 | 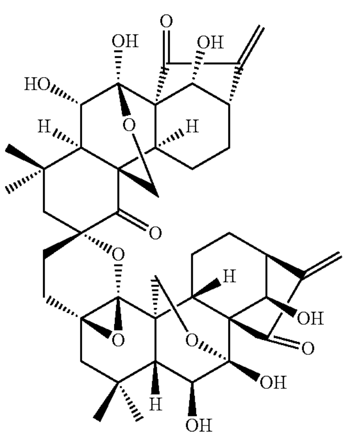 | >10 | >10 | 104.21 | >10 |

[a]Breast cancer cell lines: MCF-7 and MDA-MB-231. Pancreatic cancer cell lines: ASPC1, MiaPaCa-2 given a value >10, it indicates that a specific IC$_{50}$ cannot be calculated from the data points collected, meaning 'no effect'.

TABLE 2b
Effects of New Oridonin Analogues on Proliferation of Human Breast (MCF-7 and MDA-MB-231), Pancreatic Cancer (AsPC1 and Panc-1), and Prostate Cancer (DU145) Cells.
| Compound | MCF-7 (ER positive) | MDA-MB-231 (ER negative) | AsPC1 | Panc-1 | DU145 |
|---|---|---|---|---|---|
| Oridonin | 6.6 | 29.4 | 19.3 | 15.6 | 14.2 |
| 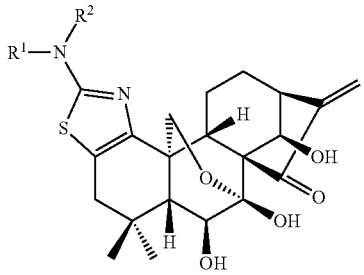 $R^1 = R^2 = H$ | 1.0 | 3.2 | 5.6 | 6.1 | 3.5 |
| 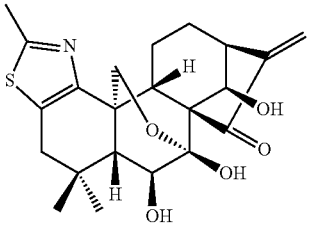 CYD-6-19 | 2.6 | 6.9 | 6.5 | 7.8 | 7.6 |
| 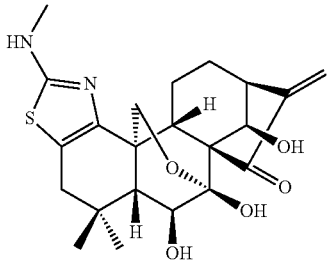 CYD-5-54 | 1.3 | 2.1 | 1.8 | 2.3 | 4.1 |
| 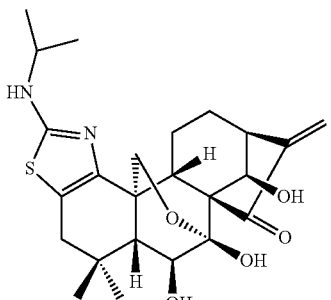 CYD-6-30 | 0.8 | 0.3 | 1.4 | 3.3 | 5.3 |

TABLE 2b-continued

Effects of New Oridonin Analogues on Proliferation of Human Breast (MCF-7 and MDA-MB-231), Pancreatic Cancer (AsPC1 and Panc-1), and Prostate Cancer (DU145) Cells.

| Compound | MCF-7 (ER positive) | MDA-MB-231 (ER negative) | AsPC1 | Panc-1 | DU145 |
|---|---|---|---|---|---|
| CYD-6-28 | 0.6 | 1.1 | 1.4 | 4.0 | 4.2 |
| CYD-6-17-2 | 0.9 | 0.8 | 1.7 | 3.7 | 1.8 |
| CYD-6-26-2 | 1.2 | 6.8 | 2.3 | 6.3 | 4.7 |
| CYD-6-20 | 1.0 | 1.8 | 1.1 | 1.5 | 1.2 |

TABLE 2b-continued

Effects of New Oridonin Analogues on Proliferation of Human Breast (MCF-7 and MDA-MB-231), Pancreatic Cancer (AsPC1 and Panc-1), and Prostate Cancer (DU145) Cells.

| Compound | MCF-7 (ER positive) | MDA-MB-231 (ER negative) | AsPC1 | Panc-1 | DU145 |
|---|---|---|---|---|---|
| CYD-6-18 | 0.2 | 0.2 | 1.1 | 1.1 | 1.2 |
| CYD-6-21 | 2.0 | 6.8 | 4.8 | 6.7 | 6.3 |
| CYD-6-29 | 3.4 | >10[b] | >10 | >10 | >10 |

[a]Breast cancer cell lines: MCF-7 and MDA-MB-231. Pancreatic cancer cell lines: AsPC1 and Panc-1. Prostate cancer cell line: DU145. Software: MasterPlex ReaderFit 2010, MiraiBio, Inc. The values are the mean ± SE of at least three independent experiments.
[b]If a specific compound is given a value >10, it indicates that a specific IC50 cannot be calculated from the data points collected, meaning "no effect".

Figure 5:
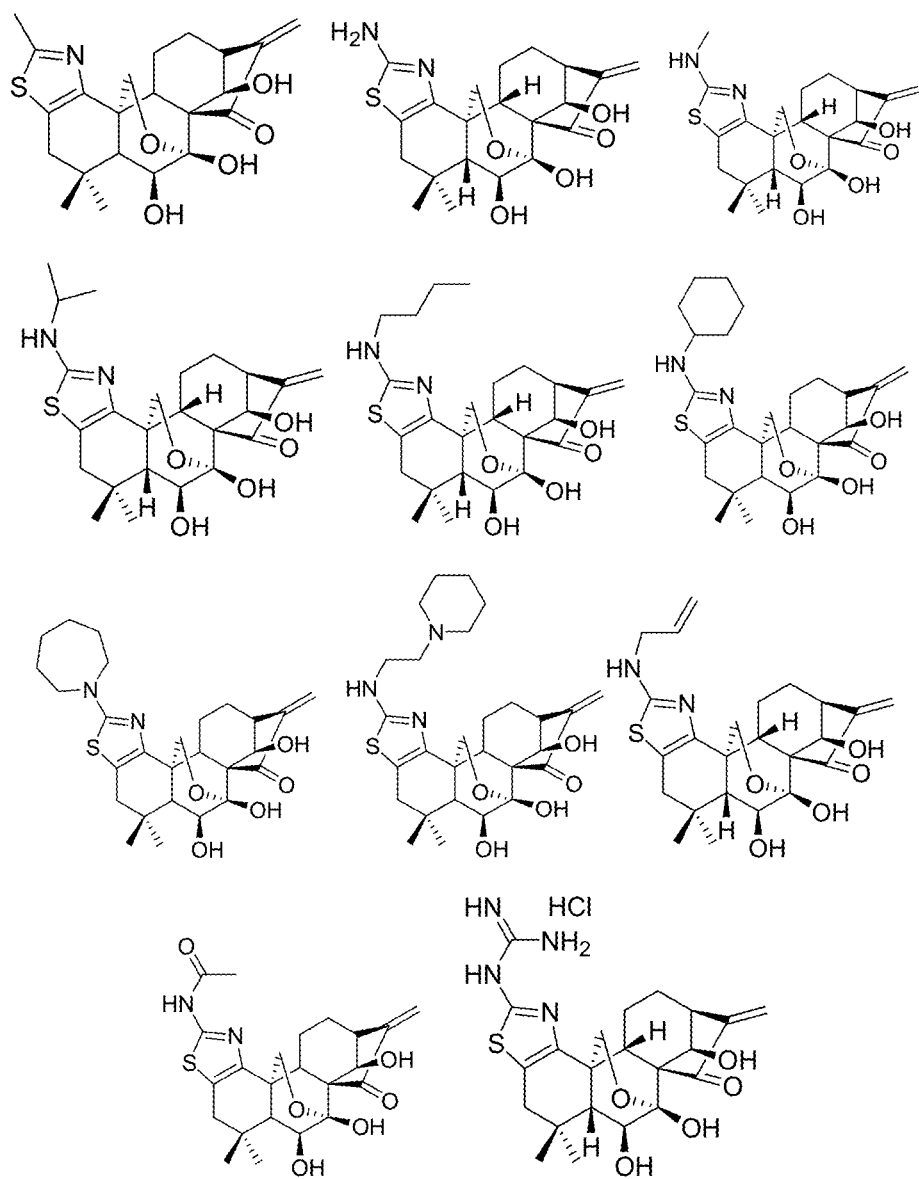
FIG. 5. Structures of molecules of Formula I.
Figure 6:
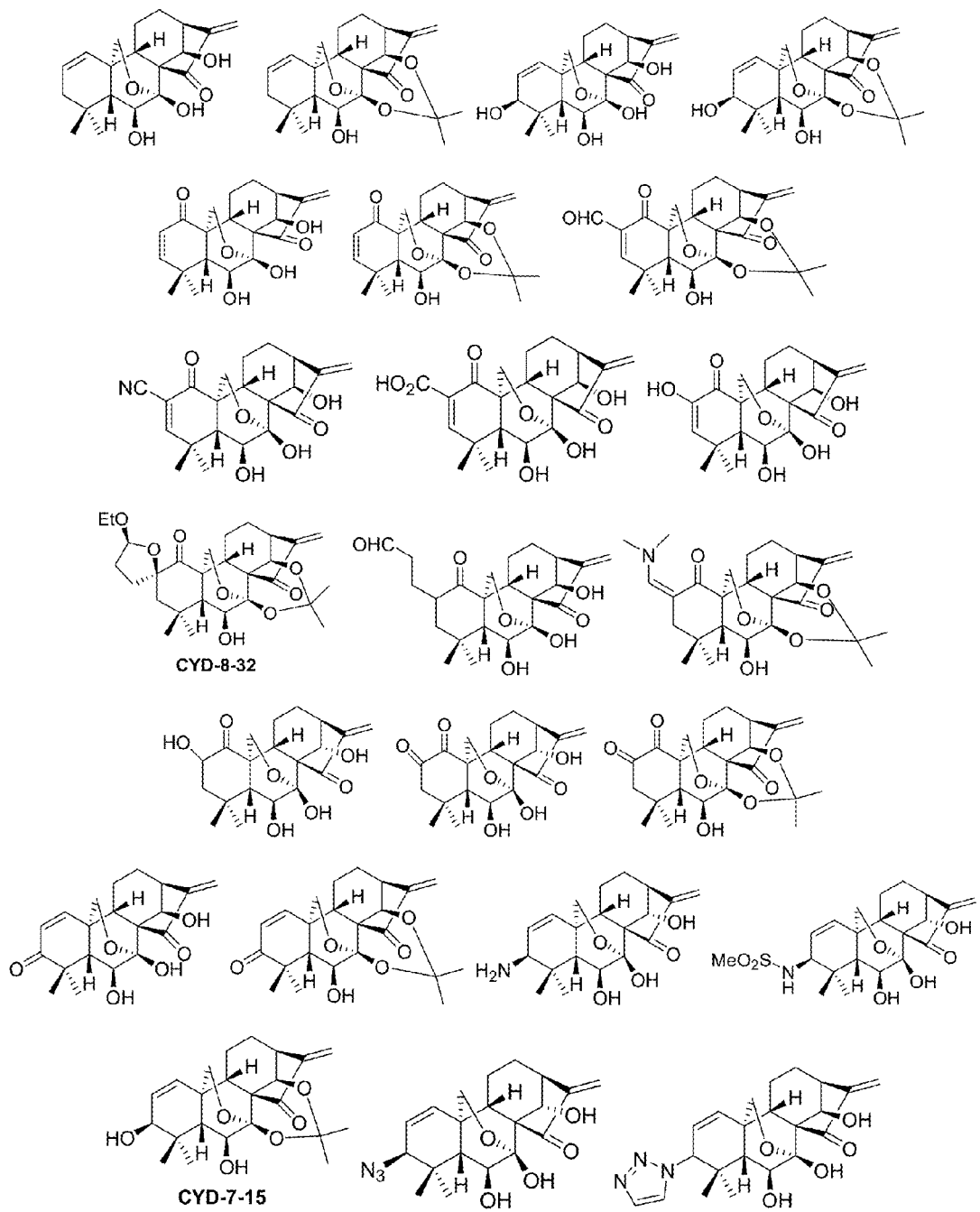
FIG. 6. Structures of molecules of Formula II.
Figure 6:
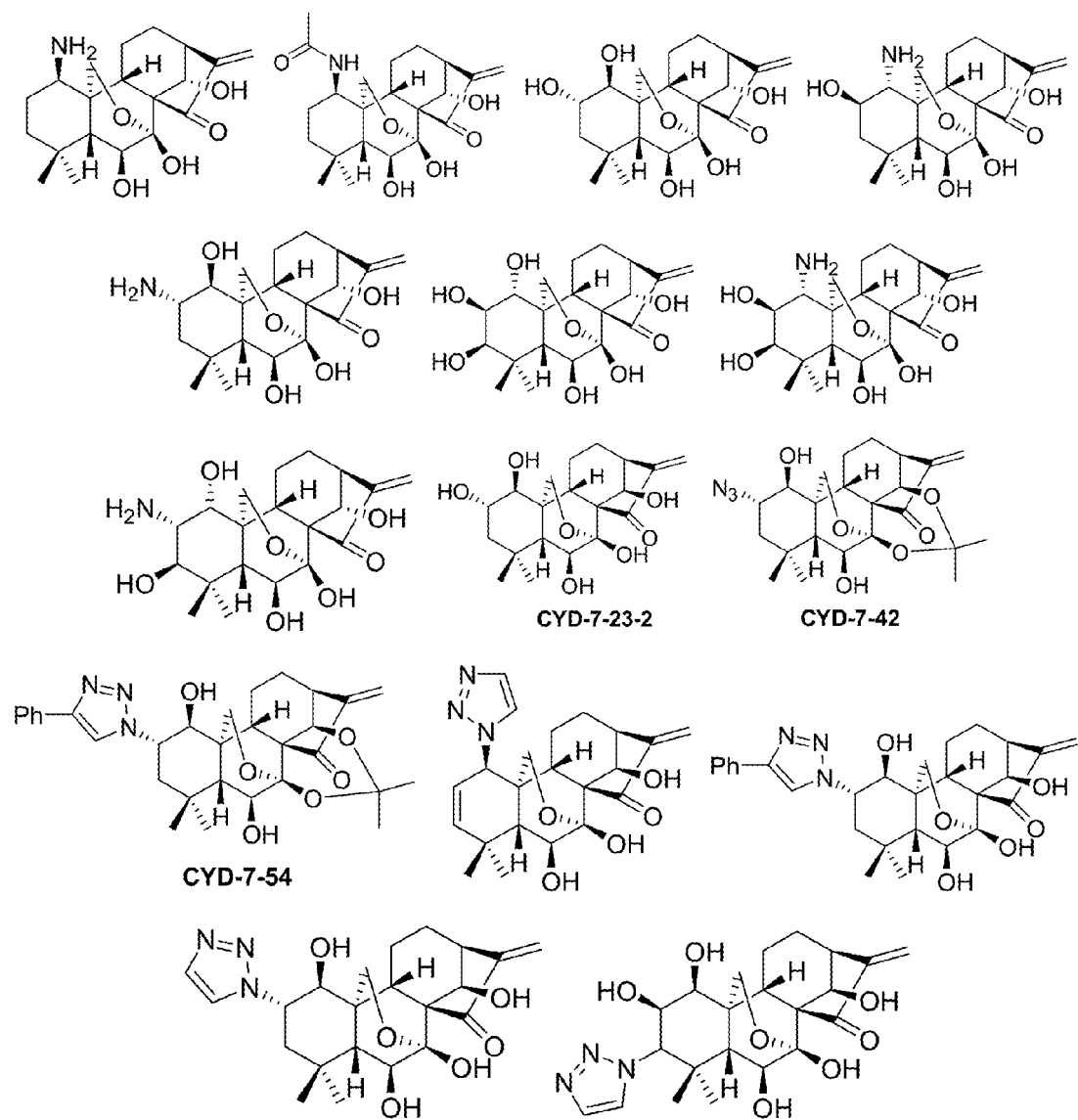
Figure 7:
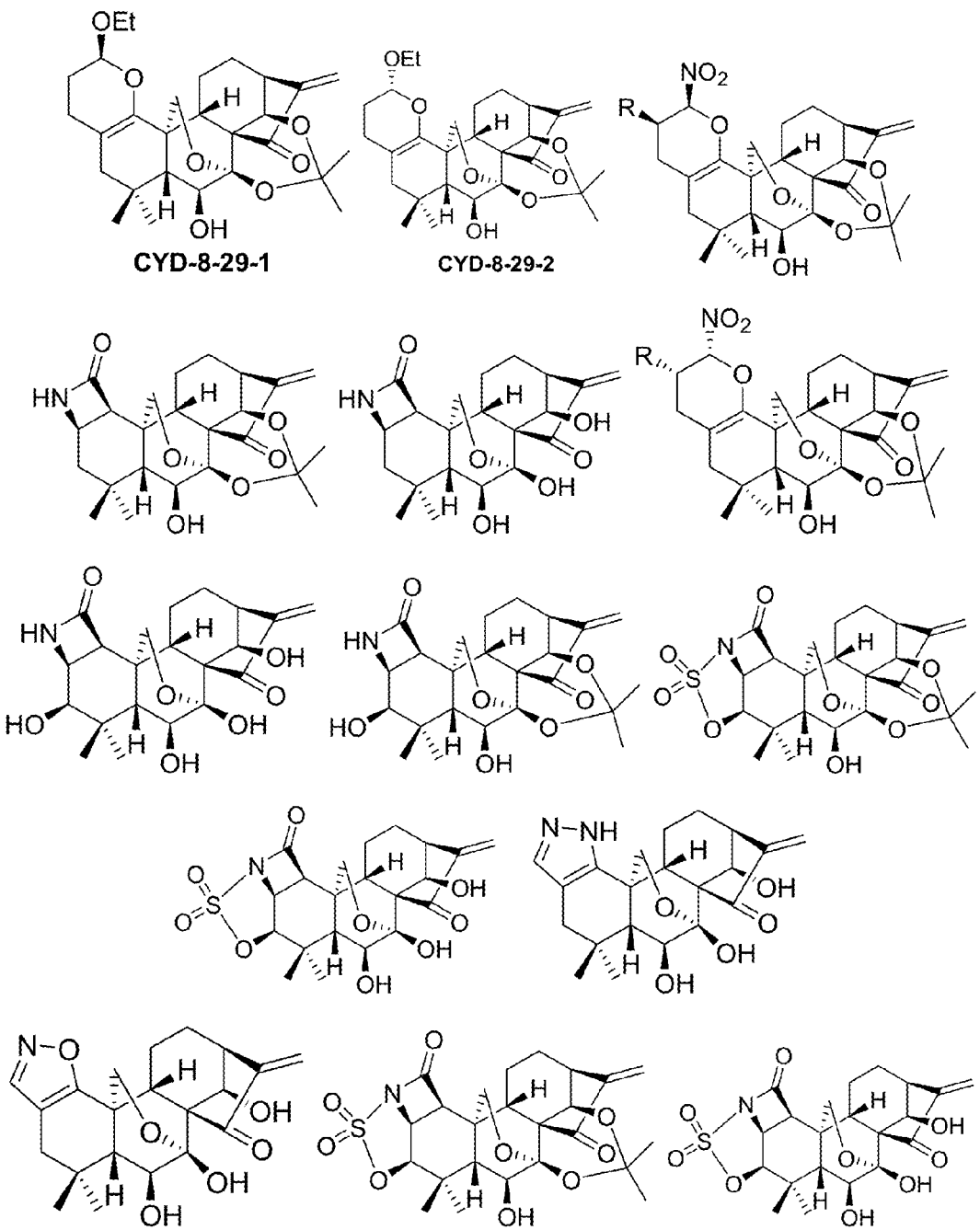
FIG. 7. Structures of molecules of Formula III.
Figure 7:
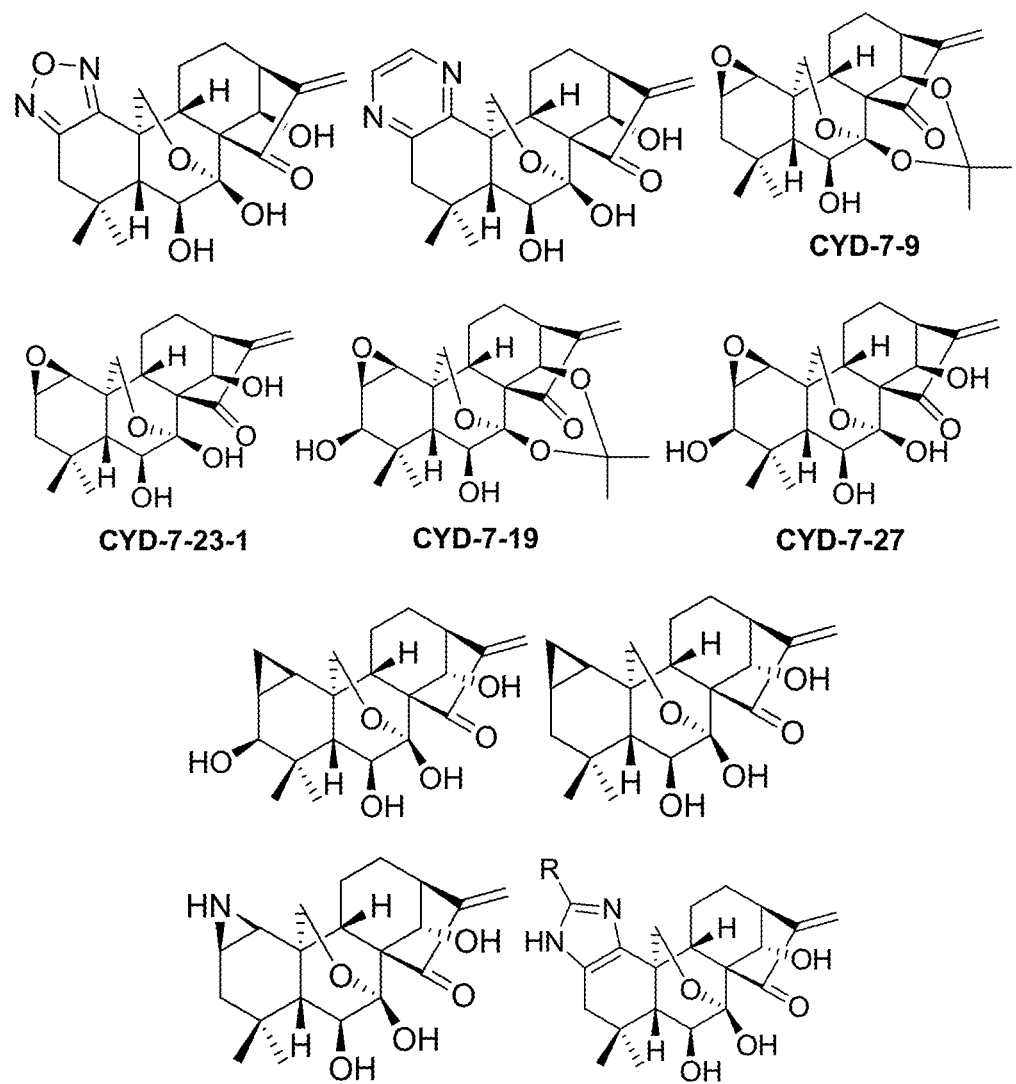
Figure 8:
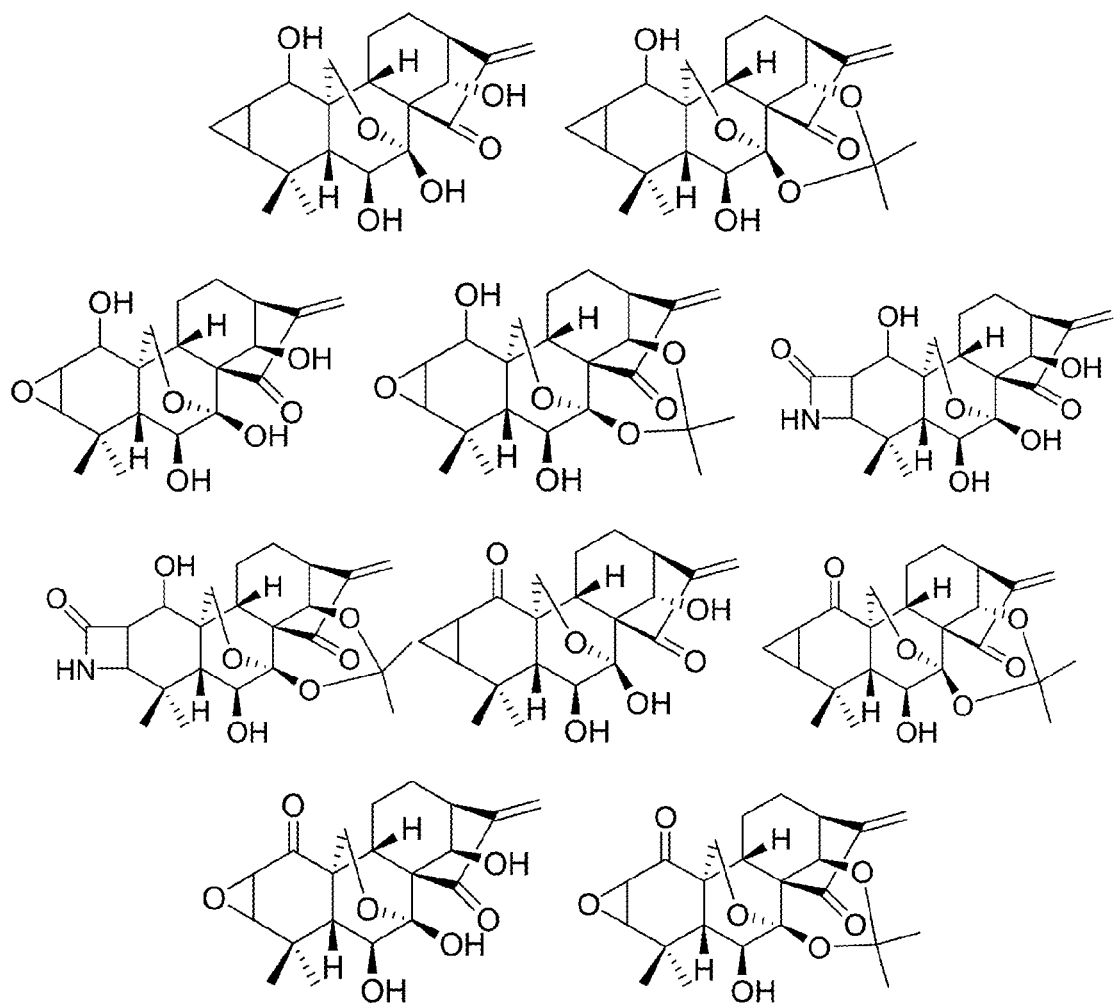
FIG. 8. Structures of molecules of Formula IV.
Figure 9:
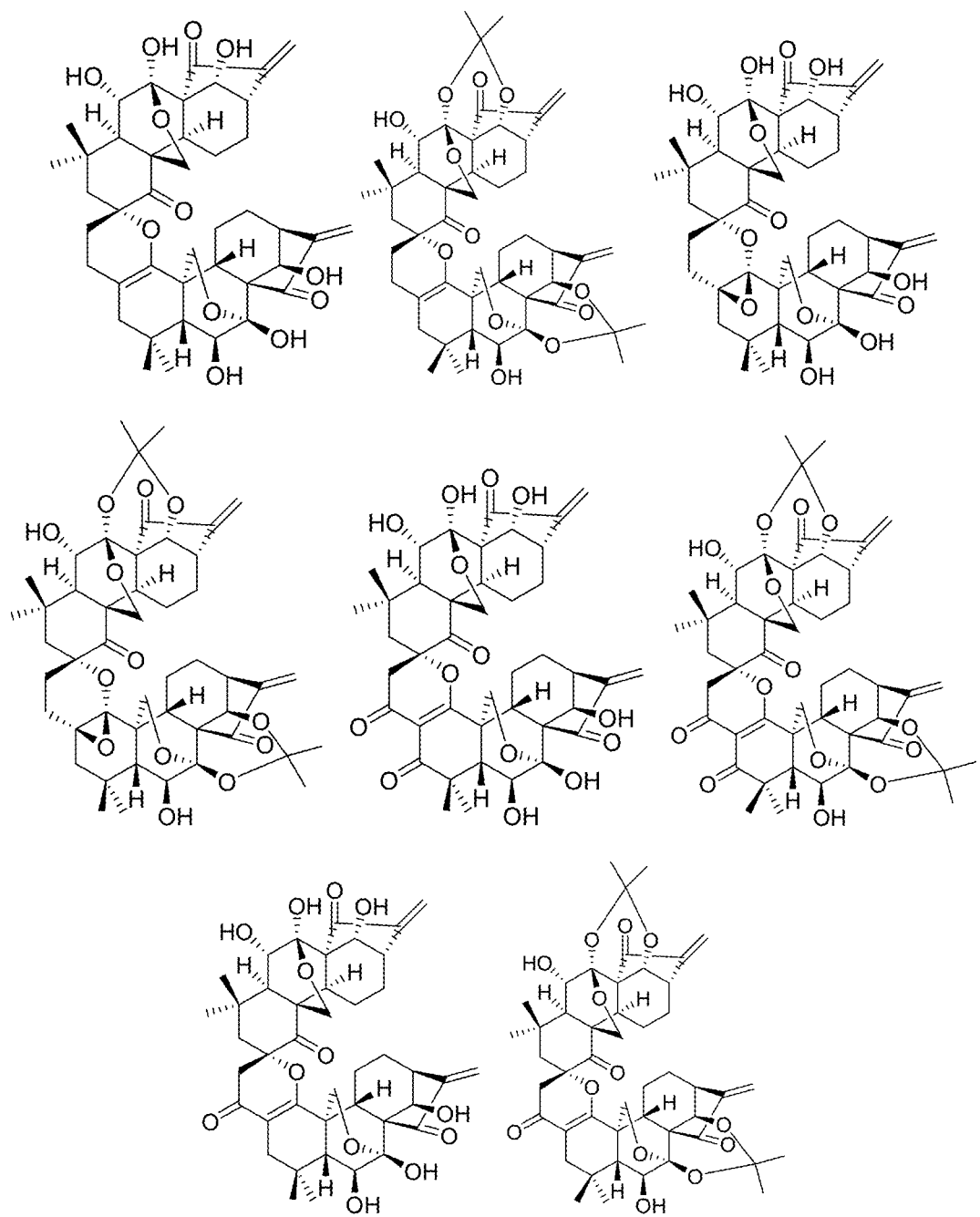
FIG. 9. Structures of molecules of Formula V.
Figure 10:
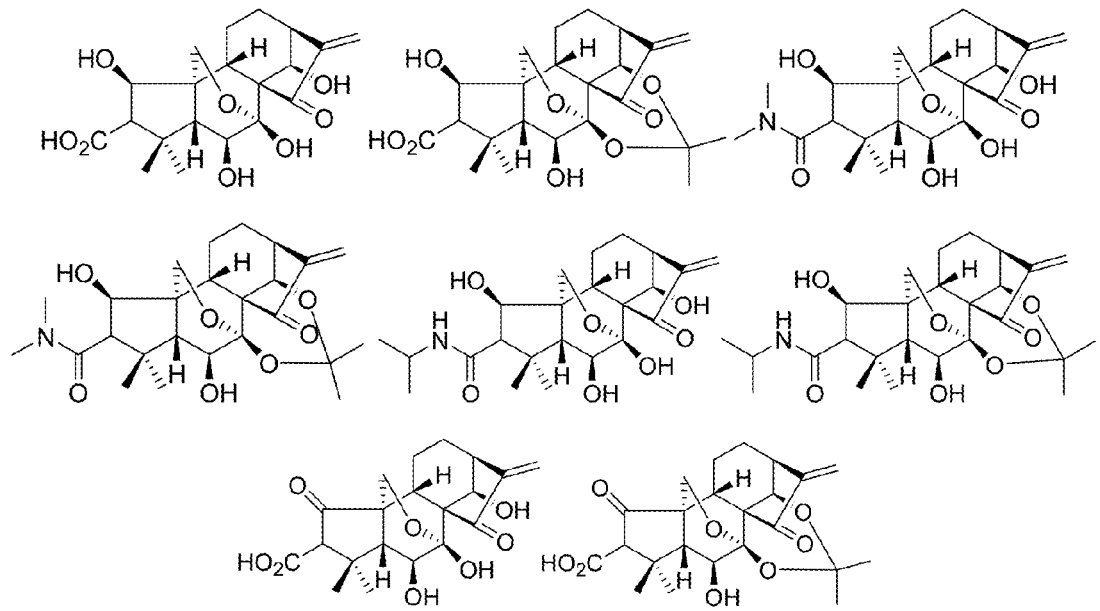
FIG. 10. Structures of molecules of Formula VI.
Figure 11:
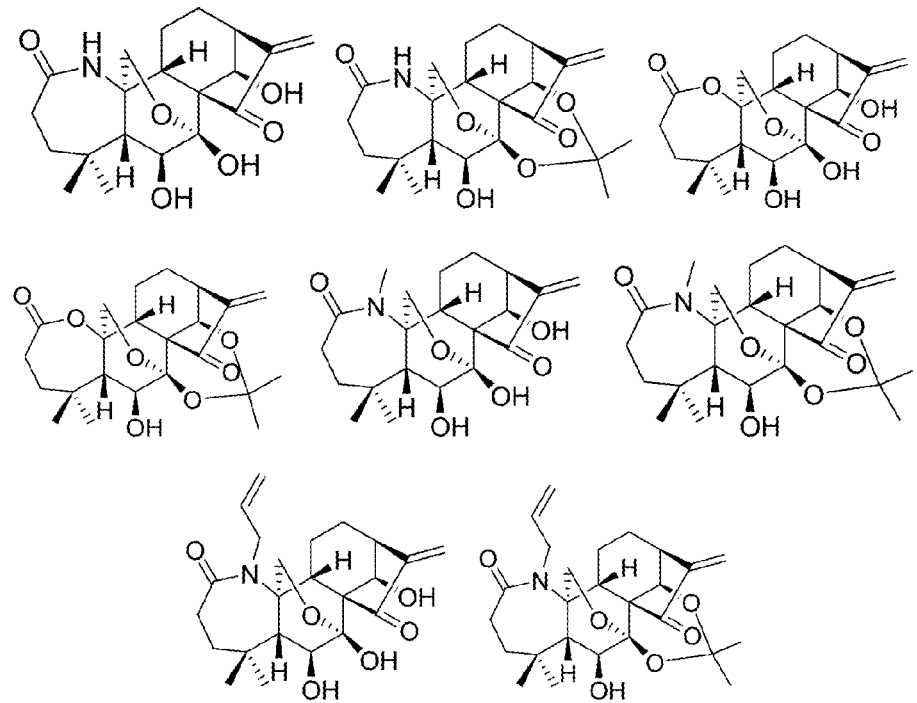
FIG. 11. Structures of molecules of Formula VII.

To further develop oridonin derivatives with anticancer potency and/or solubility, a sizable compound library of oridonin analogs is being synthesized through diversity-orientated synthesis (FIG. 5).

II. Cancer Therapy

The small molecules described herein can be developed as highly potent and orally active agents for the prevention and treatment of various cancers including but not limited to breast cancers, pancreatic cancer, brain tumors, head/neck cancer, prostate and lung cancers as well as inflammation. Although a large portion of ER-positive breast cancer can be prevented and treated with ER modulators (such as tamoxifen and raloxifene) and aromatase inhibitors (such as anastrozole and letrozole) as preventive and therapeutic drug, these available drugs fail to prevent the rest ER-positive breast cancers (approximately 45% of all ER-positive) and all ER-negative breast cancers (both accounting for approximately 60% of all breast cancer cases, including triple-negative breast cancer). In particular, ER-negative breast cancer including triple negative breast cancer does not respond to hormonal therapy and is inclined to develop metastasis. Thus, effective targets and agents are needed to prevent and treat the resistant ER-positive breast cancer and all ER-negative breast cancers, including triple negative breast cancers.

Through the medicinal chemistry efforts described herein combined with biological characterization, a number of oridonin analogs have been identified with not only enhanced anticancer activity, but also significantly improved aqueous solubility. These analogs have demonstrated antiproliferation effects against cancer cell lines, especially breast cancer cells, including estrogen receptor (ER)-negative breast cancer cell MDA-MB-231 with low micromolar to nanomolar $IC_{50}$ values. In addition, the analogs are found more effective on resistant cancer cells and less toxic to normal cells than is oridonin.

Molecules described herein may have better potency, efficacy, and drug-like properties such as water solubility and bioavailability. Some analogs may overcome resistance and provide a better cancer therapy. The small molecules described herein can be developed as highly potent and orally active agents for the prevention and treatment of various cancers including but not limited to breast cancers, pancreatic cancer, brain tumors, head/neck cancer, prostate and lung cancers, as well as inflammation.

In Vitro Determination of Effects of Synthesized Diterpenoids on Cancer Cell Proliferation. Breast cancer cell lines MCF-7, MDA-MB-231, MDA-MB-486 and MCF/ADR were seeded in 96-well plates at a density of 1×104 cells/well and treated with DMSO and 0.01, 0.1, 1, 5, 10, and 100 μM of individual compound for 48 h, and then 20 μL of 3-(4,5-dimethylthiazol-2-yl)-2,5-diphenyltetrazolium bromide (MTT) (5 mg/mL in PBS) was added to each well and further incubated for another 4 h. Then MTT solution was removed, and 150 μL of DMSO was added to each well. Absorbance of all wells was determined by measuring OD at 550 nm after a 10 min incubation on a 96-well GlowMaxate absorbance reader (Promega, Madison, Wis.). Each individual compound was tested in quadruplicate wells for each concentration.

The growth inhibitory effects of the newly generated pyran-fused diterpenoids were evaluated in four breast cancer cell lines MCF-7 (ER-positive), MDAMB-231 (ER-negative and triple-negative), MDA-MB-468 (ER-negative and triple-negative) as well as MCF-7/ADR (adriamycin-resistant) using MTT assays as described in the Experimental Section. The capability of these new molecules to inhibit the growth of cancer cells was summarized in Table 3 and compared with that of adriamycin and 1 spontaneously. Most of these new compounds not only exhibited significantly improved antiproliferative effects on breast cancer MCF-7, MDA-MB-468, and MDA-MB-231 cells relative to 1, but also displayed marked growth inhibitory activity against drug-resistant breast cancer MCF-7/ADR cells.

TABLE 3

Antiproliferative effects of pyran-fused diterpenoids against human breast cancer cells.

| Compounds | $IC_{50}$ (μM)[a] | | | |
| --- | --- | --- | --- | --- |
| | MCF-7 | MDA-MB-231 | MDA-MB-468 | MCF-7/ADR |
| Oridonin | 4.36 ± 1.41 | 28.0 ± 1.40 | 5.33 ± 1.36 | 34.79 ± 2.54 |
| Adriamycin | 0.67 ± 0.45 | 2.33 ± 0.22 | 0.65 ± 0.26 | >10[b] |
| 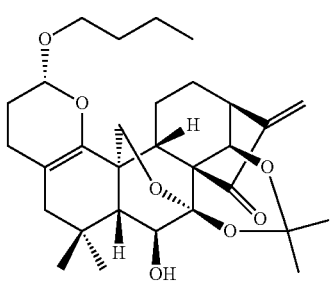 CYD-8-69-1 | 2.41 ± 1.45 | 2.23 ± 0.39 | 2.98 ± 0.67 | 3.80 ± 1.15 |
| 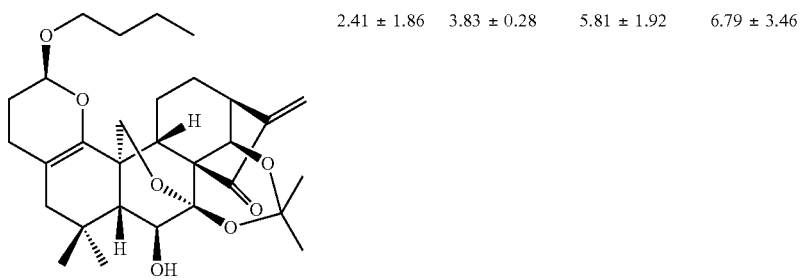 CYD-8-69-2 | 2.41 ± 1.86 | 3.83 ± 0.28 | 5.81 ± 1.92 | 6.79 ± 3.46 |

TABLE 3-continued

Antiproliferative effects of pyran-fused diterpenoids against human breast cancer cells.

| Compounds | IC$_{50}$ (μM)$^a$ | | | |
|---|---|---|---|---|
| | MCF-7 | MDA-MB-231 | MDA-MB-468 | MCF-7/ADR |
| CYD-8-45-1 | 3.52 ± 2.15 | 6.13 ± 2.43 | 5.40 ± 0.98 | 4.65 ± 3.15 |
| CYD-8-45-2 | 0.44 ± 0.27 | 0.54 ± 0.14 | 0.52 ± 0.18 | 1.64 ± 0.72 |
| CYD-8-52-1 | 2.24 ± 1.33 | 1.76 ± 0.22 | 2.62 ± 0.08 | 4.42 ± 0.90 |
| CUD-8-52-2 | 5.83 ± 3.75 | 8.18 ± 0.57 | 6.95 ± 1.01 | 10.31 ± 1.65 |

TABLE 3-continued

Antiproliferative effects of pyran-fused diterpenoids against human breast cancer cells.

| Compounds | IC$_{50}$ (μM)[a] | | | |
|---|---|---|---|---|
| | MCF-7 | MDA-MB-231 | MDA-MB-468 | MCF-7/ADR |
| CYD-8-66-1 | 4.32 ± 1.82 | 7.12 ± 0.22 | 4.89 ± 0.85 | 4.31 ± 2.43 |
| CUD-8-66-2 | 2.10 ± 0.98 | 3.30 ± 0.23 | 4.37 ± 1.48 | 3.19 ± 0.54 |
| CYD-8-65-1 | 2.31 ± 1.02 | 3.30 ± 1.81 | 2.99 ± 1.01 | 3.08 ± 1.12 |
| CYD-8-65-2 | 6.76 ± 3.43 | 7.15 ± 1.27 | 7.26 ± 0.23 | 8.74 ± 0.27 |

TABLE 3-continued
Antiproliferative effects of pyran-fused diterpenoids against human breast cancer cells.
| Compounds | IC$_{50}$ (μM)$^a$ | | | |
|---|---|---|---|---|
| | MCF-7 | MDA-MB-231 | MDA-MB-468 | MCF-7/ADR |
| 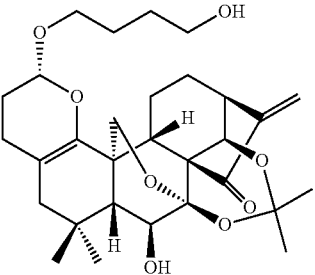 CYD-8-67-1 | 2.14 ± 1.11 | 3.18 ± 0.24 | 2.65 ± 0.14 | 4.51 ± 1.54 |
| 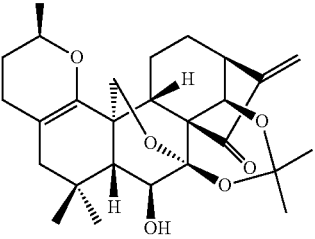 CYD-8-67-2 | 5.17 ± 2.90 | 5.89 ± 2.04 | 5.96 ± 0.29 | 5.34 ± 1.29 |
| 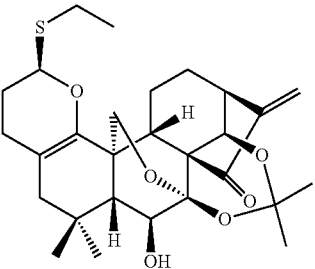 CYD-8-84 | 2.30 ± 1.40 | 2.87 ± 0.54 | 2.83 ± 0.42 | 3.82 ± 0.47 |
| 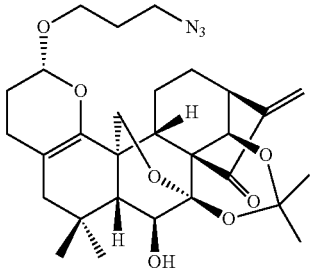 CYD-8-87 | 7.79 ± 3.18 | 7.57 ± 0.44 | 6.63 ± 0.77 | 8.60 ± 0.70 |

TABLE 3-continued

Antiproliferative effects of pyran-fused diterpenoids against human breast cancer cells.

| Compounds | IC$_{50}$ (μM)$^a$ | | | |
|---|---|---|---|---|
| | MCF-7 | MDA-MB-231 | MDA-MB-468 | MCF-7/ADR |
| 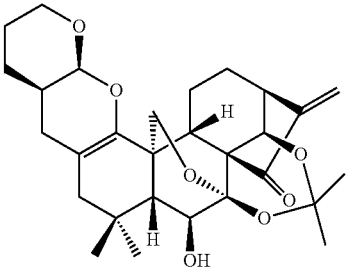 CYD-8-74-2 | 2.39 ± 0.78 | 2.53 ± 0.77 | 3.33 ± 0.58 | 2.89 ± 0.32 |
| 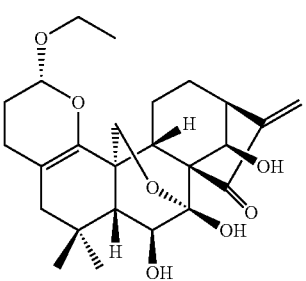 CYD-8-50 | 1.90 ± 0.97 | 3.32 ± 1.01 | 2.24 ± 0.68 | 3.18 ± 0.89 |

$^a$Software: MasterPlex ReaderFit 2010, MiraiBio, Inc. Values are the mean ± SE of three independent experiments.
$^b$If a specific compound is given a value >10, it indicates that a specific IC$_{50}$ cannot be calculated from the data points collected, meaning "no effect".

Figure 13:
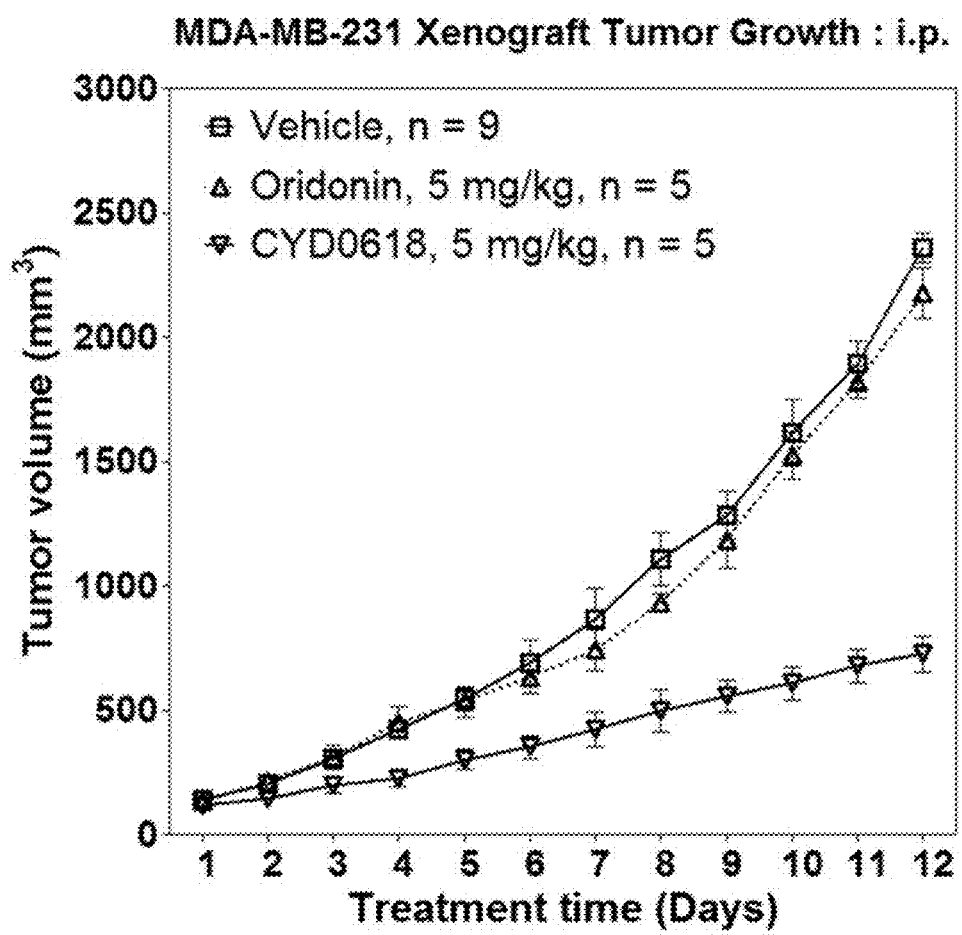
FIG. 13. In vivo efficacy of oridonin and compound CYD0618 in inhibiting growth of xenograft tumors (breast cancer MDA-MB-231) in mice (i.p.) at the dose of 5 mg/kg, respectively. Data are presented as the mean±SE of tumor volume at each time point; Significant differences between compound CYD0618 treatment group, oridonin treatment group and control were determined using one way ANOVA. p<0.0001.

Compound CYD-6-18 Suppressed Growth of Xenograft Tumors in Nude Mice. In pilot in vivo studies, this compound was further evaluated for its anticancer activity in suppression of tumor growth in the triple-negative breast cancer MDA-MB-231 xenograft model. As shown in FIG. 13, mice treated with 5.0 mg/kg of compound CYD-6-18 via ip showed a much better effect in inhibiting tumor growth as compared to the mice treated with the same dose of oridonin (p<0.0001). The compound was found to be tolerated during the experiments and showed no significant loss of body weight (data not shown). These findings suggest that compound CYD-6-18 is a promising anticancer drug candidate with potent antitumor activity and excellent aqueous solubility for further clinic development.

Figure 14:
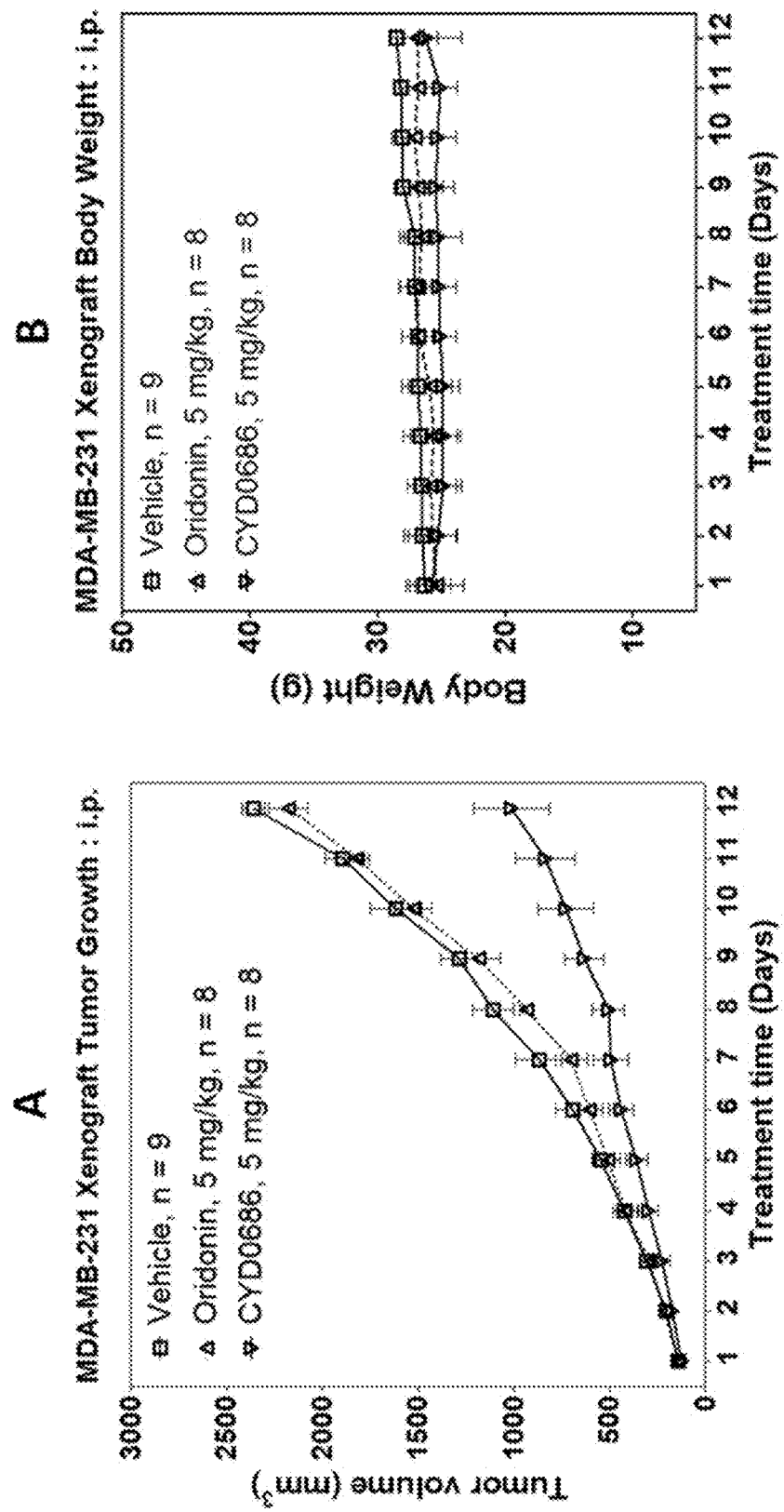
FIG. 14. In vivo therapeutic efficacy of compound CYD0686 compared to oridonin in inhibiting growth of xenograft tumors (triple-negative breast cancer cell line MDA-MB-231) in mice (i.p.) at 5 mg/kg: (A) average tumor size changes; (B) average body weight changes. Values are mean±SE of three independent experiments. Statistical significance was determined using one-way ANOVA (p<0.0001).
Figure 15:
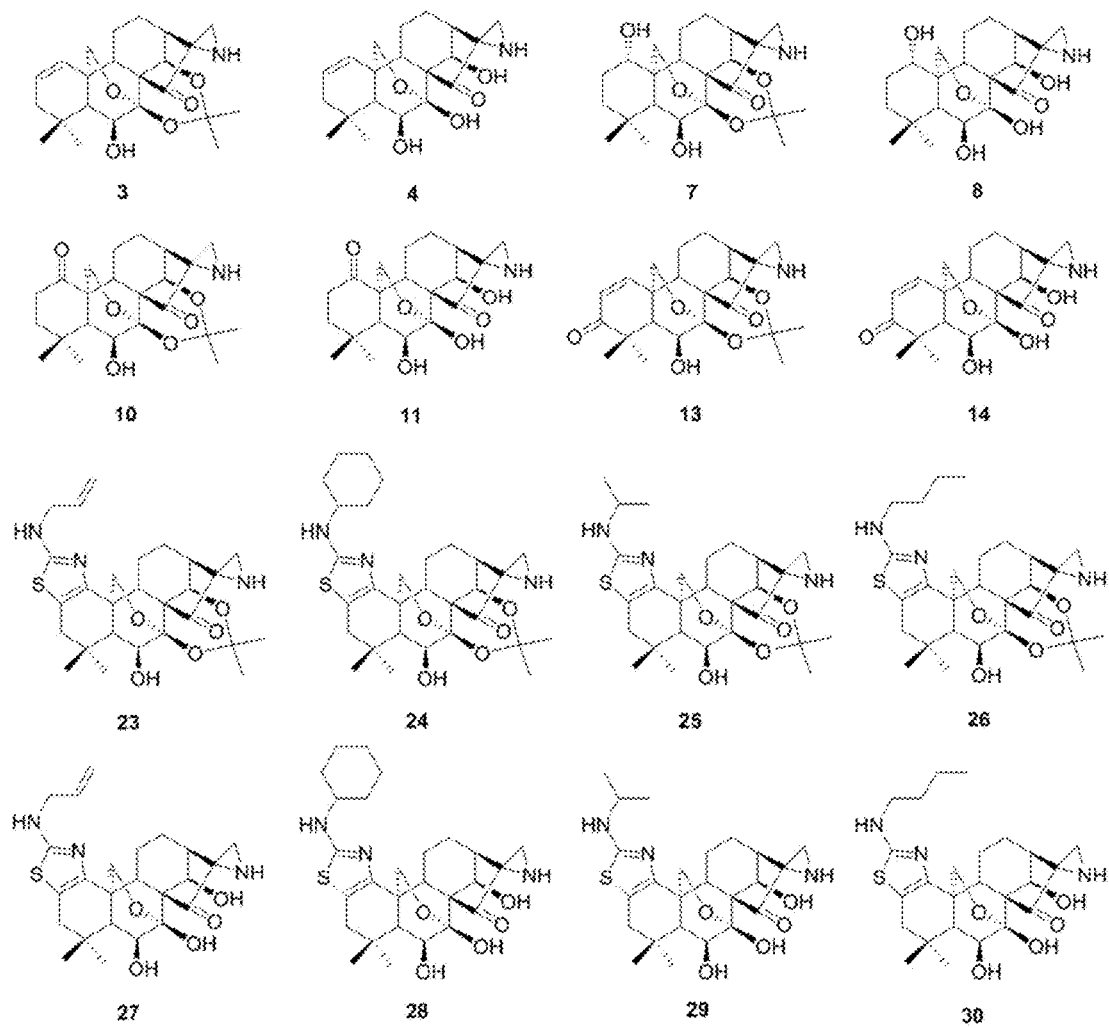
FIG. 15. Oridonin derivatives comprising an aziridine group.

Compound CYD-6-86 Suppressed Growth of Xenograft Tumors in Mice. In in vivo studies, dienone analog CYD-6-86 was further evaluated for its antitumor activity in suppression of tumor growth in the triple-negative MDA-MB-231 xenograft model because of its potent antiproliferative and colony formation inhibitory effects in MDA-MB-231 cells as well as lower toxicity in HMEC cells. The compound was selected for further in vivo efficacy studies because of its good in vitro dose-response relationship. As shown in FIG. 14A, compound CYD-6-86 at 5.0 mg/kg was much more efficacious in suppressing xenograft tumor growth as compared to oridonin at the same dosage (p<0.0001). The compound was also found to be well tolerated during experiments and showed no significant loss of body weight (FIG. 14B). These results suggest that compound CYD-6-86 is a promising anticancer drug candidate with potent antitumor activity and good tolerability for further clinical development.

III. Chemical Definitions

Various chemical definitions related to such compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein, the term "water soluble" means that the compound dissolves in water at least to the extent of 0.010 mole/liter or is classified as soluble according to literature precedence.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

As used herein, the term "nitro" means —NO$_2$; the term "halo" designates —F, —Cl, —Br or —I; the term "mercapto" means —SH; the term "sulfonate ester" means —OSO$_2$R', the term "cyano" means —CN; the term "azido" means —N$_3$; the term "imino" means =NH; the term "azo"

means —RN=NR; the term "thioyl" means —SH; the term "sulfonyl" means —SO$_2$R; The term "sulfinyl" means —S(O)R; the "sulfo" means —SO$_3$; the term "silyl" means —SiH$_3$, the term "hydroxy" means —OH, and the term "hydroxyalkyl" means —ROH.

The term "amino" means a group having the structure —NR'R" (the term includes primary, secondary, and tertiary amines), the term "amide" means —C(O)NR'R", R' and R" are independently hydrogen or an optionally substituted alkyl, heteroalkyl, cycloalkyl, or heterocyclyl group.

The term "oxo" as used herein means an oxygen that is double bonded to a carbon atom.

The term "alkyl," by itself or as part of another substituent, means, unless otherwise stated, a linear (i.e. unbranched) or branched carbon chain, which may be fully saturated, mono-or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —CH$_3$ (Me), —CH$_2$CH$_3$ (Et), —CH$_2$CH$_2$CH$_3$ (n-Pr), —CH(CH$_3$)$_2$ (iso-Pr), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tent-butyl), —CH$_2$C(CH$_3$)$_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C (CH$_3$)$_3$, and —CH$_2$Si(CH$_3$)$_3$.

The terms "alkenyl" and "alkynyl" refer to unsaturated aliphatic groups analogous in length and possible substitution to the alkyls described above, but that contain at least one double or triple bond respectively. Alkenyl or alkynyl are optionally substituted.

The term "alkylsulfonyl" as used herein means a moiety having the formula —S(O$_2$)—R', where R' is an alkyl group. R' may have a specified number of carbons (e.g. "C$_{1-4}$ alkylsulfonyl"). Alkyl sulfonyl is optionally substituted.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl. Alkoxy is optionally substituted.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Cycloalkyl or heterocyclyl can be saturated or unsaturated or polyunsaturated.

The term "aryl" means a polyunsaturated hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S.

A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl (—C(O)NR$_2$), unsubstituted alkyl, unsubstituted heteroalkyl, alkoxy, alkylthio, alkylamino, (alkyl)$_2$amino, alkylsulfinyl, alkylsulfonyl, arylsulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(C$_{1-4}$alkyl)$_2$, —NO$_2$, —S(C$_{1-4}$alkyl), —SO$_2$(C$_{1-4}$alkyl), —CO$_2$(C$_{1-4}$alkyl), and —O(C$_{1-4}$alkyl).

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

(4aR,5S,6S,6aR,9S,11aS,11bS,14R)-5,6,14-trihydroxy-4,4-dimethyl-8-methylenedecahydro-1H-6,11b-(epoxymethano)-6a,9-methanocyclohepta[α]naphthalene-1,7(8H)-dione (CYD-5-28)

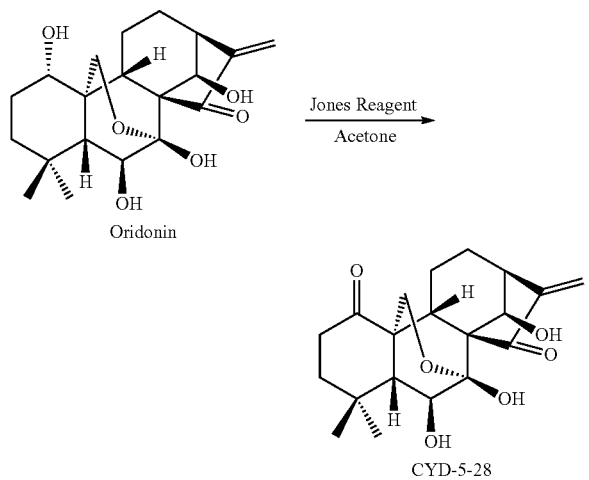

To a stirring solution of oridonin (500 mg, 1.37 mmol) in acetone (40 mL) was added Jones reagent (0.6 mL) dropwise at ice-water bath. The resulting mixture was stirred at 0° C. for 20 min, and isopropanol was added to quench excess Jones reagent. Then the mixture was diluted with water and extracted with dichloromethane. The extract was washed with brine, dried over anhydrous Na$_2$SO$_4$, filtered, and evaporated to give a solid crude product. The crude residue was recrystallized from acetone-hexane to give CYD-5-28 as a white solid (410 mg, 82%); mp 219-220° C. (Lit. mp 219-221° C.). $^1$H NMR (600 MHz, (CD$_3$)$_2$CO): δ 6.52 (br s, 1H), 6.10 (s, 1H), 5.62 (s, 1H), 5.41 (d, 1H, J=10.8 Hz), 5.24 (s, 1H), 4.91 (s, 1H), 4.22 (d, 1H, J=10.2 Hz), 3.92 (d, 1H, J=10.8 Hz), 3.69 (m, 1H), 3.31 (br s, 1H), 3.01 (d, 1H, J=9.6 Hz), 2.76 (m, 5H), 2.46 (m, 1H), 2.36 (m, 1H), 2.19 (m, 1H), 1.92 (m, 3H), 1.68 (m, 1H), 1.61 (m, 1H), 1.19 (m, 1H), 1.14 (s, 3H), 0.97 (s, 3H).

Example 2

(4aR,5S,6S,6aR,9S,11aS,11bS,14R)-2-bromo-5,6,14-trihydroxy-4,4-dimethyl-8-methylenedecahydro-1H-6,11b-(epoxymethano)-6a,9-methanocyclohepta[α]naphthalene-1,7(8H)-dione (CYD-5-38).

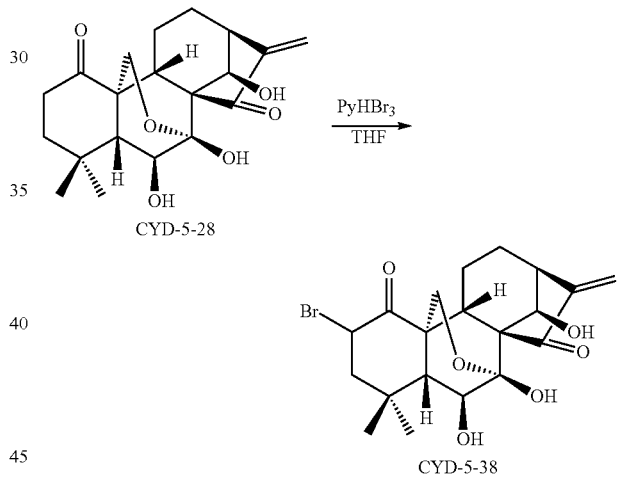

To a solution of CYD-5-28 (100 mg, 0.27 mmol) in THF (4 mL) was added PyHBr$_3$ (88 mg, 0.27 mmol) at room temperature. The reaction mixture was stirred at room temperature (rt) for 4 h and then poured into water and extracted with CH$_2$Cl$_2$ (30 mL×3). The organic layer was washed with brine, dried over anhydrous Na$_2$SO$_4$, and concentrated in vacuo to give an oily residue. The residue was purified by silica gel column; elution with 50% EtOAc in hexane afforded the desired product CYD-5-38 (80 mg, 66%) as a colorless amorphous gel; one isomer: $^1$H NMR (600 MHz, CDCl$_3$): δ 6.26 (s, 1H), 6.09 (d, 1H, J=11.4 Hz), 6.00 (br s, 1H), 5.65 (s, 1H), 4.91 (s, 1H), 4.72 (br s, 1H), 4.31 (m, 2H), 3.97 (d, 1H, J=10.8 Hz), 3.80 (m, 1H), 3.08 (d, 1H, J=9.0 Hz), 2.59 (dd, 1H, J=4.8 Hz, 13.2 Hz), 2.24 (d, 1H, J=8.4 Hz), 2.12 (m, 1H), 1.90 (m, 1H), 1.65 (m, 1H), 1.43 (m, 1H), 1.21 (s, 3H), 0.98 (s, 3H); $^{13}$C NMR (150 MHz, CDCl$_3$): δ 206.4, 202.6, 150.6, 122.3, 98.0, 72.9, 72.2, 65.6, 61.7, 58.1, 52.2, 49.8, 48.4, 45.1, 42.7, 33.8, 29.8, 29.4, 22.3, 18.1; another isomer: $^1$H NMR (600 MHz, CDCl$_3$): δ 6.26 (s, 1H), 5.98 (d, 1H, J=12.0 Hz), 6.00 (br s, 1H), 5.66

(s, 1H), 4.87 (s, 1H), 4.80 (m, 1H), 4.39 (d, 1H, J=10.8 Hz4), 4.06 (d, 1H, J=10.8 Hz), 3.80 (m, 1H), 3.08 (d, 1H, J=9.0 Hz), 2.67 (m, 1H), 2.36 (d, 1H, J=5.4 Hz), 2.33 (d, 1H, J=5.4 Hz), 2.12 (m, 1H), 1.90 (m, 1H), 1.65 (m, 1H), 1.25 (m, 1H), 1.22 (s, 3H), 1.05 (m, 1H), 1.04 (s, 3H). $^{13}$C NMR (150 MHz, CDCl$_3$): δ 206.2, 202.6, 150.5, 122.6, 98.0, 72.9, 71.9, 64.5, 61.2, 58.7, 51.4, 49.8, 48.9, 45.1, 42.6, 34.8, 30.4, 29.3, 24.9, 18.9. HRMS calc. for C$_{20}$H$_{25}$BrO$_6$: [M+H]$^+$ 441.0907; found 441.0909.

Example 3

(6S,7 S,7aR,10R,12bR,15R)-6,7,15-trihydroxy-2,5,5-trimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-5-19)

Example 4

(5aR,6S ,7S,7aR,10S,12aS,12bR,15R)-2-amino-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-5-41)

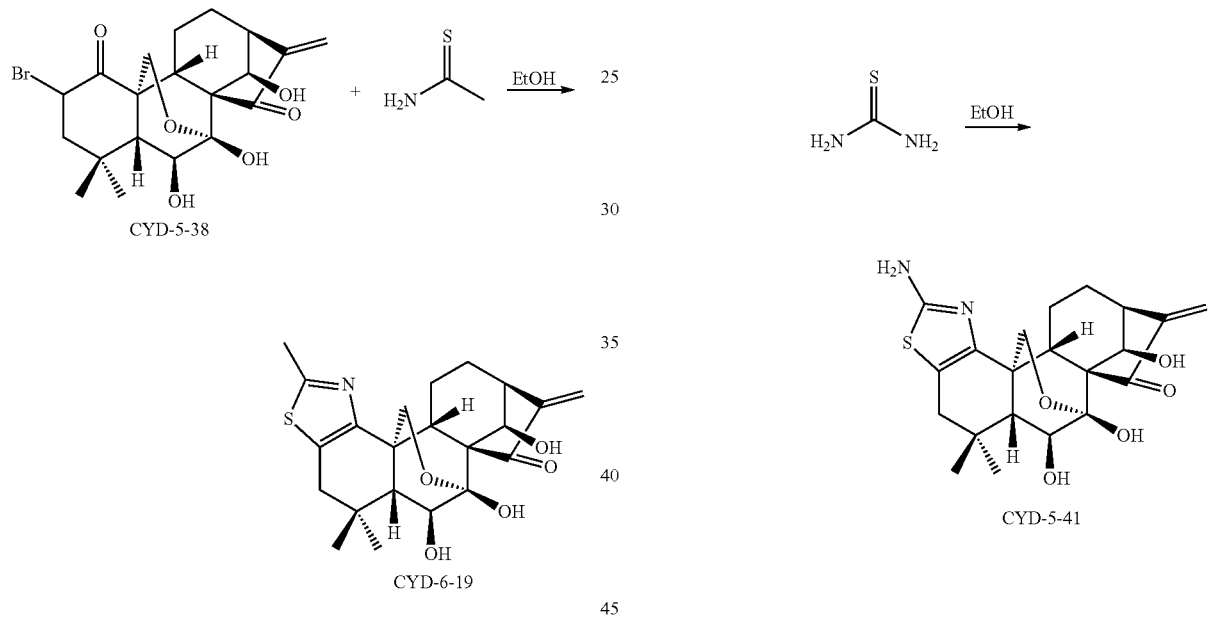

To a solution of CYD-5-38 (50 mg, 0.11 mmol) in ethanol (4 mL) was added thioacetamide (12 mg, 0.16 mmol) at room temperature. The reaction mixture was heated under reflux for 3 h. After cooling, the mixture was concentrated in vacuo to give an oily residue. The residue was purified by silica gel column; elution with 50% EtOAc in hexane afforded the desired product CYD-6-19 (20 mg, 42%) as an amorphous gel; [α]$_D^{25}$ +184 (c 0.1, CHCl$_3$); HPLC purity 97.6% (t$_R$=12.4 min); $^1$H NMR (600 MHz, CDCl$_3$): δ 10.62 (br s, 1H), 6.18 (s, 1H), 5.81 (d, 1H, J=12.6 Hz), 5.57 (d, 1H, J=0.6 Hz), 5.24 (br s, 1H), 5.16 (br s, 1H), 4.96 (d, 1H, J=1.2 Hz), 4.72 (s, 1H), 4.36 (dd, 1H, =0.6 Hz, 10.2 Hz), 4.08 (dd, 1H, J=10.2 Hz), 3.79 (m, 1H), 3.03 (d, 1H, J=9.6 Hz), 2.45 (m, 1H), 2.25 (d, 1H, J=15.0 Hz), 2.04 (d, 1H, J=14.4 Hz), 1.99 (m, 2H), 1.92 (s, 3H), 1.66 (d, 1H, J=3.6 Hz), 1.59 (m, 2H), 1.21 (s, 3H), 1.00 (s, 3H). $^{13}$C NMR (150 MHz, CDCl$_3$): δ 206.7, 192.7, 162.0, 151.6, 121.3, 100.6, 98.1, 73.2, 72.0, 66.5, 62.4, 58.4, 51.6, 46.4 (2C), 42.5, 32.9, 30.5, 30.2, 21.7, 20.7, 20.1. MS (+ESI-LR): m/z=418.1 [M+H]$^+$; HRMS calc. for C$_{22}$H$_{27}$NO$_5$S: [M+H]$^+$ 418.1683; found 418.1685.

To a solution of CYD-5-38 (50 mg, 0.11 mmol) in ethanol (4 mL) was added thiourea (12 mg, 0.16 mmol) at room temperature. The reaction mixture was heated under reflux for 3 h. After cooling, the mixture was concentrated in vacuo to give an oily residue. The residue was purified by silica gel column; elution with 51% EtOAc in hexane afforded the desired product CYD-5-41 (25 mg, 53%) as an amorphous gel; [α]$_D^{25}$+190 (c 0.1, CHCl$_3$); HPLC purity 97.0% (t$_R$=9.0 min); $^1$H NMR (600 MHz, CDCl$_3$+CD$_3$OD): δ 6.16 (s, 1H), 5.59 (s, 1H), 5.01 (s, 1H), 4.37 (d, 1H, J=10.2), 3.96 (d, 1H, J=9.6 Hz), 3.80 (d, 1H, J=3.0 Hz), 3.32 (s, 1H), 3.01 (d, 1H, J=3.6 Hz), 2.52 (m, 2H), 2.31 (d, 1H, J=15.6 Hz), 2.12 (m, 1H), 1.94 (dd, 1H, J=4.8 Hz, 13.8 Hz), 1.83 (m, 1H), 1.69 (d, 1H, J=9.0 Hz), 1.58 (m, 1H), 1.25 (s, 3H), 0.99 (s, 3H). $^{13}$C NMR (150 MHz, CDCl$_3$+CD$_3$OD): δ 206.8, 166.0, 151.4, 141.7, 120.4, 120.2, 97.5, 72.7, 72.5, 64.9, 61.9, 59.1, 53.1, 43.2, 40.5, 38.6, 34.6, 30.2, 29.8, 20.2, 20.1. MS (+ESI-LR): m/z =419.1 [M+H]$^+$; HRMS calc. for C$_{21}$H$_{26}$N$_2$O$_5$S: [M+H]$^+$ 419.1635; found 419.1638.

Example 5

(5aR,6S,7S,7aR,10S,12aS,12bR,15R)-6,7,15-trihydroxy-5,5-dimethyl-2-(methylamino)-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-5-54)

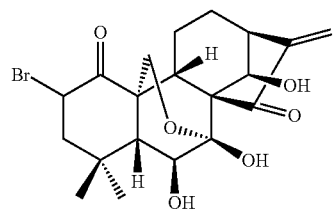

CYD-5-38

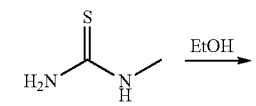

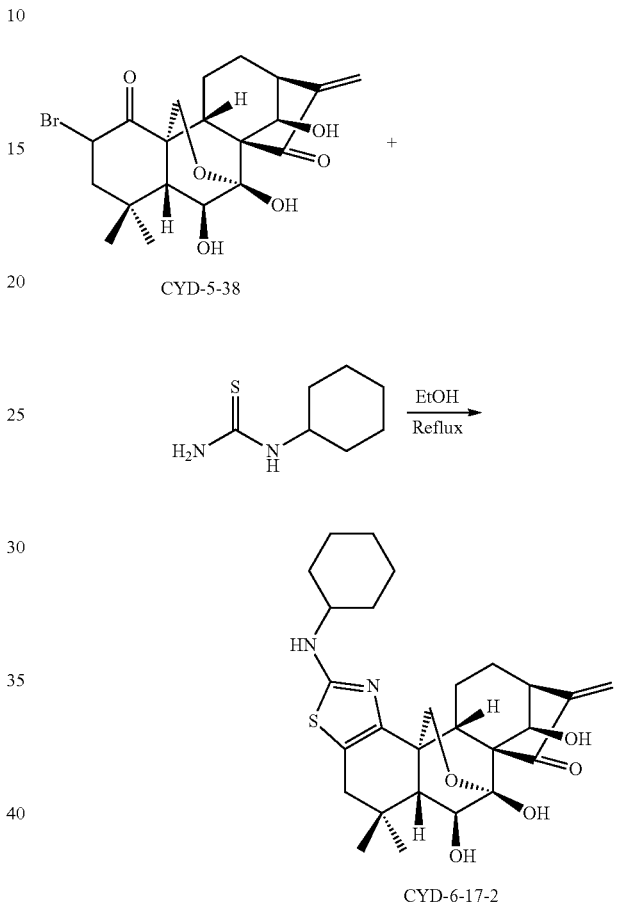

To a solution of CYD-5-38 (50 mg, 0.11 mmol) in ethanol (4 mL) was added 1-methylthiourea (14 mg, 0.16 mmol) at room temperature. The reaction mixture was heated under reflux for 3 h. After cooling, the mixture was concentrated in vacuo to give an oily residue. The residue was purified by silica gel column; elution with 50% EtOAc in hexane afforded the desired product CYD-5-54 (25 mg, 52%) as an amorphous gel; $[\alpha]_D^{25}$+146 (c 0.1, CHCl$_3$); HPLC purity 95.6% ($t_R$=15.7 min); $^1$H NMR (600 MHz, CDCl$_3$): δ 6.80 (br s, 1H), 6.17 (s, 1H), 5.97 (d, 1H, J=12.0 Hz), 5.80 (br s, 1H), 5.56 (s, 1H), 5.03 (br s, 2H), 4.65 (d, 1H, J=10.2 Hz), 3.87 (d, 1H, J=10.2 Hz), 3.77 (dd, 1H, J=9.6 Hz, 12.0 Hz), 3.05 (d, 1H, J=9.0 Hz), 2.86 (s, 3H), 2.50 (m, 2H), 2.32 (d, 1H, J=16.2 Hz), 2.15 (m, 1H), 2.04 (s, 3H), 1.88 (m, 1H), 1.82 (m, 1H), 1.69 (d, 1H, J=9.0 Hz), 1.53 (m, 1H), 1.22 (s, 3H), 0.93 (s, 3H). $^{13}$C NMR (150 MHz, CDCl$_3$+CD$_3$OD): δ 206.7, 168.5, 151.9, 143.1, 120.9, 118.8, 97.9, 73.5, 72.1, 65.1, 62.6, 58.0, 53.2, 42.7, 41.2, 39.0, 35.0, 32.3, 30.5, 30.2, 20.9, 20.4. MS (+ESI-LR): m/z=433.1 [M+H]$^+$; HRMS calc. for C$_{22}$H$_{28}$N$_2$O$_5$S: [M+H]$^+$ 433.1792; found 433.1795.

Example 6

(6S,7S,7aR,10R,12bR,15R)-2-(cyclohexylamino)-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-17-2)

CYD-5-38

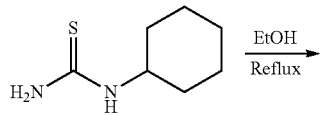

CYD-6-17-2

To a solution of CYD-5-38 (50 mg, 0.11 mmol) in ethanol (4 mL) was added 1-cyclohexylthiourea (25 mg, 0.16 mmol) at room temperature. The reaction mixture was heated under reflux for 3 h. After cooling, the mixture was concentrated in vacuo to give an oily residue. The residue was purified by silica gel column; elution with 50% EtOAc in hexane afforded the desired product CYD-6-17-2 (30 mg, 52%) as amorphous gel; $[\alpha]_D^{25}$+132 (c 0.1, CHCl$_3$); HPLC purity 98.9% ($t_R$=22.2 min); $^1$H NMR (600 MHz, CDCl$_3$): δ 6.84 (br s, 1H), 6.19 (s, 1H), 5.95 (d, 1H, J=12.0 Hz), 5.74 (br s, 1H), 5.58 (s, 1H), 5.04 (s, 2H), 4.67 (m, 1H), 3.89 (d, 1H, J=10.2 Hz), 3.80 (m, 1H), 3.08 (d, 2H, J=9.0 Hz), 2.52 (m, 2H), 2.31 (d, 1H, J=9.6 Hz), 2.19 (m, 1H), 2.07 (m, 1H), 2.02 (m, 1H), 1.89 (dd, 1H, J=4.8 Hz, 13.8 Hz), 1.80 (m, 2H), 1.71 (d, 1H, J=9.0 Hz), 1.65 (d, 1H, J=12.6 Hz), 1.56 (m, 1H), 1.28 (m, 6H), 1.27 (s, 3H), 0.97 (s, 3H). $^{13}$C NMR (150 MHz, CDCl$_3$): δ 206.7, 166.5, 152.0, 142.6, 120.8, 118.1, 97.9, 73.5, 72.1, 65.0, 62.6, 58.1, 55.7, 53.3, 42.7, 41.2, 39.1, 35.0, 32.9, 30.5, 30.2, 29.6, 25.5, 25.0, 21.0, 20.4. MS (+ESI-LR): m/z=501.2 [M+H]$^+$; HRMS calc. for C$_{27}$H$_{36}$N$_2$O$_5$S: [M+H]$^+$ 501.2418; found 501.2423.

Example 7

(5aR,6S,7S,7aR,10S,12aS,12bR,15R)-2-(allylamino)-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-18)

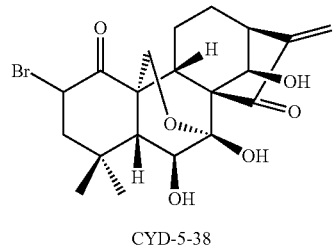

CYD-5-38

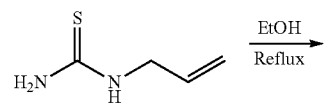

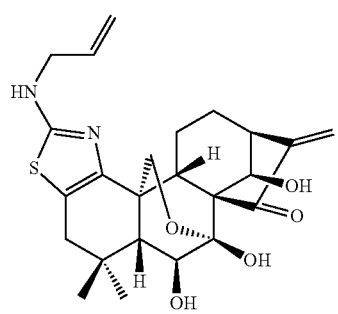

CYD-6-18

To a solution of CYD-5-38 (50 mg, 0.11 mmol) in ethanol (4 mL) was added 1-allylthiourea (18 mg, 0.16 mmol) at room temperature. The reaction mixture was heated under reflux for 3 h. After cooling, the mixture was concentrated in vacuo to give an oily residue. The residue was purified by silica gel column; elution with 50% EtOAc in hexane afforded the desired product CYD-6-18 (20 mg, 38%) as amorphous gel; $[\alpha]_D^{25}$ +85 (c 0.1, CHCl$_3$); HPLC purity 98.5% ($t_R$=11.8 min); $^1$H NMR (600 MHz, CDCl$_3$): δ 6.30 (br s, 1H), 6.17 (s, 1H), 5.98 (d, 1H, J=11.4 Hz), 5.88 (m, 1H), 5.67 (br s, 1H), 5.56 (s, 1H), 5.27 (d, 1H, J=16.8 Hz), 5.18 (d, 1H, J=9.6 Hz), 5.02 (s, 1H), 4.91 (br s, 1H), 4.57 (d, 1H, J=10.2 Hz), 3.91 (d, 1H, J=10.2 Hz), 3.80 (m, 3H), 3.05 (d, 1H, J=9.6 Hz), 2.48 (m, 2H), 2.31 (d, 1H, J=15.6 Hz), 2.13 (m, 1H), 1.86 (m, 2H), 1.69 (d, 1H, J=9.0 Hz), 1.54 (m, 1H), 1.24 (s, 3H), 0.95 (s, 3H). $^{13}$C NMR (150 MHz, CDCl$_3$): δ 206.7, 166.7, 151.8, 142.8, 133.7, 121.0, 119.3, 117.2, 97.9, 73.5, 72.1, 65.2, 62.6, 58.0, 53.2, 48.4, 42.7, 41.1, 39.0, 35.0, 30.5, 30.2, 21.0, 20.4. MS (+ESI-LR): m/z=459.2 [M+H]$^+$; HRMS calc. for C$_{24}$H$_{30}$N$_2$O$_5$S: [M+H]$^+$ 459.1948; found 459.1952.

Example 8

(6S,7S,7aR,10R,12bR,15R)-6,7,15-trihydroxy-5,5-dimethyl-9-methylene-2-((2-(piperidin-1-yl)ethyl)amino)-5,5a,6,7,10,11,12,12a-octahydro-4H-7,12b(epoxymethano)-7a,10-methanocyclohepta[7,8]naphtho[1,2-d]thiazol-8(9H)-one (CYD-6-20)

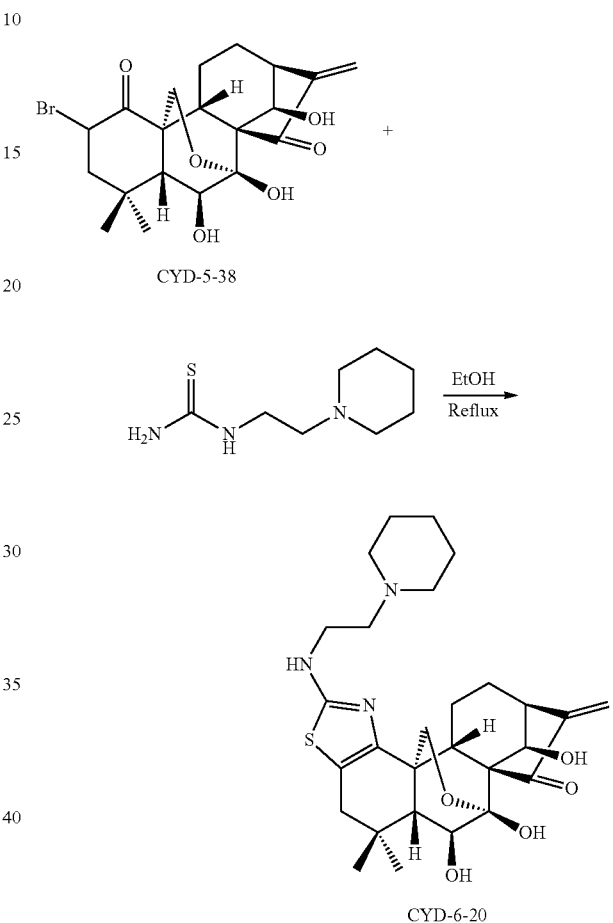

To a solution of CYD-5-38 (50 mg, 0.11 mmol) in ethanol (4 mL) was added 1-(2-(piperidin-1-yl)ethyl) thiourea (30 mg, 0.16 mmol) at room temperature. The reaction mixture was heated under reflux for 3 h. After cooling, the mixture was concentrated in vacuo to give an oily residue. The residue was purified by silica gel column; elution with 5% MeOH in CH$_2$Cl$_2$ afforded the desired product CYD-6-20 (3 lmg, 51%) as an amorphous gel; $[\alpha]_D^{25}$ +138 (c 0.1, CHCl$_3$); HPLC purity 98.5% ($t_R$=10.5 min); $^1$H NMR (600 MHz, CDCl$_3$): δ 6.18 (s, 1H), 6.06 (d, 1H, J=12.0 Hz), 5.74 (br s, 1H), 5.57 (s, 1H), 5.03 (s, 1H), 4.47 (d, 1H, J=10.2 Hz), 3.99 (d, 1H, J=10.2 Hz), 3.85 (dd, 1H, J=9.0 Hz, 12.0 Hz), 3.26 (t, 2H, J=5.4 Hz), 3.05 (d, 1H, J=9.6 Hz), 2.57 (m, 2H), 2.48 (m, 6H), 2.33 (d, 1H, J=15.6 Hz), 2.14 (m, 1H), 1.92 (m, 2H), 1.71 (d, 1H, J=8.4 Hz), 1.59 (m, 5H), 1.46 (m, 2H), 1.27 (s, 3H), 0.99 (s, 3H). $^{13}$C NMR (150 MHz, CDCl$_3$): δ 206.7, 166.1, 151.8, 143.0, 120.9, 119.1, 97.8, 73.5, 72.2, 65.6, 62.6, 58.1, 57.2, 54.4 (2C), 53.2, 42.8, 42.1, 41.0, 39.0, 35.0, 30.5, 30.3, 25.6 (2C), 24.2, 21.0, 20.3. MS (+ESI-LR): m/z=530.2 [M+H]$^+$; HRMS calc. for C$_{28}$H$_{39}$N$_3$O$_5$S: [M+H]$^+$ 530.2683; found 530.2687.

Example 9

N-((6S,7S,7aR,10R,12bR,15R)-6,7,15-trihydroxy-5,5-dimethyl-9-methylene-8-oxo-5,5a,6,7,8,9,10,11,12,12a-decahydro-4H-7,12b-(epoxymethano)-7a,10-methanocyclohepta[7,8]naphtho[1,2-d]thiazol-2-yl)acetamide (CYD-6-21)

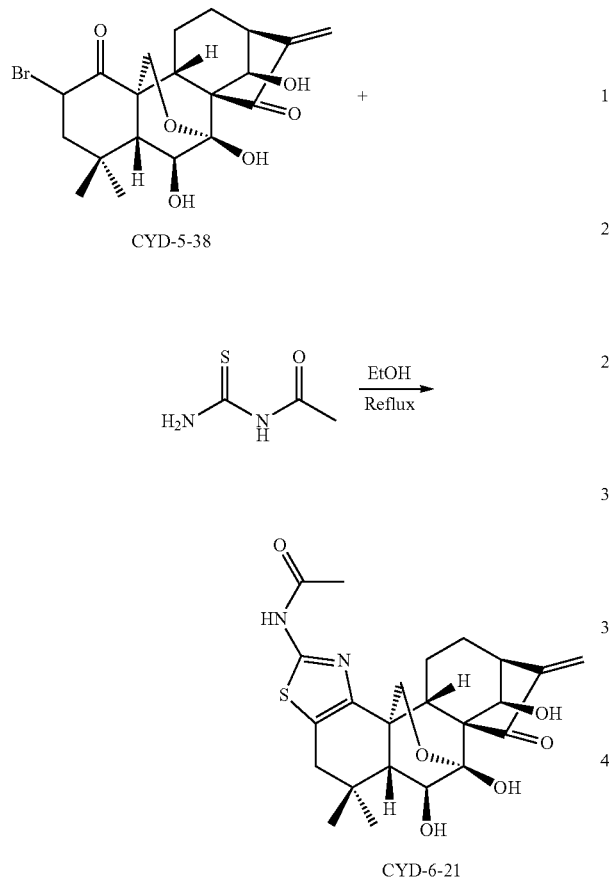

To a solution of CYD-5-38 (50 mg, 0.11 mmol) in ethanol (4 mL) was added acetyl-thiourea (19 mg, 0.16 mmol) at room temperature. The reaction mixture was heated under reflux for 3 h. After cooling, the mixture was concentrated in vacuo to give an oily residue. The residue was purified by silica gel column; elution with 50% EtOAc in hexane afforded the desired product CYD-6-21 (19 mg, 36%) as an amorphous gel; $[\alpha]_D^{25}$+152 (c 0.1, CHCl$_3$); HPLC purity 99.2% ($t_R$=13.5 min); $^1$H NMR (600 MHz, CDCl$_3$): δ 10.29 (s, 1H), 7.96 (br s, 1H), 6.23 (d, 1H, J=12.6 Hz), 6.22 (s, 1H), 5.63 (s, 1H), 5.17 (s, 1H), 5.09 (s, 1H), 4.96 (d, 1H, J=10.2 Hz), 3.76 (m, 2H), 3.12 (d, 1H, J=9.6 Hz), 2.56 (m, 2H), 2.45 (d, 1H, J=15.6 Hz), 2.30 (s, 3H), 2.24 (m, 1H), 1.93 (dd, 1H, J=3.6 Hz, 13.8 Hz), 1.79 (d, 1H, J=9.0 Hz), 1.73 (br s, 1H), 1.57 (m, 2H), 1.26 (s, 3H), 0.82 (s, 3H). $^{13}$C NMR (150 MHz, CDCl$_3$): δ 206.8, 168.9, 156.6, 151.5, 140.8, 125.9, 121.7, 98.0, 73.8, 72.0, 64.4, 62.4, 58.1, 52.9, 42.6, 41.0, 38.6, 34.9, 30.4, 29.9, 23.0, 20.7, 20.6. MS (+ESI-LR): m/z=461.1 [M+H]$^+$; HRMS calc. for C$_{23}$H$_{28}$N$_2$O$_6$S: [M+H]$^+$ 461.1741; found 461.1747.

Example 10

(6S,7S,7aR,10R,12bR,15R)-2-(azepan-1-yl)-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-26-2)

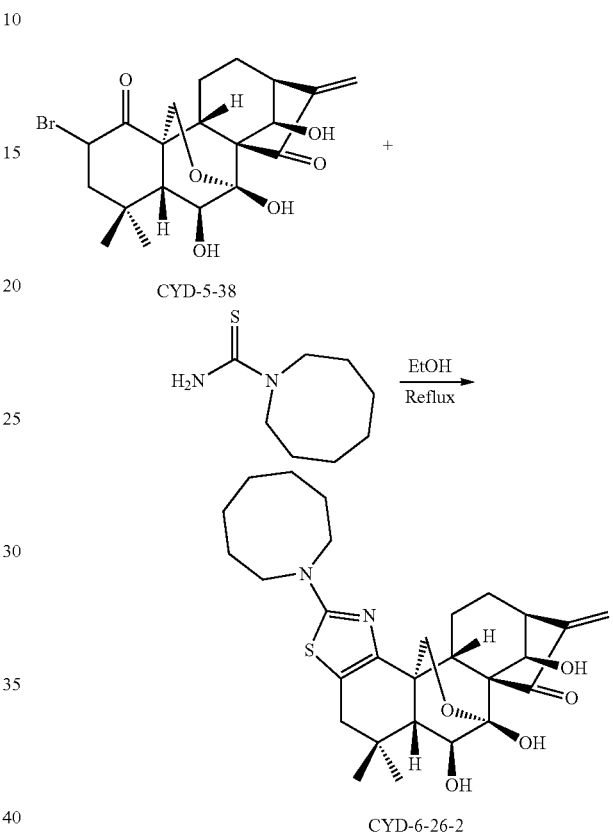

To a solution of CYD-5-38 (50 mg, 0.11 mmol) in ethanol (4 mL) was added azepane-1-carbothioamide (25 mg, 0.16 mmol) at room temperature. The reaction mixture was heated under reflux for 3 h. After cooling, the mixture was concentrated in vacuo to give an oily residue. The residue was purified by silica gel column; elution with 50% EtOAc in hexane afforded the desired product CYD-6-26-2 (24 mg, 41%) as an amorphous gel; $[\alpha]_D^{25}$+148 (c 0.1, CHCl$_3$); HPLC purity 97.8% ($t_R$=24.3 min); $^1$H NMR (600 MHz, CDCl$_3$): δ 6.17 (s, 1H), 6.05 (d, 1H, J=12.0 Hz), 5.56 (s, 1H), 5.18 (br s, 1H), 5.01 (d, 1H, J=1.2 Hz), 4.71 (s, 1H), 4.44 (dd, 1H, J=1.2 Hz, 10.2 Hz), 4.00 (dd, 1H, J=10.2 Hz), 3.86 (dd, 1H, J=9.0 Hz, 12.0 Hz), 3.49 (m, 2H), 3.39 (m, 2H), 3.04 (d, 1H, J=9.6 Hz), 3.48 (m, 2H), 2.32 (d, 1H, J=15.6 Hz), 2.05 (m, 2H), 1.91 (m, 1H), 1.72 (m, 6H), 1.55 (m, 5H), 1.25 (s, 3H), 0.99 (s, 3H). $^{13}$C NMR (150 MHz, CDCl$_3$): δ 206.7, 166.3, 151.7, 143.3, 121.1, 117.6, 97.8, 73.6, 72.2, 65.8, 62.7, 57.6, 53.2, 50.2 (2C), 42.7, 40.9, 38.8, 35.0, 30.4, 29.6, 27.9 (2C), 27.7 (2C), 21.1, 20.2. MS (+ESI-LR): m/z=501.2 [M+H]$^+$; HRMS calc. for C$_{27}$H$_{36}$N$_2$O$_5$S: [M+H]$^+$ 501.2418; found 501.2422.

Example 11

(5aR,6S,7S,7aR,10S,12a5,12bR,15R)-2-(butylamino)-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(91/)-one (CYD-6-28)

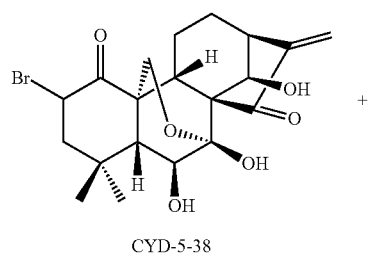

CYD-5-38

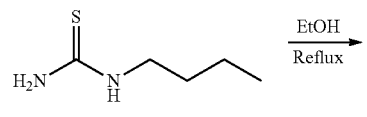

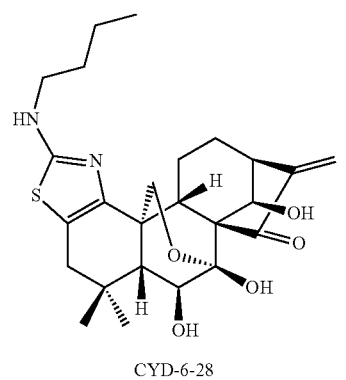

CYD-6-28

To a solution of CYD-5-38 (50 mg, 0.11 mmol) in ethanol (4 mL) was added 1-butylthiourea (21 mg, 0.16 mmol) at room temperature. The reaction mixture was heated under reflux for 3 h. After cooling, the mixture was concentrated in vacuo to give an oily residue. The residue was purified by silica gel column; elution with 50% EtOAc in hexane afforded the desired product CYD-6-28 (28 mg, 48%) as an amorphous gel; $[\alpha]_D^{25}$+142 (c 0.1, CHCl$_3$); HPLC purity 98.0% ($t_R$=13.7 min); $^1$H NMR (600 MHz, CDCl$_3$): δ 6.80 (br s, 1H), 6.17 (s, 1H), 5.94 (d, 1H, J=12.0 Hz), 5.74 (br s, 1H), 5.56 (s, 1H), 5.02 (s, 1H), 4.64 (d, 1H, J=10.2 Hz), 3.88 (d, 1H, J=10.2 Hz), 3.78 (m, 1H), 3.10 (d, 1H, J=4.2 Hz), 3.05 (d, 1H, J=9.0 Hz), 2.50 (m, 2H), 2.31 (d, 1H, J=16.2 Hz), 2.15 (m, 1H), 1.88 (dd, 1H, J=4.8 Hz, 13.8 Hz), 1.81 (m, 1H), 1.69 (d, 1H, J=9.6 Hz), 1.61 (m, 2H), 1.54 (m, 1H), 1.39 (m, 2H), 1.24 (s, 3H), 0.93 (m, 6H). $^{13}$C NMR (150 MHz, CDCl$_3$): δ 206.8, 167.6, 151.9, 142.8, 120.9, 118.4, 97.9, 73.5, 72.1, 65.1, 62.6, 58.1, 53.3, 46.2, 42.7, 41.2, 39.0, 35.0, 31.3, 30.5, 30.2, 20.9, 20.5, 20.1, 13.8. MS (+ESI-LR): m/z=475.2 [M+H]$^+$; HRMS calc. for C$_{25}$H$_{34}$N$_2$O$_5$S: [M+H]$^+$ 475.2261; found 475.2264.

Example 12

1-((5aR,6S,7S,7aR,10S,12aS,12bR,15R)-6,7,15-trihydroxy-5,5-dimethyl-9-methylene-8-oxo-5,5a,6,7,8,9,10,11,12,12a-decahydro-4H-7,12b-(epoxymethano)-7a,10-methanocyclohepta[7,8]naphtho[1,2-d]thiazol-2-yl)guanidine (CYD-6-29)

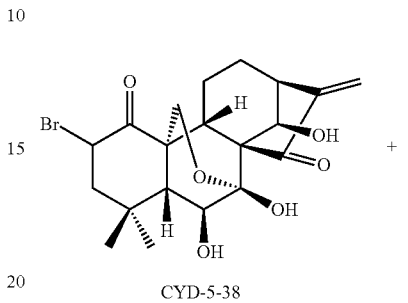

CYD-5-38

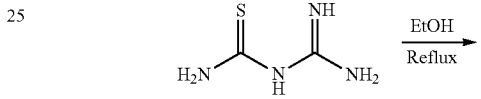

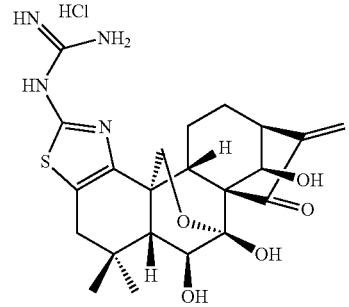

CYD-6-29

To a solution of CYD-5-38 (50 mg, 0.11 mmol) in ethanol (4 mL) was added amidinothiourea (19 mg, 0.16 mmol) at room temperature. The reaction mixture was heated under reflux for 3 h. After cooling, the mixture was acidified with 5% HCll aqueous solution, and concentrated in vacuo to give an oily residue. The residue was purified by silica gel column; elution with 5% MeOH in CH$_2$Cl$_2$ afforded the desired product CYD-6-29 (28 mg, 50%) as a colorless solid; $[\alpha]_D^{25}$+108 (c 0.1, CHCl$_3$/CH$_3$OH=4:1); HPLC purity 95.1% ($t_R$=5.7 min); $^1$H NMR (600 MHz,CD$_3$OD+CDCl$_3$): δ 6.19 (s, 1H), 5.62 (s, 1H), 5.06 (s, 1H), 4.44 (d, 1H, J=9.6 Hz), 4.00 (d, 1H, J=9.0 Hz), 3.85 (d, 1H, J=8.4 Hz), 3.05 (d, 1H, J=9.0 Hz), 2.66 (d, 1H, J=16.2 Hz), 2.55 (m, 2H), 2.24 (m, 1H), 2.09 (dd, 1H, J=4.8 Hz, 13.2 Hz), 1.81 (d, 1H, J=8.4 Hz), 1.72 (m, 1H), 1.62 (m, 1H), 1.30 (s, 3H), 1.01 (s, 3H). $^{13}$C NMR (150 MHz, CDCl$_3$): δ 206.7, 156.5, 154.4, 151.1, 142.9, 126.6, 120.9, 97.5, 72.5, 64.8, 61.7, 58.8, 52.5, 43.1, 40.2, 38.0, 34.7, 30.0, 29.7, 29.3, 20.1, 19.6. MS (+ESI-LR): m/z=461.1 [M+H]$^+$; HRMS calc. for C$_{22}$H$_{28}$N$_4$O$_5$S: [M+H]$^+$ 461.1853; found 461.1856.

Example 13

(5aR,6S,7S,7aR,10S,12a5,12bR,15R)-6,7,15-trihydroxy-2-(isopropylamino)-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-30)

Example 14

(3S,3aR,3a¹R,6aR,7S,7aR,11aS,11bS)-7-hydroxy-5,5,8,8-tetramethyl-15-methylene-3,3a,7,7a,8,11b-hexahydro-1H-6a,11a-(epoxymethano)-3,3a¹-ethanophenanthro[1,10-de] [1,3]dioxine-11,14(2H)-dione (CYD-6-25)

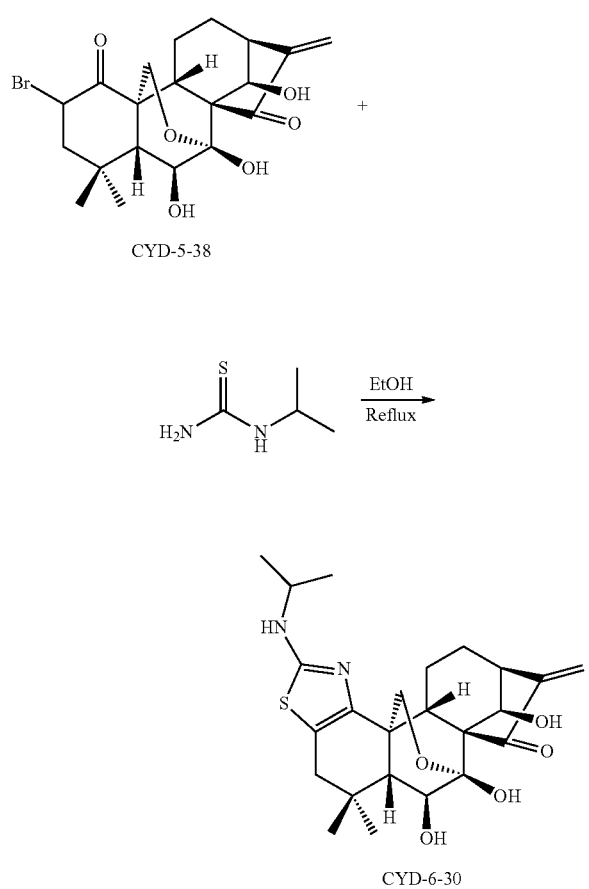

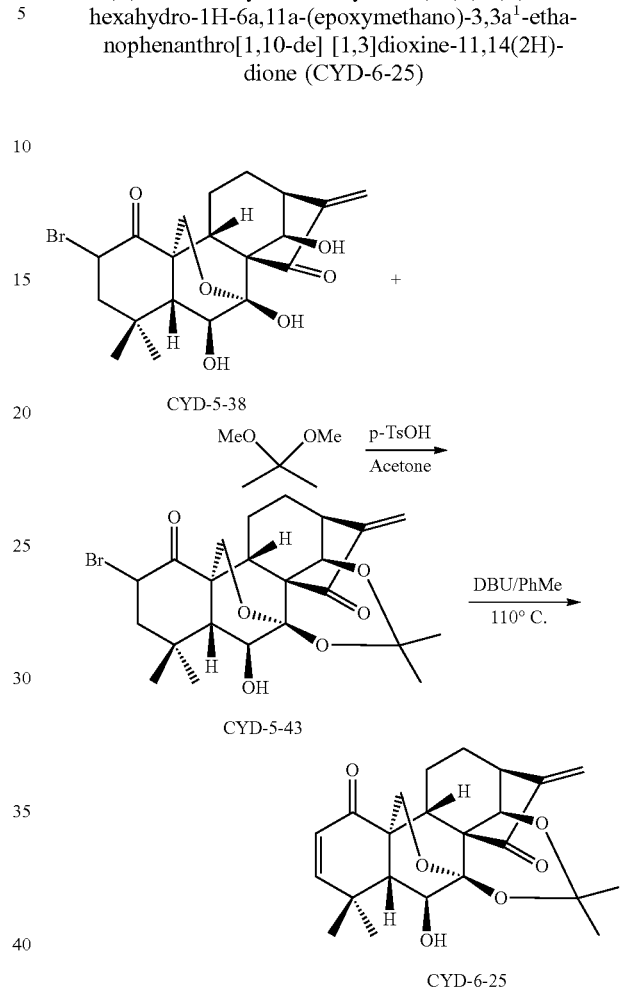

To a solution of CYD-5-38 (50 mg, 0.11 mmol) in ethanol (4 mL) was added 1-isopropylthiourea (19 mg, 0.16 mmol) at room temperature. The reaction mixture was heated under reflux for 3 h. After cooling, the mixture was concentrated in vacuo to give an oily residue. The residue was purified by silica gel column; elution with 50% EtOAc in hexane afforded the desired product CYD-6-30 (23 mg, 44%) as amorphous gel; $[\alpha]_D^{25}$+161 (c 0.1, CHCl$_3$); HPLC purity 98.0% ($t_R$=12.3 min); $^1$H NMR (600 MHz, CDCl$_3$): δ 6.64 (br s, 1H), 6.17 (s, 1H), 5.93 (d, 1H, J=12.6 Hz), 5.56 (s, 2H), 5.02 (s, 2H), 4.64 (d, 1H, J=10.2 Hz), 3.89 (d, 1H, J=10.2 Hz), 3.79 (dd, 1H, J=9.6 Hz), 3.47 (m, 1H), 3.06 (d, 1H, J=9.6 Hz), 2.50 (m, 2H), 2.30 (d, 1H, J=16.2 Hz), 2.15 (m, 1H), 1.88 (m, 1H), 1.83 (m, 1H), 1.69 (d, 1H, J=9.6 Hz), 1.53 (m, 1H), 1.25 (s, 3H), 1.24 (s, 3H), 1.23 (s, 3H), 0.95 (s, 3H). $^{13}$C NMR (150 MHz, CDCl$_3$): δ 206.7, 166.3, 151.9, 142.6, 120.9, 118.4, 97.9, 73.5, 72.1, 65.1, 62.6, 58.0, 53.3, 48.2, 42.7, 41.2, 39.0, 35.0, 30.6, 30.2, 22.8, 22.6, 21.0, 20.5. MS (+ESI-LR): m/z=461.2 [M+H]$^+$; HRMS calc. for C$_{24}$H$_{32}$N$_2$O$_5$S: [M+H]$^+$ 461.2105; found 461.2111.

To a solution of CYD-5-38 (80 mg, 0.18 mmol) in acetone (4 mL) was added TsOH (5 mg) and 2,2-dimethoxypropane (0.32 mL) at rt. The resulting mixture was stirred at rt for 2 hrs. After that, the reaction mixture was diluted with water and extracted with dichloromethane. The extract was washed with saturated NaHCO$_3$ solution and brine, dried over anhydrous Na$_2$SO$_4$, filtered, and evaporated to afford compound CYD-5-43 (83 mg, 95%) as a colorless gel. To a solution of CYD-5-43 (50 mg, 0.10 mmol) in toluene (5 mL) was added DBU (20 mg, 0.13 mmol) at rt. The resulting mixture was stirred at 110° C. for 4 hrs, and diluted with water and extracted with EtOAc. The organic extract was washed with 3 N HCl aqueous solution and brine, dried over anhydrous Na$_2$SO$_4$, filtered, and evaporated to give an oily residue, which was purified using preparative TLC developed by 30% EtOAc in hexane to afford the desired product CYD-6-25 as a colorless amorphous gel (30 mg, 72%). HPLC purity 98.7% ($t_R$=19.78 min). $^1$H NMR (600 MHz, CDCl$_3$) δ 6.80 (d, 1H, J=9.6 Hz), 6.17 (s, 1H), 5.84 (d, 1H, J=10.2 Hz), 5.59 (s, 1H), 5.41 (d, 1H, J=12.0 Hz), 4.88 (s, 1H), 4.24 (dd, 1H, J=1.2 Hz, 10.2 Hz), 4.08 (m, 2H), 3.08 (d, 1H, J=9.0 Hz), 2.53 (m, 1H), 2.00 (m, 3H), 1.67 (s, 3H), 1.62 (m, 3H), 1.42 (s, 3H), 1.36 (s, 3H), 1.27 (s, 3H). $^{13}$C NMR (150 MHz, CDCl$_3$) δ 204.7, 196.5, 162.1, 150.4, 126.6, 120.8, 101.3, 95.7, 71.7, 69.9, 65.1, 56.5, 55.9, 47.4, 45.8, 40.1, 35.9, 30.4, 30.2, 30.1, 25.4, 25.0, 19.3. HRMS Calcd for $C_{23}H_{29}O_6$: [M+H]$^+$ 401.1959; found 401.1957.

Example 15

(4aR,5S,6S,6aR,9S,11aS,11bS,14R)-5,6,14-trihydroxy-4,4-dimethyl-8-methylene-4,4a,5,6,9,10,11,11a-octahydro-1H-6,11b-(epoxymethano)-6a,9-methanocyclohepta[α]naphthalene-1,7(8H)-dione (CYD-6-58)

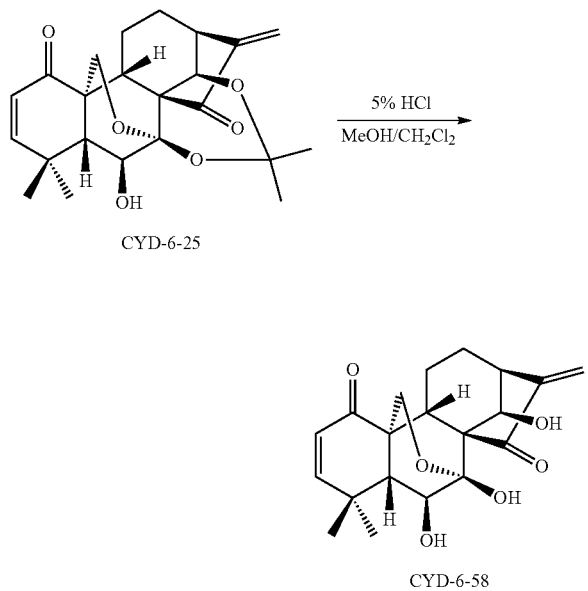

To a solution of CYD-6-25 (8.0 mg, 0.02 mmol) in a mixture of MeOH (2 mL) and $CH_2Cl_2$ (0.5 mL) was added 5% HCl aqueous solution (0.5 mL) at rt. The resulting mixture was stirred at rt for 4 hrs. After that, the reaction mixture was diluted with water and extracted with dichloromethane. The extract was washed with saturated $NaHCO_3$ (aq.) solution and brine, dried over anhydrous $Na_2SO_4$, filtered, and evaporated to give an oily residue. The residue was purified using preparative TLC developed by 50% EtOAc in hexane to afford the desired product CYD-6-58 as a colorless amorphous gel (5.0 mg, 69%). HPLC purity 99.0% ($t_R$=16.02 min). $^1$H NMR (600 MHz, $CDCl_3$+$CD_3OD$) δ 6.88 (d, 1H, J=9.6 Hz), 6.21 (s, 1H), 5.87 (d, 1H, J=10.2 Hz), 5.63 (s, 1H), 4.97 (s, 1H), 4.27 (m, 2H), 4.06 (dd, 1H, J=1.2 Hz, 10.2 Hz), 3.96 (d, 1H, J=8.4 Hz), 3.04 (d, 1H, J=9.6 Hz), 2.52 (m, 1H), 2.10 (m, 2H), 2.03 (d, 1H, J=8.4 Hz), 1.62 (m, 1H), 1.48 (m, 1H), 1.39 (s, 3H), 1.27 (s, 3H). $^{13}$C NMR (150 MHz, $CDCl_3$+$CD_3OD$) δ 206.7, 197.3, 161.8, 150.8, 126.8, 121.2, 97.9, 72.3, 72.2, 65.2, 61.4, 56.8, 50.0, 45.9, 42.7, 35.7, 29.8, 29.4, 23.9, 18.9; HRMS Calcd for $C_{20}H_{25}O_6$: [M+H]$^+$ 361.1646; found 361.1544.

Example 16

(3S,3aR,3a$^1$R,6aR,7S,7aR,11S,11aS,11bS)-7-hydroxy-5,5,8,8-tetramethyl-15-methylene-14-oxo-decahydro-1H-6a,11a-(epoxymethano)-3,3a$^1$-ethanophenanthro[1,10-de][1,3]dioxin-11-yl methanesulfonate (CYD-5-61)

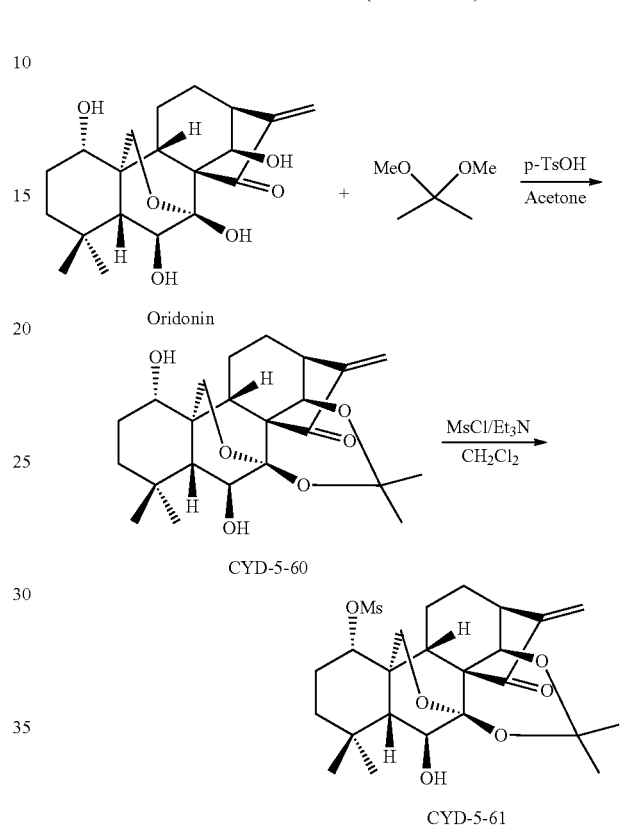

To a solution of oridonin (500 mg, 1.36 mmol) in acetone (20 mL) was added TsOH (20 mg) and 2,2-dimethoxypropane (3.0 mL) at rt. The resulting mixture was stirred at rt for 2 hrs. After that, the reaction mixture was diluted with water and extracted with dichloromethane. The extract was washed with saturated $NaHCO_3$ (aq.) solution and brine, dried over anhydrous $Na_2SO_4$, filtered, and evaporated to afford compound CYD-5-60 as a colorless gel (520 mg, 93%). To a solution of CYD-5-60 (277 mg, 0.68 mmol) in dichloromethane was added $Et_3N$ (138 mg, 1.37 mmol) and MsCl (94 mg, 0.82 mmol) slowly at 0° C. The mixture was stirred at rt overnight, and diluted with water and extracted with dichloromethane. The organic extract was washed with saturated $NaHCO_3$ (aq.) solution and brine, dried over anhydrous $Na_2SO_4$, filtered, and evaporated to give an oily residue. The crude residue was further purified by silica gel column; elution with 50% EtOAc in hexane afforded the desired product CYD-5-61 as a colorless gel (264 mg, 80%). $^1$H NMR (600 MHz, $CDCl_3$) δ 6.16 (s, 1H), 5.82 (d, 1H, J=12.0 Hz), 5.58 (s, 1H), 4.76 (dd, 1H, J=6.0 Hz, 12.0 Hz), 4.14 (d, 1H, J=4.2 Hz), 3.92 (m, 1H), 3.07 (d, 1H, J=9.0 Hz), 2.99 (s, 3H), 2.51 (m, 1H), 2.05 (m, 1H), 1.89 (m, 2H), 1.77 (m, 3H), 1.63 (s, 3H), 1.52 (m, 1H), 1.38 (d, 1H, J=7.2 Hz), 1.33 (s, 3H), 1.19 (s, 3H), 1.18 (s, 3H), 1.16 (d, 1H, J=7.2 Hz). $^{13}$C NMR (150 MHz, $CDCl_3$) δ 205.1, 150.4, 120.5, 101.0, 94.6, 84.7, 72.9, 69.9, 62.3, 59.5, 55.9, 50.0, 40.6, 40.1, 38.2, 33.2, 33.0, 31.5, 30.1 (2C), 26.4, 25.4, 22.4, 18.8; HRMS Calcd for $C_{24}H_{35}O_8S$: $[M+H]^+$ 483.2047; found 483.2052.

Example 17

(3S,3aR,3a¹R,6aR,7S,7aR,11aR,11bS)-7-hydroxy-5,5,8,8-tetramethyl-15-methylene-2,3,3 a,7,7a,8,9,11b-octahydro-1H-6a,11a-(epoxymethano)-3,3a¹-ethanophenanthro[1,10-de] [1,3]dioxin-14-one (CYD-6-75)

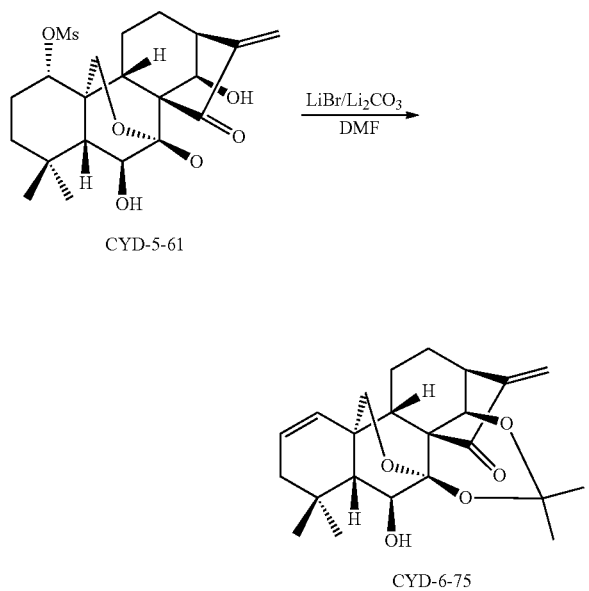

To a solution of CYD-5-61 (34 mg, 0.07 mmol) in DMF (5 mL) was added LiBr (18 mg, 0.21 mmol) and $Li_2CO_3$ (15 mg, 0.21 mmol) at rt. The resulting mixture was stirred at 115° C. for 2 hrs. After that, the reaction mixture was diluted with water and extracted with EtOAc. The organic extract was washed with saturated $NaHCO_3$ (aq.) solution and brine, dried over anhydrous $Na_2SO_4$, filtered, and evaporated to give an oily residue. The crude residue was further purified by silica gel column; elution with 25% EtOAc in hexane afforded the desired product CYD-5-75 as a colorless gel (25 mg, 84%). HPLC purity 99.8% ($t_R$=18.30 min). ¹H NMR (600 MHz, $CDCl_3$) δ 6.16 (s, 1H), 5.77 (m, 1H), 5.56 (s, 1H), 5.41 (d, 1H, J=12.0 Hz), 5.19 (dd, 1H, J=3.0 Hz, 10.2 Hz), 4.82 (s, 1H), 3.99 (d, 1H, J=10.2 Hz), 3.90 (dd, 1H, J=8.4 Hz, 12.0 Hz), 3.81 (d, 1H, J=9.6 Hz), 3.06 (d, 1H, J=9.0 Hz), 2.53 (m, 1H), 1.95 (d, 1H, J=17.4 Hz), 1.76 (m, 4H), 1.65 (s, 3H), 1.56 (m, 1H), 1.50 (d, 1H, J=8.4 Hz), 1.35 (s, 3H), 1.18 (s, 3H), 1.05 (s, 3H). ¹³C NMR (150 MHz, $CDCl_3$) δ 204.5, 150.5, 130.3, 124.1, 120.4, 101.2, 95.4, 72.0, 70.1, 64.8, 57.9, 56.3, 49.1, 41.1, 40.3, 38.1, 32.2, 31.1, 30.3, 30.1, 25.5, 22.1, 17.3. HRMS Calcd for $C_{23}H_{31}O_5$: $[M+H]^+$ 387.2166; found 387.2169.

Example 18

(4aR,5S,6S,6aR,9S,11aS,11bR,14R)-5,6,14-trihydroxy-4,4-dimethyl-8-methylene-4,4a,5,6,9,10,11,11a-octahydro-3H-6,11b-(epoxymethano)-6a,9-methanocyclohepta[α]naphthalen-7(8H)-one (CYD-6-82)

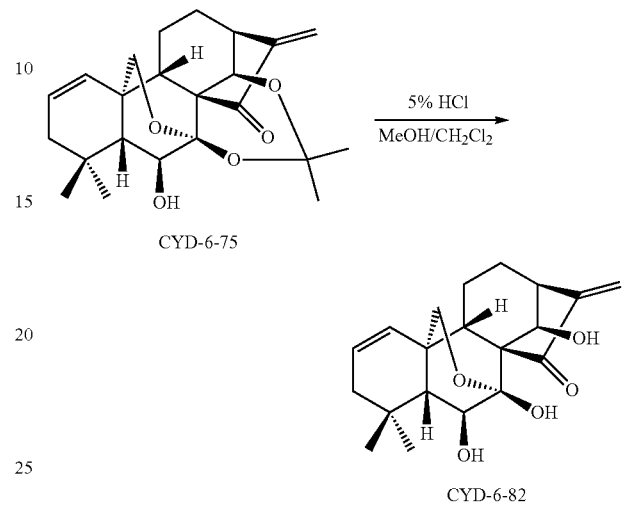

To a solution of CYD-6-75 (9.0 mg, 0.02 mmol) in a mixture of MeOH (2 mL) and $CH_2Cl_2$ (0.5 mL) was added 5% HCl aqueous solution (0.5 mL) at rt. The resulting mixture was stirred at rt for 4 hrs. After that, the reaction mixture was diluted with water and extracted with dichloromethane. The extract was washed with saturated $NaHCO_3$ (aq.) solution and brine, dried over anhydrous $Na_2SO_4$, filtered, and evaporated to give an oily residue. The residue was purified using preparative TLC developed by 50% EtOAc in hexane to give the desired product CYD-6-82 as a colorless gel (6.0 mg, 75%). HPLC purity 98.5% ($t_R$=18.30 min). ¹H NMR (600 MHz, $CDCl_3$) δ 6.22 (s, 1H), 6.01 (d, 1H, J=12.0 Hz), 5.81 (m, 1H), 5.61 (s, 1H), 5.23 (dd, 1H, J=3.0 Hz, 10.2 Hz), 4.92 (s, 1H), 4.03 (d, 1H, J=10.2 Hz), 3.85 (m, 2H), 3.08 (d, 1H, J=9.0 Hz), 2.51 (m, 1H), 1.97 (d, 1H, J=18.0 Hz), 1.85 (m, 3H), 1.68 (m, 1H), 1.59 (m, 1H), 1.54 (d, 1H, J=9.0 Hz), 1.18 (s, 3H), 1.07 (s, 3H). ¹³C NMR (150 MHz, $CDCl_3$) δ 206.3, 151.3, 130.6, 124.4, 121.3, 97.7, 73.6, 72.0, 65.5, 62.2, 57.3, 52.2, 42.5, 40.9, 38.6, 32.3, 30.7, 29.8, 21.7, 17.6; HRMS Calcd for $C_{20}H_{27}O_5$: $[M+H]^+$ 347.1853; found 347.1857.

Example 19

(3S,3aR,3a¹R,6aR,7S,7aS,9S,11aR,11bS)-7,9-dihydroxy-5,5,8,8-tetramethyl-15-methylene-2,3,3a,7,7a,8,9,11b-octahydro-1H-6a,11a-(epoxymethano)-3,3a¹-ethanophenanthro[1,10-de] [1,3]dioxin-14-one (CYD-6-81)

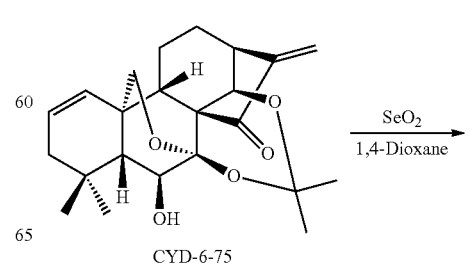

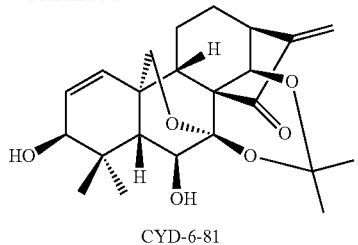

CYD-6-81

A mixture of CYD-6-75 (20 mg, 0.05 mmol) and SeO$_2$ (16 mg, 0.15 mmol) in 1,4-dioxane (4 mL) was stirred at 100° C. for 16 hrs. After that, the reaction mixture was filtered, and the filtrate was diluted with water and extracted with dichloromethane. The extract was washed with brine, dried over anhydrous Na$_2$SO$_4$, filtered, and evaporated to give an oily residue. The residue was purified using preparative TLC developed by 50% EtOAc in hexane to afford the desired product CYD-6-81 as a colorless gel (16 mg, 76%). HPLC purity 99.7% (t$_R$=17.31 min). $^1$H NMR (600 MHz, CDCl$_3$) δ 6.16 (s, 1H), 6.00 (dd, 1H, J=6.0 Hz, 10.2 Hz), 5.56 (s, 1H), 5.42 (m, 2H), 4.82 (s, 1H), 3.94 (m, 2H), 3.84 (d, 1H, J=9.6 Hz), 3.06 (d, 1H, J=9.6 Hz), 2.53 (m, 1H), 1.87 (d, 1H, J=9.0 Hz), 1.82 (m, 2H), 1.71 (m, 2H), 1.65 (s, 3H), 1.57 (m, 1H), 1.35 (s, 1H), 1.24 (s, 3H), 1.01 (s, 3H). $^{13}$C NMR (150 MHz, CDCl$_3$) δ 204.1, 150.3, 130.9, 128.6, 120.6, 101.2, 95.5, 72.6, 71.5, 70.0, 64.5, 56.1, 51.0, 48.8, 40.3, 38.2, 36.7, 30.2, 30.1, 25.9, 25.4, 21.9, 17.3. HRMS Calcd for C$_{23}$H$_{31}$O$_6$: [M+H]$^+$ 403.2115; found 403.2118.

Example 20

(3S,4aS,5S,6S,6aR,9S,11aS,11bR,14R)-3,5,6,14-tetrahydroxy-4,4-dimethyl-8-methylene-4,4a,5,6,9,10,11,11a-octahydro-3H-6,11b-(epoxymethano)-6a,9-methanocyclohepta[α]naphthalen-7(8H)-one (CYD-6-90)

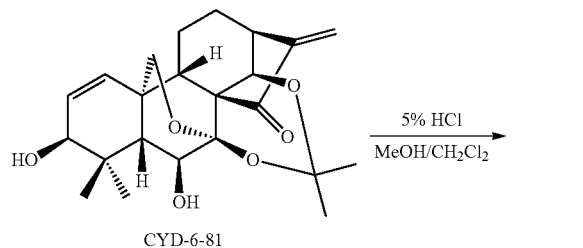

CYD-6-81

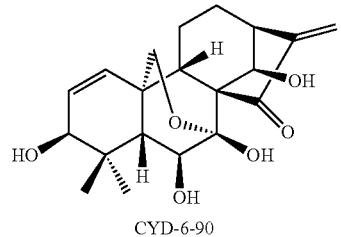

CYD-6-90

To a solution of CYD-6-81 (10 mg, 0.025 mmol) in a mixture of MeOH (2 mL) and CH$_2$Cl$_2$ (0.5 mL) was added 5% HCl aqueous solution (0.5 mL) at rt. The resulting mixture was stirred at rt for 4 hrs. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to give an oily residue. The residue was further purified using preparative TLC developed by 66% EtOAc in hexane to afford the desired product CYD-6-90 as a colorless gel (8.0 mg, 88%). HPLC purity 98.6% (t$_R$=13.17 min). $^1$H NMR (600 MHz, CDCl$_3$) δ 6.19 (s, 1H), 6.02 (dd, 1H, J=6.0 Hz, 10.2 Hz), 5.99 (d, 1H, J=12.0 Hz), 5.58 (s, 1H), 5.42 (d, 1H, J=10.2 Hz), 5.25 (br s, 1H), 4.89 (s, 1H), 4.61 (s, 1H), 3.96 (d, 1H, J=9.6 Hz), 3.85 (m, 2H), 3.65 (d, 1H, J=6.0 Hz), 3.05 (d, 1H, J=9.0 Hz), 2.48 (m, 1H), 1.90 (d, 1H, J=9.0 Hz), 1.84 (m, 2H), 1.67 (m, 2H), 1.55 (m, 1H), 1.21 (s, 3H), 1.00 (s, 3H). $^{13}$C NMR (150 MHz, CDCl$_3$) δ 206.0, 151.0, 131.2, 128.8, 121.6, 97.8, 73.1, 72.3, 72.0, 65.3, 62.0, 51.9, 50.5, 42.5, 38.7, 36.7, 29.7, 25.6, 21.6, 17.6; HRMS Calcd for C$_{20}$H$_{27}$O$_6$: [M+H]$^+$ 363.1802; found 363.1803.

Example 21

(3S,3aR,3a$^1$R,6aR,7S,7aS,11aR,11bS)-7-hydroxy-5,5,8,8-tetramethyl-15-methylene-3,3a,7,7a,8,11b-hexahydro-1H-6a,11a-(epoxymethano)-3,3a$^1$-ethanophenanthro[1,10-de][1,3]dioxine-9,14(2H)-dione (CYD-6-86)

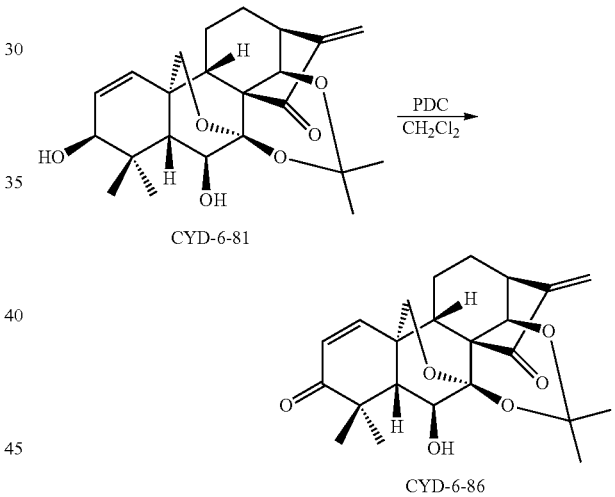

CYD-6-81

CYD-6-86

To a solution if CYD-6-81 (10 mg, 0.025 mmol) in dichloromethane (2 mL) was added PDC (11.2 mg, 0.03 mmol) at rt. The resulting mixture was stirred at rt for 4 hrs. After that, the reaction mixture was filtered, and the filtrate was diluted with water and extracted with dichloromethane. The extract was washed with saturated NaHCO$_3$ (aq.) solution and brine, dried over anhydrous Na$_2$SO$_4$, filtered, and evaporated to give an oily residue. The residue was purified using preparative TLC developed by 50% EtOAc in hexane to afford the desired product CYD-6-86 as a colorless gel (9.0 mg, 90%). HPLC purity 97.5% (t$_R$ =18.62 min). $^1$H NMR (600 MHz, CDCl$_3$) δ 6.29 (d, 1H, J=10.2 Hz), 6.19 (s, 1H), 6.00 (d, 1H, J=10.2 Hz), 5.60 (s, 1H), 5.54 (d, 1H, J=12.0 Hz), 4.84 (s, 1H), 4.16 (d, 1H, J=10.2 Hz), 4.07 (m, 1H), 4.01 (d, 1H, J=10.2 Hz), 3.10 (d, 1H, J=8.4 Hz), 2.58 (m, 1H), 1.93 (d, 1H, J=7.8 Hz), 1.88 (m, 2H), 1.76 (m, 1H), 1.66 (s, 3H), 1.60 (m, 2H), 1.37 (s, 3H), 1.36 (s, 3H), 1.27 (s, 3H). $^{13}$C NMR (150 MHz, CDCl$_3$) δ 204.1, 203.2, 149.9, 142.6, 129.8, 121.2, 101.5, 95.4, 70.9, 69.8, 64.1, 56.2, 55.7, 48.3, 44.6, 40.1, 38.8, 30.1, 29.9, 25.4, 23.9, 22.4, 17.1. HRMS Calcd for $C_{23}H_{29}O_6$: [M+H]$^+$ 401.1959; found 361.1962.

Example 22

(4aS,5S,6S,6aR,9S,11aS,11bR,14R)-5,6,14-trihydroxy-4,4-dimethyl-8-methylene-4,4a,5,6,9,10,11,11a-octahydro-3H-6,11b-(epoxymethano)-6a,9-methanocyclohepta[a]naphthalene-3,7(8H)-dione (CYD-6-93)

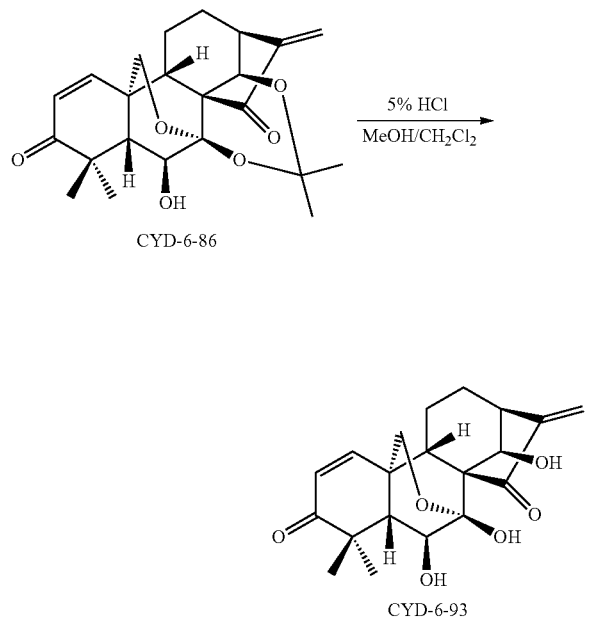

Example 23

(3S,3aR,3a¹R,6aR,7S,7aR,11aS,11bS,Z)-10-((dimethylamino)methylene)-7-hydroxy-5,5,8,8-tetramethyl-15-methyleneoctahydro-1H-6a,11a-(epoxymethano)-3,3a¹-ethanophenanthro[1,10-de] [1,3]dioxine-11,14(2H)-dione (CYD-6-77)

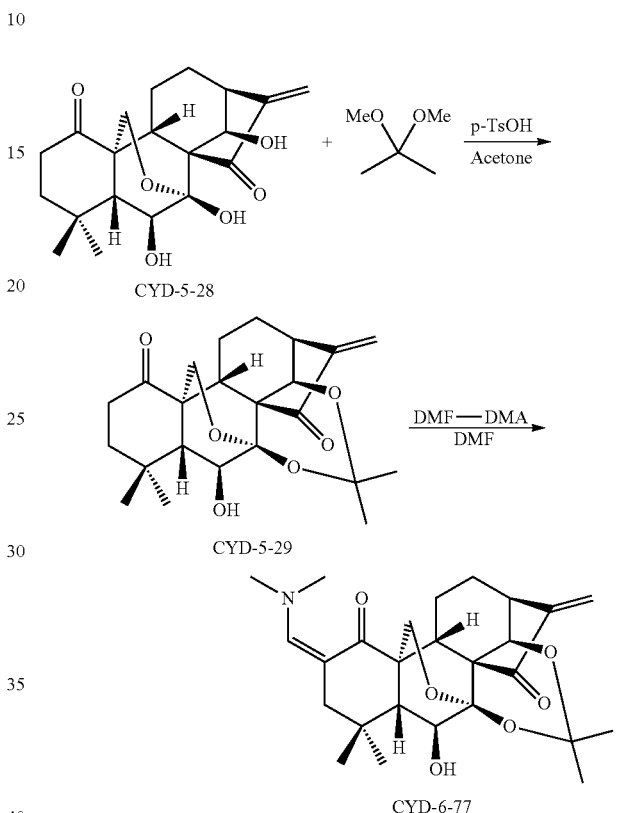

To a solution of CYD-6-86 (15 mg, 0.037 mmol) in a mixture of MeOH (2 mL) and CH$_2$Cl$_2$ (0.5 mL) was added 5% HCl aqueous solution (0.5 mL) at rt. The resulting mixture was stirred at rt for 4 hrs. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to give an oily residue. The residue was purified using preparative TLC developed by 66% EtOAc in hexane to afford the desired product CYD-6-93 as a colorless gel (10 mg, 74%). HPLC purity 98.2% ($t_R$=14.87 min). $^1$H NMR (600 MHz, CDCl$_3$) δ 6.31 (d, 1H, J=10.2 Hz), 6.22 (s, 1H), 6.13 (d, 1H, J=11.4 Hz), 6.02 (d, 1H, J=10.8 Hz), 5.63 (s, 1H), 4.92 (s, 1H), 4.17 (d, 1H, J=10.2 Hz), 4.06 (dd, 1H, J=1.8 Hz, 10.2 Hz), 3.98 (m, 1H), 3.10 (d, 1H, J=9.0 Hz), 2.58 (m, 1H), 1.95 (d, 1H, J=9.0 Hz), 1.91 (m, 2H), 1.65 (m, 3H), 1.34 (s, 3H), 1.26 (s, 3H). $^{13}$C NMR (150 MHz, CDCl$_3$) δ 206.0, 202.8, 150.5, 142.7, 130.0, 122.2, 97.7, 72.4, 72.1, 64.8, 61.7, 55.6, 51.4, 44.4, 42.5, 39.2, 29.4, 23.6, 22.0, 17.5; HRMS Calcd for $C_{20}H_{25}O_6$: [M+H]$^+$ 361.1646; found 361.1651.

To a solution of CYD-5-28 (250 mg, 0.68 mmol) in acetone (10 mL) was added TsOH (20 mg) and 2,2-dimethoxypropane (1.0 mL) at rt. The resulting mixture was stirred at rt for 2 hrs. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to afford compound CYD-5-29 as a colorless gel (230 mg, 83%). To a solution of CYD-5-29 (230 mg, 0.57 mmol) in DMF (4 mL) was added DMF-DMA (136 mg, 1.14 mmol) at rt. The resulting mixture was refluxed at 110° C. for 36 hrs. After that, the solvent was removed under vacuum to give a brown oily residue, which was further purified using preparative TLC developed by 66% EtOAc in hexane to afford the desired product CYD-6-77 as a colorless gel (120 mg, 46%). $^1$H NMR (600 MHz, CDCl$_3$) δ 7.42 (s, 1H), 6.14 (s, 1H), 5.55 (s, 1H), 5.20 (d, 1H, J=12.0 Hz), 4.87 (s, 1H), 4.31 (d, 1H, J=10.2 Hz), 4.04 (d, 1H, J=10.2 Hz), 3.87 (m, 1H), 3.07 (s, 6H), 3.04 (d, 1H, J=9.6 Hz), 2.47 (m, 3H), 1.97 (m, 2H), 1.66 (s, 3H), 1.62 (m, 1H), 1.56 (m, 2H), 1.34 (s, 3H), 1.23 (s, 3H), 1.00 (s, 3H); HRMS Calcd for $C_{26}H_{36}NO_6$: [M+H]458.2537; found 458.2541.

Example 24

(3S,3aR,3a¹R,6aR,7S,7aR, 11aS,11bS,Z)-7-hydroxy-10-(hydroxymethylene)-5,5,8,8-tetramethyl-15-methyleneoctahydro-1H-6a,11a-(epoxymethano)-3,3 a¹-ethanophenanthro[1,10-de] [1,3]dioxine-11,14(2H)-dione (CYD-6-91)

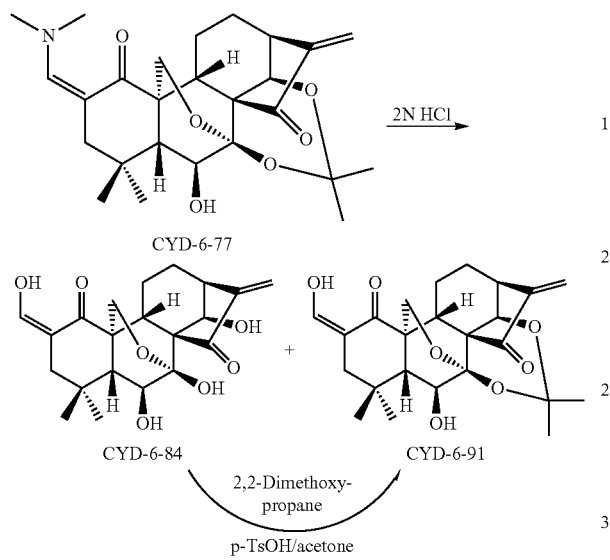

To a solution of CYD-6-77 (200 mg, 0.43 mmol) in THF (5 mL) was added 2 N HCl aqueous solution (0.5 mL) at rt. The resulting mixture was stirred at rt for 1 h. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to give an oily residue. The residue was further purified using preparative TLC developed by 60% EtOAc in hexane to afford the desired product CYD-6-91 (100 mg, 51%) and the further deprotected product CYD-6-84 (30 mg, 17%) as a colorless gel, respectively.

To a solution of CYD-6-84 (30 mg, 0.076 mmol) in acetone (4 mL) was added TsOH (5 mg) and 2,2-dimethoxypropane (0.3 mL) at rt. The resulting mixture was stirred at rt for 2 hrs. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to afford compound CYD-6-91 (28 mg, 84%) as a colorless gel.

CYD-6-84: ¹H NMR (300 MHz, CDCl$_3$) δ 8.33 (s, 1H), 6.21 (s, 1H), 5.83 (d, 1H, J=12.0 Hz), 5.61 (s, 1H), 4.96 (s, 1H), 4.33 (d, 1H, J=9.9 Hz), 4.08 (d, 1H, J=9.9 Hz), 3.80 (m, 2H), 3.06 (d, 1H, J=9.3 Hz), 2.49 (m, 1H), 2.31 (m, 1H), 2.24 (m, 1H), 2.04 (m, 3H), 1.76 (m, 1H), 1.61 (m, 2H), 1.25 (s, 3H), 1.01 (s, 3H).¹³C NMR (75 MHz, CDCl$_3$) δ 206.3, 185.8, 184.1, 151.1, 121.8, 109.5, 98.0, 72.9, 71.9, 65.1, 62.1, 57.6, 51.3, 44.5, 42.4, 39.9, 33.3, 30.1, 29.9, 20.2, 19.9.

CYD-6-91: ¹H NMR (300 MHz, CDCl$_3$) δ 14.72 (d, 1H, J=3.3 Hz), 8.39 (s, 1H), 6.19 (s, 1H), 5.60 (s, 1H), 5.29 (d, 1H, J=12.0 Hz), 4.90 (s, 1H), 4.30 (dd, 1H, J=1.2 Hz, 9.9 Hz), 4.09 (dd, 1H, J=0.9 Hz, 9.9 Hz), 3.92 (m, 1H), 3.09 (d, 1H, J=9.6 Hz), 2.55 (m, 1H), 2.29 (d, 1H, J=15.0 Hz), 2.05 (m, 3H), 1.84 (m, 1H), 1.67 (s, 3H), 1.60 (m, 2H), 1.37 (s, 3H), 1.29 (s, 3H), 1.04 (s, 3H). ¹³C NMR (75 MHz, CDCl$_3$) δ 204.6, 185.4, 184.8, 150.4, 120.7, 109.2, 101.2, 95.7, 71.6, 70.0, 64.4, 58.1, 56.0, 48.3, 43.7, 40.1, 39.9, 33.2, 30.5, 30.3, 30.0, 25.3, 20.6, 19.8; HRMS Calcd for C$_{24}$H$_{31}$O$_7$: [M+H]$^+$ 431.2064; found 431.2063.

Example 25

(3S,3aR,3a¹R,6aR,7S,7aR,11aS,11bS)-7-hydroxy-5,5,8,8-tetramethyl-15-methylene-11,14-dioxo-2,3,3 a,7,7a,8,11,1 I b-octahydro-1H-6a,11a-(epoxymethano)-3,3 a¹-ethanophenanthro[1,10-de] [1,3]dioxine-10-carbaldehyde (CYD-6-92)

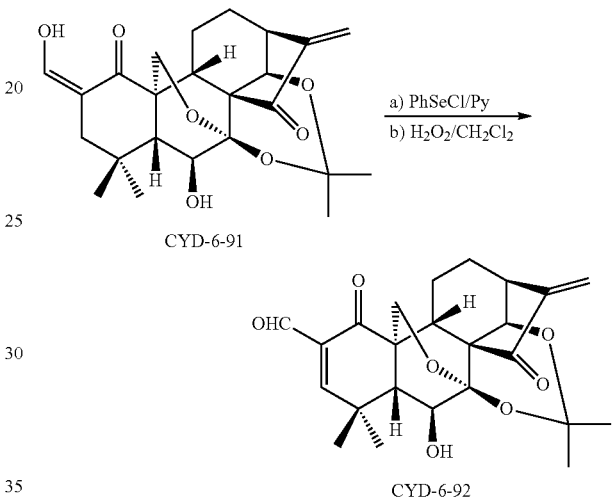

To a stirring solution of phenylselenyl chloride (33.6 mg, 0.175 mmol) in CH$_2$Cl$_2$ (3 mL) at 0° C. was added pyridine (0.017 mL, 0.208 mmol). The solution was stirred for 45 min, and then a solution of a-keto aldehyde CYD-6-91 (60 mg, 0.139 mmol) in CH$_2$Cl$_2$ (2 mL) was added. The mixture was stirred for 15 min at 0° C. and 45 min at rt. It was then extracted twice with 1 N HCl (aq.). The organic phase was dried over MgSO$_4$, filtered, and concentrated under reduced pressure. The crude product was further purified using the preparative TLC developed by hexane/EtOAc (1:1) to afford the selenide as yellow gel (60.0 mg, 74%).

To a stirring solution of the above selenide (60.0 mg, 0.102 mmol) in CH$_2$Cl$_2$ (5.8 mL) was added 35% H$_2$O$_2$ (aq.) solution (0.10 mL, 1.2 mmol). The mixture was vigorously stirred for 5 min, followed by the addition of another portion of 35% H$_2$O$_2$ (aq.) solution (0.10 mL, 1.2 mmol) with vigorous stirring for another 5 min. The reaction mixture was then extracted twice with water. The extract was dried over MgSO$_4$, filtered, and concentrated under reduced pressure. HPLC purity 98.1% (t$_R$=18.33 min). ¹H NMR (600 MHz, CDCl$_3$) δ 9.83 (s, 1H), 7.59 (s, 1H), 6.18 (s, 1H), 5.61 (s, 1H), 5.42 (d, 1H, J=12.6 Hz), 4.89 (s, 1H), 4.33 (dd, 1H, J=1.2 Hz, 10.2 Hz), 4.09 (m, 2H), 3.10 (d, 1H, J=9.0 Hz), 2.56 (m, 1H), 2.06 (m, 2H), 2.00 (d, 1H, J=8.4 Hz), 1.67 (s, 3H), 1.56 (m, 3H), 1.52 (s, 3H), 1.36 (s, 3H), 1.32 (s, 3H). ¹³C NMR (150 MHz, CDCl$_3$) δ 204.5, 195.2, 188.0, 168.4, 150.0, 133.0, 121.3, 101.5, 95.8, 71.3, 69.8, 64.9, 56.1, 55.7, 47.0, 46.5, 40.0, 36.2, 30.0, 29.7, 25.3, 24.2, 19.0. HRMS Calcd for C$_{24}$H$_{29}$O$_7$: [M+H]$^+$ 429.1908; found 429.1897.

Example 26

(2R,4aR,5S,6S,6aR,6a'R,7'S,8'S,8a'R,9S,11aS,11bS, 11'S,13a'S,13b'S,14R,16'R)-5,6,7',8',14,16'-hexahydroxy-4,4,6',6'-tetramethyl-8,10'-dimethylene-4,4a,5, 6,6',6a',7', 8',9, 10,11,11a,11',12',13',13a'-hexadecahydro-3'H-spiro[6,11b-(epoxymethano)-6a, 9-methanocyclohepta[α]naphthalene-2,2'-8,13b-(epoxymethano)-8a,11-methanocyclohepta[3,4]benzo[1,2-h]chromene]-1,7,9'(3'H,4'H,5'H,8H,10'H)-trione (CYD-5-40-2)

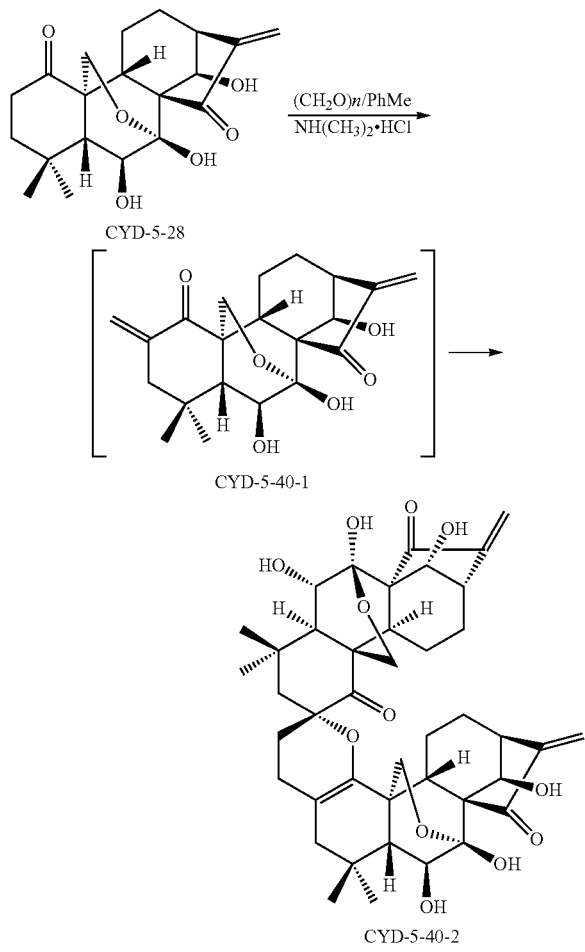

A mixture of CYD-5-28 (100 mg, 0.138 mmol), dimethylammonium chloride (48 mg, 0.294 mmol), paraformaldehyde (17 mg) in 1,4-dioxane (5 mL) was stirred and refluxed for 36 hrs. After that, the reaction mixture was diluted with water and extracted with dichloromethane.

The extract was washed with saturated $NaHCO_3$ (aq.) solution and brine, dried over anhydrous $Na_2SO_4$, filtered, and evaporated to give an oily residue. The residue was further purified using preparative TLC developed by 60% EtOAc in hexane to afford the desired product CYD-5-40-1 (23 mg, 22%) and a by-product CYD-5-40-2 (40 mg, 38%) as a colorless solid, respectively. CYD-5-40-1 is not very stable. CYD-5-40-2: HPLC purity 99.2% ($t_R$=18.10 min). $^1$H NMR (600 MHz, $CDCl_3$) δ 6.48 (s, 1H), 6.17 (s, 1H), 5.81 (s, 1H), 5.58 (s, 1H), 4.89 (s, 1H), 4.71 (s, 1H), 4.37 (d, 1H, J=10.2 Hz), 4.00 (m, 3H), 3.79 (d, 1H, J=8.4 Hz), 3.75 (d, 1H, J=8.4 Hz), 3.10 (d, 1H, J=9.0 Hz), 2.95 (d, 1H, J=9.6 Hz), 2.61 (m, 1H), 2.55 (m, 1H), 2.30 (m, 2H), 2.08 (m, 2H), 1.94 (m, 3H), 1.84 (m, 1H), 1.66 (m, 3H), 1.55 (m, 5H), 1.47 (m, 1H), 1.15 (s, 3H), 1.14 (s, 3H), 1.04 (s, 3H), 0.95 (s, 3H). $^{13}$C NMR (150 MHz, $CDCl_3$) δ 207.3, 206.8, 206.6, 151.6, 151.4, 142.0, 122.5, 121.6, 112.4, 98.4, 98.1, 80.4, 73.2, 72.7, 72.5, 65.7, 64.7, 62.3, 61.4, 60.6, 57.5, 53.8, 45.9, 43.4, 43.0, 42.0, 33.2, 32.3, 31.5, 30.8, 30.4, 30.0, 29.0, 25.2, 23.3, 20.9, 18.6. HRMS Calcd for $C_{42}H_{53}O_{12}$: $[M H]^+$ 749.3532; found 749.3540.

Example 27

(2R,4aR,4a'R,5'S,6aR,6'S,6a'R,7S,8S,8aR,9'S,11S, 11a'S,11b'S,13aS,13bS,13cR,14'R,17R)-5',6',7,8,14', 17-hexahydroxy-4',4',6,6-tetramethyl-8',10-dimethylenehexadecahydro-3H-spiro[4a,13c-epoxy-8,13b-(epoxymethano)-8a,11-methanocyclohepta[3,4]benzo[1,2-h]chromene-2,2'-6,11b-(epoxymethano)-6a,9-methanocyclohepta[α]naphthalene]-1',7',9(3'H, 4H,5H,8'H,10H)-trione (CYD-6-39)

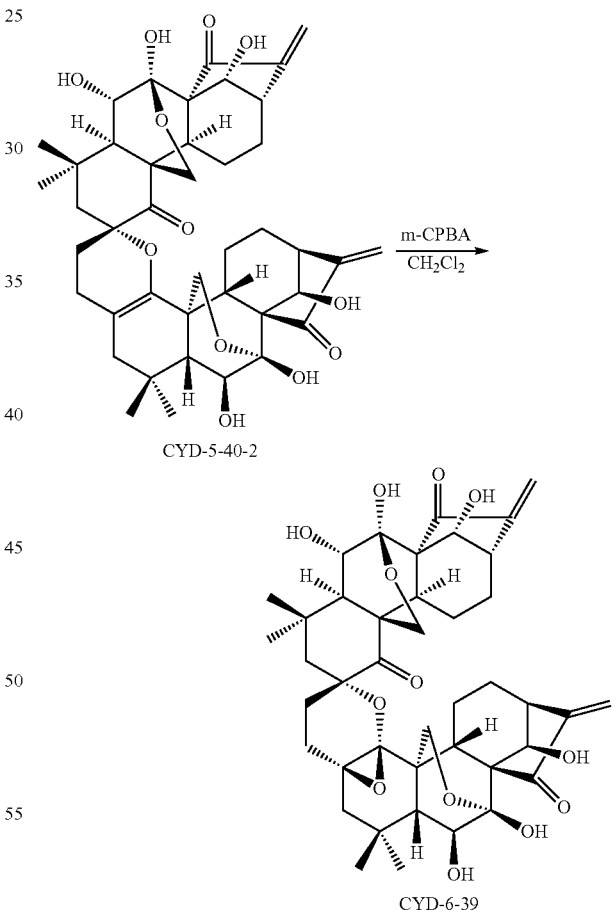

To solution of CYD-5-40-2 (15 mg, 0.02 mmol) in dichloromethane (4 mL) was added m-CPBA (4.0 mg, 0.02 mmol) at 0° C. The resulting mixture was stirred at rt for 1 h. After that, the reaction mixture was diluted with water and extracted with dichloromethane. The extract was washed with saturated $NaHCO_3$ (aq.) solution and brine, dried over anhydrous $Na_2SO_4$, filtered, and evaporated to give an oily residue. The residue was further purified using preparative TLC developed by 60% EtOAc in hexane to afford the desired product CYD-6-39 as a colorless solid (12 mg, 80%). Its chemical structure and absolute configurations were determined by X-ray analysis of CYD-6-39 single crystal. HPLC purity 98.7% ($t_R$=15.84 min. $^1$H NMR (600 MHz, CDCl$_3$) δ 6.49 (s, 1H), 6.18 (s, 1H), 5.82 (s, 1H), 5.59 (s, 1H), 4.89 (s, 1H), 4.80 (s, 1H), 4.35 (d, 1H, J=10.2 Hz), 4.31 (s, 1H), 4.21 (d, 1H, J=9.6 Hz), 4.15 (d, 1H, J=10.2 Hz), 3.99 (d, 1H, J=10.2 Hz), 3.74 (s, 1H), 3.72 (s, 1H), 3.12 (d, 1H, J=9.0 Hz), 2.95 (d, 1H, J=9.6 Hz), 2.63 (m, 1H), 2.51 (m, 1H), 2.46 (d, 1H, J=7.8 Hz), 2.37 (m, 1H), 2.19 (m, 1H), 2.11 (m, 1H), 2.01 (d, 1H, J=15.0 Hz), 1.89 (m, 3H), 1.72 (t, 2H, J=13.8 Hz), 1.58 (m, 5H), 1.22 (s, 3H), 1.20 (s, 3H), 1.06 (s, 3H), 0.93 (s, 3H). $^{13}$C NMR (150 MHz, CDCl$_3$) δ 207.5, 206.1, 151.7, 151.5, 122.2, 121.5, 98.4, 97.7, 86.0, 80.5, 73.1, 73.0, 72.9, 72.8, 66.2, 66.0, 64.1, 61.7 (2C), 57.8, 57.4, 52.3, 47.0, 43.8, 43.4, 41.9, 33.1, 32.5, 31.1, 30.8, 30.2, 30.0, 29.4, 27.3, 25.6, 25.4, 22.5, 19.3, 18.6. HRMS Calcd for C$_{42}$H$_{53}$O$_{13}$: [M+H]$^+$765.3481; found 749.3484.

Example 28

Retrosynthetic Analysis for the Construction of Various Substituted 2H-pyran-fused Oridonin Derivatives

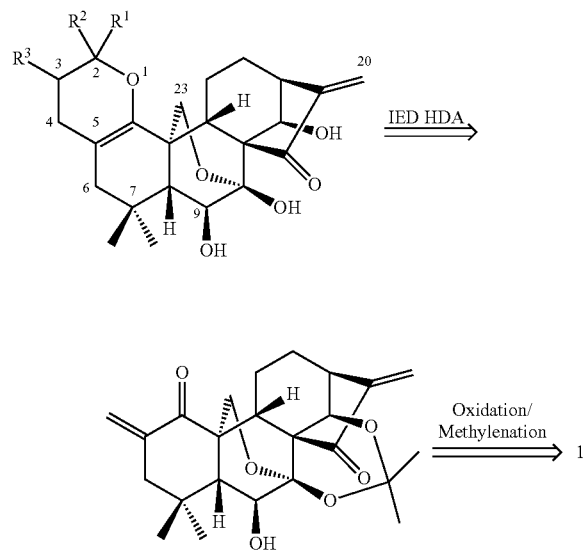

This synthetic scheme is a retrosynthetic analysis for constructions of various 3,4-dihydro-2H-pyran-fused derivatives of oridonin 1. One step, IED HDA reaction of electron-rich vinyl dienophiles with the exocyclic α,β-unsaturated ketone functionality created in the A-ring would provide a direct route to the desired pyran ring. However, two synthetic challenges arising from this strategy remain to be addressed: (1) How to selectively perform HDA reaction at the A-ring, rather than the enone system in the D-ring that is a key bioactivity center; and (2) How to achieve the desired cross-Diels-Alder cycloaddition instead of homo-Diels-Alder dimerization from the diversity perspective. Therefore, controlled regio- and stereoselective cross-HDA reactions at the A-ring of oridonin are highly desired.

The synthetic effort commenced with oridonin, a naturally abundant and commercially available ent-kaurane diterpenoid (Scheme 1). Selective oxidation of oridonin with Jones reagent readily provided the 1-ketone derivative CYD-6-58 in 82% yield (Zhou and Cheng, Acta Chim. Sinica 1990, 48, 1185-1190). The direct α-methylenation of CYD-6-58 utilizing paraformaldehyde (PFA) and dimethylamine hydrochloride in refluxing 1,4-dioxane for 4 h, without any protection, smoothly afforded intermediate 3, in which the exocyclic enone system was successfully installed in the A-ring. However, 3 turned out to be unstable and was prone to undergo self-dimerization automatically. It was found that the purified 3 was allowed to stand at −20° C. or rt for 21 days to solely generate the spirochroman product 4 in 68% and 72% yield, respectively. When the temperature was increased to 80° C. for 2 days, 4 was obtained in 80% yield. In a solution of 1,4-dioxane (0.5 mol/L) at rt, the reaction proceeded more slowly than that without solvent; on the contrary, the reaction was accelerated to give 4 in 70% yield by refluxing the reaction solution at 110° C. for 4 days. Inspired by these findings, we attempted to access 4 directly from CYD-6-58 through one-pot tandem α-methylenation/homo-HDA reactions. Thus, refluxing CYD-6-58 with PFA and dimethylamine hydrochloride in 1,4-dioxane for 4 days readily furnished 4 in 65% yield. The structure of 4 was well characterized by spectroscopic data including $^1$H and $^{13}$C NMR, HRMS, HMQC and HMBC. According to previous reported self-HDA cycloaddition of α-alkylidene ketones (Li et al. Org. Lett. 2010, 12, 4284-87; Uroos and Hayes Org. Lett. 2010, 12, 5294-97; Li et al. J. Am. Chem. Soc. 2012, 134, 12414-17), the formation of 4 from 3 is considered to be derived through A-ring-selective HDA reaction between the exocyclic enone of one molecule and the exomethylene of the other, in which the enone approached the exo-methylene from the less hindered α-face, but not the blocked β-face due to the bulky ent-kaurane ring system leading to a high facial selectivity. The stereochemistry of the spiro carbon C-2' of 4 was thus tentatively assigned as R configuration, which was further confirmed through X-ray crystallographic analysis at a later stage by converting 4 into 5. Interestingly, the naturally occurring enone of oridonin was reported to presumably undergo dimerization into bis-rubescensin C in vivo (Huang et al. Org. Lett. 2006, 8, 1157-60). Nevertheless, in our cycloaddition reactions, only the enone system in the A-ring was selectively involved, while the one in the D-ring was found intact. The high regioselectivity of this homo-HDA reaction on the enone system is likely ascribed to the less crowded steric environment of the heterodiene in the A-ring in comparison with that in the D-ring.

Scheme 1

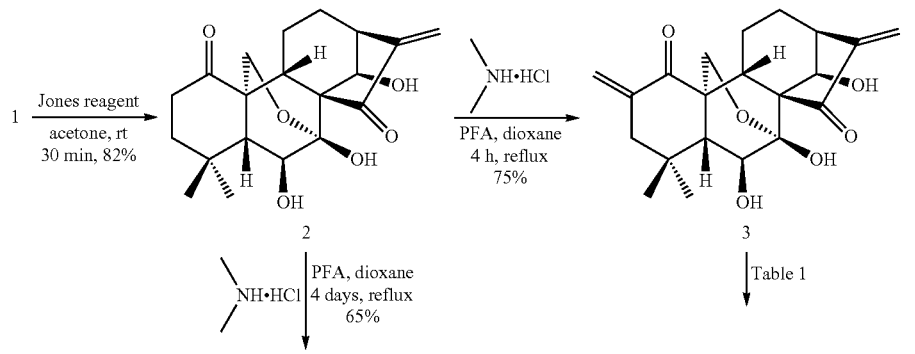

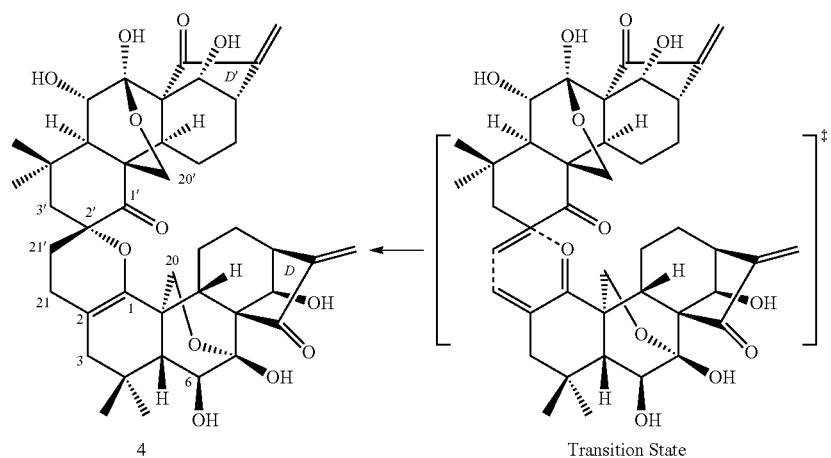

Example 29

Regio- and Stereoselective Epoxidation of 4 Mediated by m-CPBA

Compound 4 was then subjected to an epoxidation reaction by treatment with m-CPBA in CH$_2$Cl$_2$ at rt, exclusively leading to β-epoxide 5 in a good yield of 80%. The structure of 5 was unambiguously determined by X-ray crystallographic analysis (Scheme 2), which secured the stereochemistry of both 4 and 5. In this step, the reaction occurred preferentially at the 1-ene rather than two exo-methylenes in the D and D' rings, respectively, and selectively formed 1,2-epoxide ring from the less sterically hindered β-face. Although some natural ent-kaurane dimers isolated from the genus isodon have been previously reported, (Shenet al. *Phytochemistry,* 1994, 35, 725-29; Na et al. *Chin. J. Chem.* 2002, 20, 884-86; Han et al. *Tetrahedron Lett.* 2004, 45, 2833-37) homo-dimers 4 and 5 are the first examples of dimeric ent-kaurane diterpenoids with the intact enone functionality in the D-ring.

Scheme 2

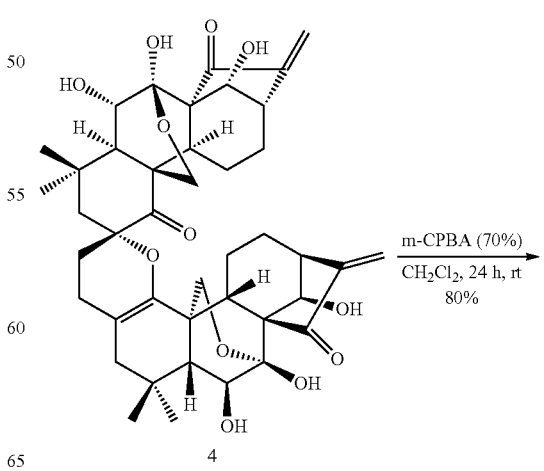

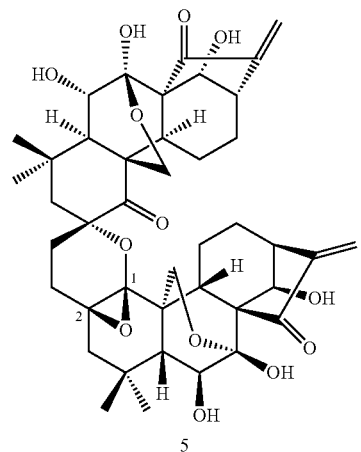

5

Example 30

Cross-HDA Reaction of 7 with n-Butyl Vinyl Ether

Scheme 3

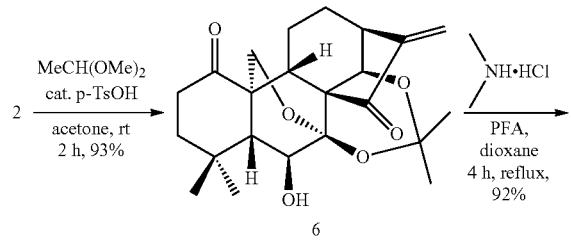

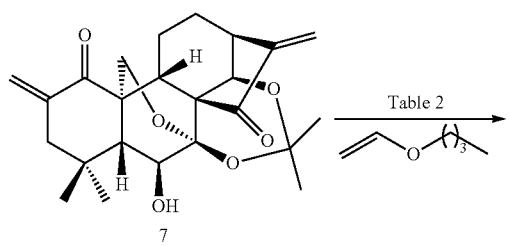

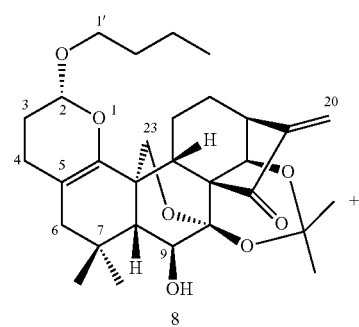

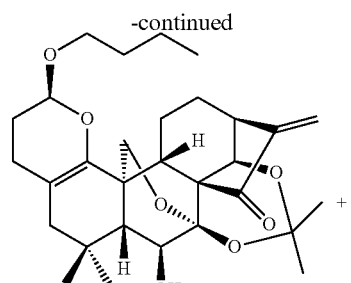

9

10

While selectively achieving 4 generated excitement, preventing the homo-dimerization of 3 during the development of A-ring-selective cross-HDA reactions with the aim to diversely construct pyran-fused derivatives was one goal. Initially, 3 without any protection was chosen as the heterodiene to undergo $Eu(fod)_3$-catalyzed cross-HDA reaction with n-butyl vinyl ether at rt for the purpose of atom-economy. The reaction was very complex with a mixture of several side products including homo-dimer 4 as well as partially recovered 3. Accordingly, the acetonide protection of 7,14-dihydroxyl of 3 into 7 was deemed necessary to avoid potential side reactions. Moreover, introduction of the acetonide protecting group might also enhance the steric effect of the heterodiene in the D-ring leading to an improved regioselectivity for the A-ring. To reduce the chance of self-dimerization as much as possible, the protecting group was first installed to form 6 followed by α-methylenation to give the acetonide 7, instead of the direct protecting reaction of 3 (Scheme 3). With 7 in hand, we attempted to investigate its cross-HDA reaction with n-butyl vinyl ether. When the reaction was performed in a solution of 1,4-dioxane or THF at rt using 10 mol % of $Eu(fod)_3$ as the catalyst, only trace amount of the desired cycloadducts 8 and 9 were detected after 72 h; instead, dimer 10 was obtained in 24% and 21% yields, respectively, together with partially recovered 7. Increasing the reaction temperature to 80° C. predominantly led to dimer 10 in 62% yield along with cycloadducts 8 and 9 in total 15% isolated yield. Both 8 and 9 were fully characterized by spectroscopic data including $^1H$ and $^{13}C$ NMR, HRMS, HMBC, HMQC and NOESY, respectively, owing to their good separation by preparative TLC. Characteristic HMBC correlations indicate the presence of the pyran moiety fused into the A-ring of 8 and 9. The stereochemistry of C-2 was determined by NOESY experiments, in which the cross peaks for H-23 and H-1' of 8 indicated that C-2 had R configuration, and its appended ethereal C—O bond was assigned as α-oriented; on the contrary, no similar cross peaks for H-23 and H-1' of 9 were observed, suggesting C-2 had S configuration, and its ethereal C—O bond was on the β-face. The conformations of the dihydropyran rings in 8 and 9 were also deduced from chemical shift values and coupling constants of protons attached to C-2. $^1$H NMR spectra of 8 reveal the signals of proton on C-2 as a triplet at 4.89 ppm with a small coupling constant of 2.1 Hz. Thus, the proton at C-2 in 8 is equatorial, while the n-butoxy group occupies the axial position. For diastereoisomer 9, the proton at C-2 resonates as a doublet of doublets at 4.58 ppm with two coupling constants of 1.5 Hz and 9.0 Hz, respectively, due to coupling with two protons at C-3. Thus, the proton at C-2 in 9 is axial. The stereochemistry of these two isomers was also secured later by the X-ray crystallographic analysis of analogue 20.

Since the undesired homo-dimerization of 7 was still predominant, we attempted to employ n-butyl vinyl ether as solvent to favor the desired cross-HDA reaction. To our delight, treatment of 7 with 10 mol % of Eu(fod)$_3$ in a solution of n-butyl vinyl ether for 7 days provided 8 and 9 in total 63% yield with the diastereomeric ratio of 53:47 as major products over dimer 10 (18% yield). Moreover, no cycloadducts of the enone in the D-ring were found presumably due to the aforementioned hindered steric effects. In the absence of Eu(fod)$_3$, no desired cycloadducts 8 and 9 were observed, suggesting that lanthanide Lewis acid (LA) catalyst is a prerequisite for this HDA reaction due to its unique properties for coordination to the ketone functionality of the enone system in the A-ring, leading to its activation. Recently, important advances have been made in auxiliary-controlled IED HDA reactions to stereoselectively construct chiral pyran moieties (Pellissier, *Tetrahedron* 2009, 65, 2839-77; Gizecki et al. *Org. Lett.* 2000, 2, 585-88; Gallier et al. *Org. Lett.* 2009, 11, 3060-63; Messer et al. *J. Org. Chem.* 2004, 69, 8558-60; Johnson et al. *Chem. Commun.* 1998, 1019-20). 7 with a stereochemistry-rich framework could be considered as a chiral auxiliary heterodiene, but the stereoselectivity in our case was very poor. Therefore, we continued our effort to optimize the reaction conditions by screening other Lewis acids and hydrogen bond donor catalysts. It was found that 10 mol % of Yb(fod)$_3$ at 32° C. offered an optimal result leading to 8 and 9 in total 68% yield with an enhanced diastereomeric ratio of 10:90. Although their endo/exo selectivity can not be exactly determined due to the structural nature of these substrates, such IED HDA reactions catalyzed by Eu(fod)$_3$ or Yb(fod)$_3$ are likely endo-selective according to the relevant literature (Gizecki et al. *Org. Lett.* 2000, 2, 585-88; Gallier et al. *Org. Lett.* 2009, 11, 3060-63; Wada et al. *Tetrahedron* 1996, 5, 1205-20; Wada et al. *Chem. Lett.* 1994, 145-48; Bogdanowicz-Szwed and Palasz *Monatsh. Chem.* 1997, 128, 1157-72). It is also reported that different coordination modes of Eu(fod)$_3$ and Yb(fod)$_3$ may account for their different facial selectivity in HDA reaction (Cousins et al. *Chem. Commun.* 1997, 2171-72; Turov et al. *Chemistry of Heterocyclic Compounds*, 2004, 40, 986-91; Turov et al. Russ. *J. Org. Chem.* 2005, 41, 47-53). The high facial selectivity induced by Yb(fod)$_3$ may be explained by the possibility that an extra α-face coordination to the 7,20-epoxy probably occurs to block α-face during the activation of 1-ketone of the A-ring, and consequently, the dienophile approaches to the heterodiene mainly from the less hindered β-face in an endoselective manner. In the case of more oxophilic Eu(fod)$_3$, it is likely not only to chelate with the 7,20-epoxy from α-face, but also coordinate to both 6-hydroxyl and 15-ketone to form the bidentate complex from β-face, leading to the blockage of both α- and β-faces, which eventually results in the poor facial selectivity and longer reaction time. Other catalysts such as Ti(O-iPr)$_4$ and (±)-BINOL also promote this reaction, but the yields are much lower (entries 9 and 10). In addition, no reaction or decomposition was observed when ZnCl$_2$ or Cu(OTf)$_2$ was employed as catalysts (entries 6 and 8).

TABLE 4

Optimization of Cross-HDA Reaction Conditions for 8 and 9$^a$

| Entry | Catalyst | Solvent | Temperature (° C.) | Time (h) | Dr (8/9)$^b$ | Yield (%)$^c$ 8 and 9 | 10 |
|---|---|---|---|---|---|---|---|
| 1 | Eu(fod)$_3$ | 1,4-dioxane$^d$ | Rt | 72 | —$^e$ | trace | 24 |
| 2 | Eu(fod)$_3$ | THF$^d$ | Rt | 72 | — | trace | 21 |
| 3 | Eu(fod)$_3$ | 1,4-dioxane$^d$ | 80 | 72 | 45:55 | 15 | 62 |
| 4 | Eu(fod)$_3$ | n-butyl vinyl ether | Rt | 168 | 53:47 | 63 | 18 |
| 5 | None | n-butyl vinyl ether | Rt | 72 | — | NR$^f$ | 14 |
| 6 | ZnCl$_2$ | n-butyl vinyl ether | 32 | 72 | — | NR$^g$ | — |
| 7 | Yb(fod)$_3$ | n-butyl vinyl ether | 32 | 72 | 10:90 | 68 | 14 |
| 8 | Cu(OTf)$_2$ | n-butyl vinyl ether | 32 | 2 | — | decomposed | — |
| 9 | Ti(O—iPr)$_4$ | n-butyl vinyl ether | 32 | 72 | — | 13 | 30 |
| 10 | (±)-BINOL | n-butyl vinyl ether | 32 | 72 | — | 8 | 28 |

$^a$7 (0.1 mmol), n-butyl vinyl ether (1 mL), and 10% mol of catalysts.
$^b$Determined by isolated yield.
$^c$Isolated yield.
$^d$7 (1 equiv), n-butyl vinyl ether (4 equiv) and solvents (1 mL).
$^e$Not determined.
$^f$No reaction.
$^g$Polymerization of vinyl ether was observed.

Example 31

Substrate Scope of One-pot Cross-HAD Reactions with Various Vinyl Ether and Vinyl sulfide The optimized cross-HDA reaction condition was then applied for the synthesis of various substituted pyran-fused derivatives of 1 to explore the generality and scope. Several different vinyl ethers as well as vinyl sulfide were employed as the dienophiles to react with 7. To avoid self-dimerization during the reaction workup, intermediate 7 was directly used in the following HDA reaction without further purification. From the results summarized in Scheme 4 (shown in FIG. 12), 10 mol % Yb(fod)$_3$ was also found to be the effective catalyst and all reactions proceeded smoothly, affording the desired cycloadducts. In cases of ethyl vinyl ether, isobutyl vinyl ether, tent-butyl vinyl ether, 2-chloroethyl vinyl ether and allyl vinyl ether, the corresponding cycloadducts (compounds 11-20) were obtained in total 52-59% yields (2 steps) with roughly 10:90 ratios, generally similar to that of n-butyl vinyl ether. The steric effects of the substituents on vinyl ether did not show significant difference in terms of yields and diastereomeric ratios (Scheme 4 illustrated in FIG. 12, compounds 11-16). The high selectivity for the vinyl ether double bond versus the allyl double bond was also observed in the case of allyl vinyl ether (scheme 4, compounds 17-18). Furthermore, ethyl vinyl sulfide gave a slightly increased yield with completely controlled β-face selectivity to solely achieve compound 24 after shorter reaction time in comparison with ethyl vinyl ether. Different from others, the poor facial selectivity (dr=55:45, α/β) was unexpectedly observed when 1,4-butanediol vinyl ether was used as the dienophile. Interestingly, exchange of lanthanide catalyst from Yb(fod)$_3$ to Eu(fod)$_3$ exclusively led to compound 21 in 70% yield with totally controlled α-face selectivity, and no diastereoisomer 22 was found. The switchable facial selectivity in this HDA reaction could be explained based on our previously proposed reaction mode. It was speculated that the hydroxyl group of the dienophile might perturb the weak coordination of Yb(fod)$_3$ to the 7,20-epoxy owning to its superior chelating ability to make α-face unblocked, which resulted in the loss of facial selectivity. Similarly, this hydroxyl group was also able to disassociate the chelating complex of Eu(fod)$_3$ with the 7,20-epoxy to unblock α-face, but the more stable bidentate complex in β-face was still kept intact, and accordingly, the dienophile approached to the heterodiene exclusively from the less hindered α-face.

Example 32

Further Functional Group Transformations of 21 (scheme 5)

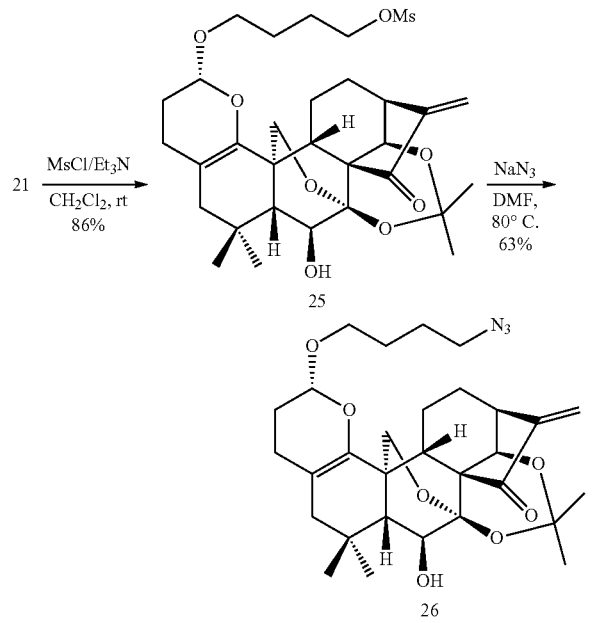

The terminal hydroxyl group of 21 could be considered as a starting point for further functional group transformations to generate structural diversity. As shown in Scheme 5, mesylation of 21 with MSCl in the presence of Et$_3$N selectively produced intermediate 25 in 86% yield, which was followed by treatment with NaN$_3$ to furnish a valuable azide 26 (63%) useful for building a potential compound library.

Example 33

One-Pot Cross-HDA Reaction of 6 with 3,4-Dihydro-2H-Pyran

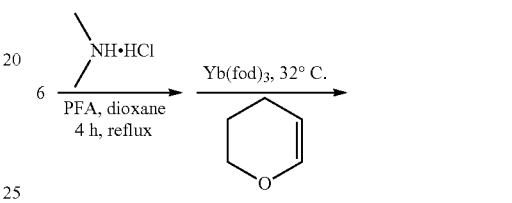

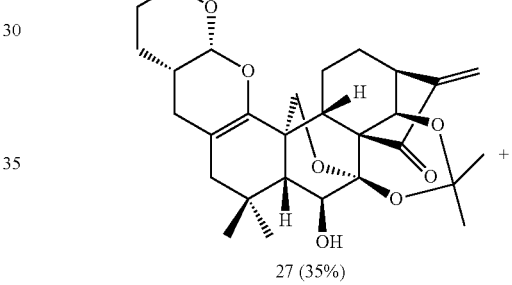

27 (35%)

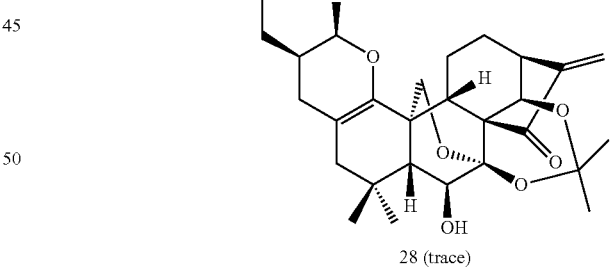

28 (trace)

To further explore the generality and scope of this reaction for the diversity of the ent-kaurane scaffold, 3,4-dihydro-2H-pyran was selected as the dienophile to undergo Yb(fod)$_3$-catalyzed cross-HDA reaction with 7. (2R,3S)-27 was obtained in 35% yield as the main cycloadduct, along with trace amount of (2S,3R)-28, after a long reaction time (7 days) likely through an exo-selective HDA reaction (Scheme 6). In this case, 3,4-dihydro-2H-pyran approaches to the heterodiene from the β-face in an exo-selective manner to give 27 due to the enhanced steric effect of the cyclic vinyl ether with the ent-kaurane ring system.

Example 34

Hydrolysis Reactions of Compounds 11 and 12 by 5% HCl(aq)

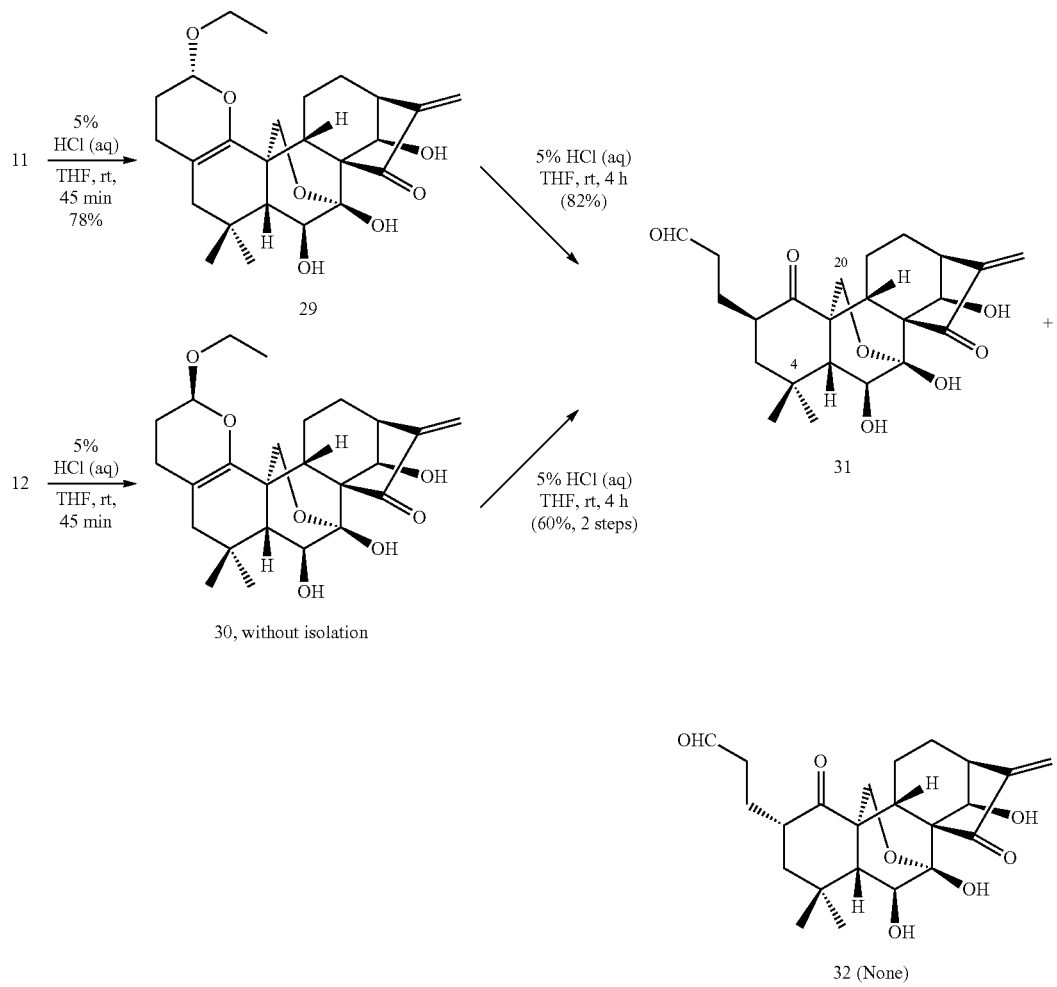

Considering that 3,4-dihydro-2H-pyran moieties are versatile synthetic building blocks for generation of various functionalized heterocycles, carbohydrates and natural products, we inevitably became interested in further chemical transformation based on this attractive scaffold. As shown in Scheme 7, treatment of compound 11 with 5% HCl (aq) for 45 min readily provided the deprotected derivative 29 in 78% yield, which was further hydrolyzed with 5% HCl (aq) for another 4 h to solely yield aldehyde 31 in 82% yield with high β-face selectivity. Acetonide deprotection of diastereoisomer 12 under the same condition gave the corresponding deprotected product 30, which was also prone to cleavage of the dihydropyran ring affording 31 in 60% yield (two steps). The structure of 31 was also well determined by $^1$H and $^{13}$C NMR, HRMS, HMBC, HMQC and NOSEY. 31 could be used as another common building block to extend the structural diversity.

Example 35

Synthesis of (2R,6aR,7S,7aR,7a$^1$R,10aR,11S,13aS, 13bS)-2-butoxy-7-hydroxy-6,6,9,9-tetramethyl-16-methylene-2,3,4,5,6,6a,7,10a,11,12,13,13a-dodecahydro-7a,13b-(epoxy methano)-7a$^1$,11-ethano[1,3] dioxino[4',5',6':4,5]naphtho[2,1-h]chromen-17-one (8) and (2S,6aR,7S,7aR,7a$^1$R,10aR,11S,13aS,13b5)-2-butoxy-7-hydroxy-6,6,9,9-tetramethyl-16-methylene-2,3,4,5,6,6a,7,10a,11,12,13,13a-dodecahydro-7a, 13b-(epoxymethano)-7a$^1$,11-ethano[1,3]dioxino[4', 5',6':4,5]naphtho[2,1-h]chromen-17-one (9).

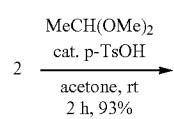

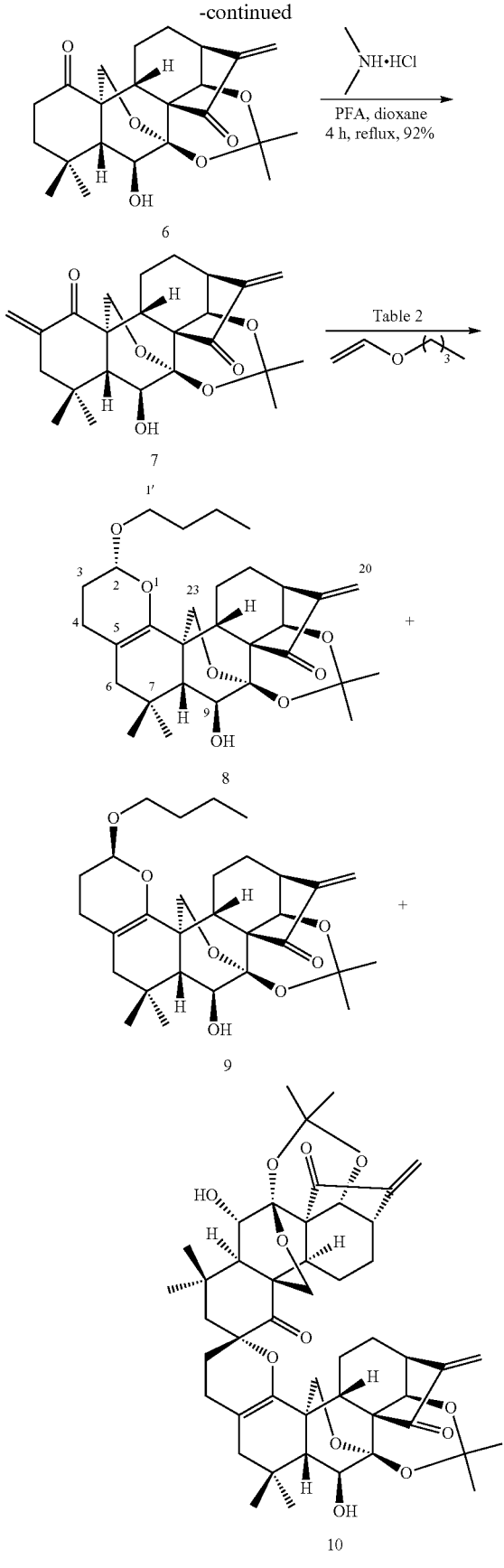

A mixture of 6 (50 mg, 0.12 mmol), dimethylammonium chloride (21 mg, 0.26 mmol), and paraformaldehyde (8.0 mg) in 1,4-dioxane (2 mL) was refluxed for 4 h. The reaction mixture was then diluted with 3 mL of water and extracted with 10 mL of dichloromethane three times. The extract was washed with saturated NaHCO$_3$ (aq) solution (5 mL) and brine (5 mL), dried over anhydrous Na$_2$SO$_4$, filtered, and evaporated to give an oily residue. The residue was purified using silica gel column; elution with 60% EtOAc in hexanes afforded the desired product 7 as a colorless gel (41 mg, 80%). $^1$H NMR (300 MHz, CDCl$_3$): δ 6.17 (s, 1H), 6.03 (s, 1H), 5.59 (s, 1H), 5.27 (s, 1H), 5.20 (d, 1H, J=12.0 Hz), 4.87 (s, 1H), 4.24 (d, 1H, J=9.9 Hz), 4.01 (d, 1H, J=9.9 Hz), 3.91 (dd, 1H, J=12.0 Hz, 9.0 Hz), 3.07 (d, 1H, J=9.0 Hz), 2.48 (m, 3H), 1.96 (m, 2H), 1.83 (d, 1H, J=8.7 Hz), 1.68 (m, 1H), 1.65 (s, 3H), 1.45 (m, 1H), 1.43 (m, 1H), 1.35 (s, 3H), 1.25 (s, 3H), 1.00 (s, 3H). $^{13}$C NMR (75 MHz, CDCl$_3$) δ 204.6, 199.0, 150.4, 141.7, 125.5, 120.8, 101.3, 95.8, 71.6, 70.0, 65.9, 59.5, 55.8, 47.0 (2C), 46.6, 40.1, 32.8, 30.2, 30.1, 30.0, 25.3, 21.5, 19.0. HRMS Calcd for C$_{24}$H$_{30}$O$_6$: [M+H]$^+$ 415.2115; found 415.2109.

To a solution of 7 (41 mg, 0.10 mmol) in n-butyl vinyl ether (1 mL) was added Yb(OTf)$_3$ (11 mg, 0.01 mmol) at rt. The resulting mixture was stirred at 32° C. for 72 h. The reaction mixture was then diluted with 3 mL of water and extracted with 10 mL of dichloromethane three times. The extract was washed with brine (5 mL), dried over anhydrous Na$_2$SO$_4$, filtered, and evaporated to give an oily residue. The residue was further purified using preparative TLC developed by 15% EtOAc in hexanes to afford the desired product 8 (3.4 mg) and 9 (31.1 mg) as colorless amorphous gel in total 68% yield.

8: [α]$^{25}_D$−10 (c 0.10, CH$_2$Cl$_2$). $^1$H NMR (300 MHz, CDCl$_3$): δ 6.14 (s, 1H), 5.54 (s, 1H), 5.31 (d, 1H, J=12.0 Hz), 4.89 (m, 1H), 4.85 (d, 1H, J=1.2 Hz), 4.23 (dd, 1H, J=9.6 Hz, 0.9 Hz), 4.00 (d, 1H, J=9.6 Hz), 3.89 (dd, 1H, J=12.0 Hz, 8.7 Hz), 3.53 (dt, 1H, J=9.0 Hz, 6.6 Hz), 3.37 (dt, 1H, J=9.6 Hz, 6.3 Hz), 3.03 (d, 1H, J=9.3 Hz), 2.49 (m, 1H), 1.86 (m, 7H), 1.65 (s, 3H), 1.62 (m, 2H), 1.49 (m, 4H), 1.34 (s, 3H), 1.29 (m, 2H), 1.16 (s, 3H), 1.01 (s, 3H), 0.89 (t, 3H, J=7.2 Hz). $^{13}$C NMR (75 MHz, CDCl$_3$) δ 204.7, 150.9, 140.7, 119.9, 108.8, 100.9, 95.4 (2C), 72.0, 70.1, 67.4, 64.1, 59.0, 56.5, 50.1, 45.2, 40.6, 40.3, 32.9, 31.8, 30.8, 30.6, 30.1, 26.8, 25.3, 21.9, 20.9, 20.6, 19.5, 13.9. HRMS Calcd for C$_{30}$H$_{42}$O$_7$: [M+H]$^+$ 515.3003; found 515.2999.

9: [α]$^{25}_D$+118 (c 0.10, CH$_2$Cl$_2$). $^1$H NMR (300 MHz, CDCl$_3$): δ 6.14 (s, 1H), 5.54 (s, 1H), 5.34 (d, 1H, J=11.7 Hz), 4.86 (d, 1H, J=0.9 Hz), 4.58 (dd, 1H, J=9.0 Hz, 1.5 Hz), 4.18 (d, 1H, J=8.7 Hz), 3.99 (d, 1H, J=9.6 Hz), 3.89 (dd, 1H, J=12.0 Hz, 8.7 Hz), 3.77 (dt, 1H, J=9.3 Hz, 6.3 Hz), 3.45 (dt, 1H, J=9.3 Hz, 6.3 Hz), 3.03 (d, 1H, J=9.0 Hz), 2.48 (m, 1H), 1.95 (m, 7H), 1.66 (s, 3H), 1.64 (m, 2H), 1.55 (m, 4H), 1.39 (m, 2H), 1.34 (s, 3H), 1.17 (s, 3H), 1.03 (s, 3H), 0.93 (t, 3H, J=7.2 Hz). $^{13}$C NMR (75 MHz, CDCl$_3$) δ 204.7, 150.9, 142.7, 120.0, 107.4, 100.9, 99.9, 95.4, 72.0, 70.1, 68.7, 63.9, 58.6, 56.5, 49.8, 44.8, 40.6, 40.3, 32.9, 31.7, 30.8 (2C), 30.1, 28.4, 25.9, 25.4, 21.3, 20.4, 19.3, 13.8. HRMS Calcd for C$_{30}$H$_{42}$O$_7$: [M+H]$^+$ 515.3003; found 515.2994.

Example 36

Synthesis of (2R,6aR,7S,7aR,7a$^1$R,10aR, 11S,13aS, 13bS)-2-ethoxy-7-hydroxy-6,6,9,9-tetramethyl-16-methy 1ene-2,3,4,5,6,6a,7,10a, 11,12,13,13 a-dodecahydro-7a, 13b -(epoxymethano)-7a$^1$,11-ethano [1,3]dioxino[4',5',6':4,5]naphtho[2,1-h]chromen-17-one (11) and (2S,6aR,7S,7aR,7a$^1$R, 10aR,11S,13aS, 13b,S)-2-ethoxy-7-hydroxy-6,6,9,9-tetramethyl-16-methylene-2,3,4,5,6,6a,7,10a,11,12,13,13a-dodecahydro-7a,13b-(epoxymethan6)-7a$^1$,11-ethano [1,3]dioxino[4',5',6':4,5]naphtho[2,1-h]chromen-17-one (12).

Figure 12:
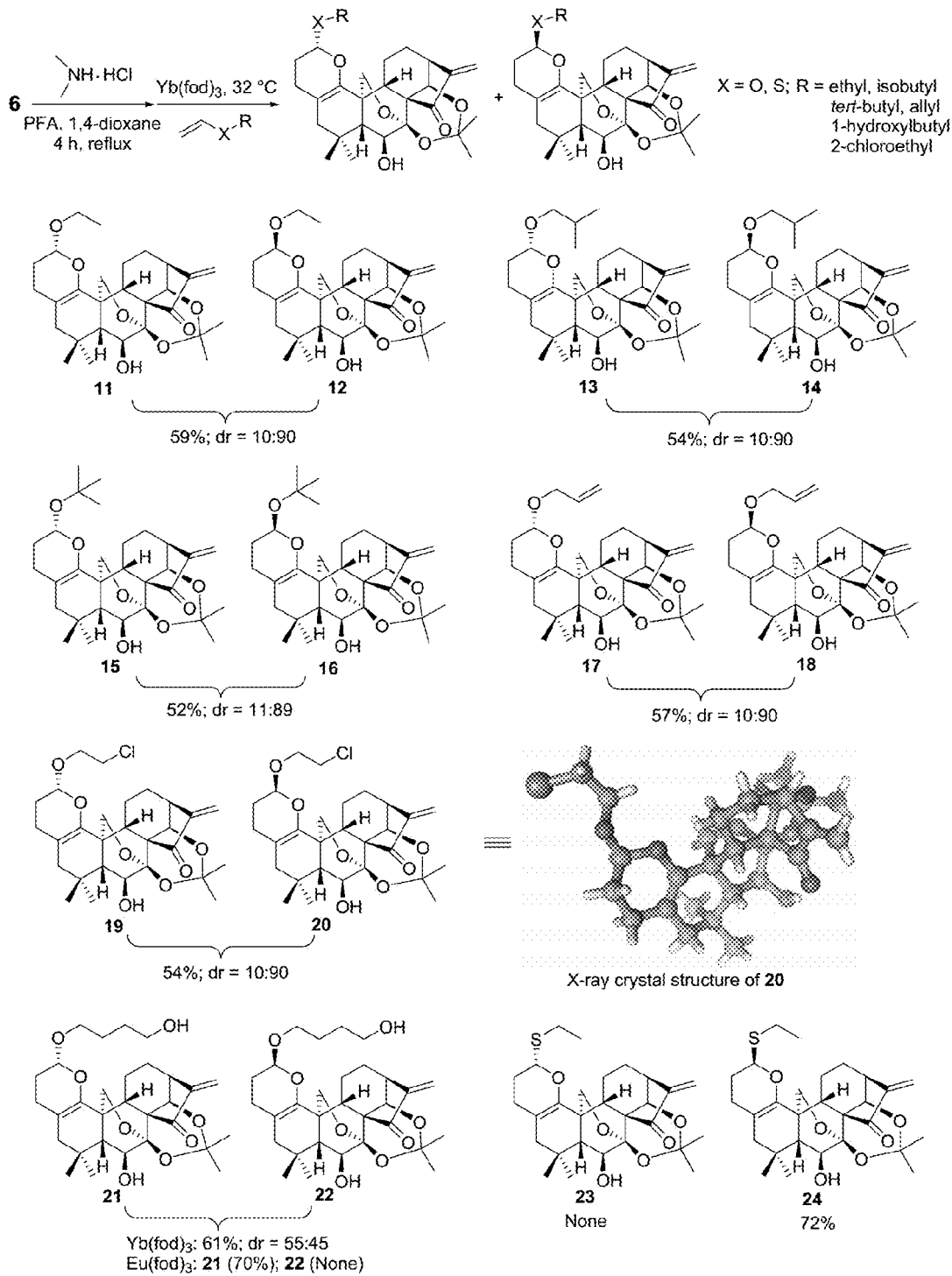
FIG. 12. Illustrates the substrate scope of one-pot cross-HAD reactions with various vinyl ether and vinyl sulfide.

With reference to FIG. 12, a mixture of 6 (50 mg, 0.12 mmol), dimethylammonium chloride (21 mg, 0.26 mmol), and paraformaldehyde (8 mg) in 1,4-dioxane (2 mL) was refluxed for 4 h. The reaction mixture was then diluted with 3 mL of water and extracted with 10 mL of dichloromethane three times. The extract was washed with saturated NaHCO$_3$ (aq) solution (5 mL) and brine (5 mL), dried over anhydrous Na$_2$SO$_4$, filtered, and evaporated to give an oily residue. Without any purification, the residue was directly dissolved in n-butyl vinyl ether (1 mL) in the presence of Yb(fod)$_3$ (11 mg, 0.01 mmol). The resulting mixture was stirred at 32° C. for 72 h. The reaction mixture was then diluted with 3 mL of water and extracted with 10 mL of dichloromethane three times. The extract was washed with brine (5 mL), dried over anhydrous Na$_2$SO$_4$, filtered, and evaporated to give an oily residue. The residue was further purified using preparative TLC developed by 15% EtOAc in hexanes to afford the desired product 11 (3.7 mg) and 12 (34.0 mg) as colorless amorphous gel in total 59% yield (2 steps).

11: $[\alpha]^{25}{}_D$+8 (c 0.10, CH$_2$Cl$_2$). $^1$H NMR (300 MHz, CDCl$_3$): δ 6.14 (s, 1H), 5.54 (s, 1H), 5.30 (d, 1H, J=12.0 Hz), 4.91 (m, 1H), 4.85 (d, 1H, J=1.2 Hz), 4.23 (dd, 1H, J=9.3 Hz, 1.2 Hz), 4.00 (d, 1H, J=9.3 Hz), 3.89 (dd, 1H, J=12.0 Hz, 9.0 Hz), 3.60 (dq, 1H, J=9.3 Hz, 6.9 Hz), 3.44 (dq, 1H, J=9.3 Hz, 6.9 Hz), 3.03 (d, 1H, J=9.6 Hz), 2.48 (m, 1H), 1.86 (m, 9H), 1.65 (s, 3H), 1.51 (m, 2H), 1.34 (s, 3H), 1.16 (s, 3H), 1.14 (t, 3H, J=7.2 Hz), 1.01 (s, 3H). $^{13}$C NMR (75 MHz, CDCl$_3$) δ 204.7, 150.9, 140.8, 119.9, 108.9, 100.9, 95.4, 95.2, 72.1, 70.1, 64.1, 62.9, 59.1, 56.5, 50.1, 45.2, 40.6, 40.3, 32.9, 30.8, 30.6, 30.2, 26.9, 25.3, 22.1, 21.0, 20.6, 15.1. HRMS Calcd for C$_{28}$H$_{38}$O$_7$: [M+H]$^+$ 487.2690; found 487.2682.

12: $[\alpha]^{25}{}_D$+102 (c 0.10, CH$_2$Cl$_2$). $^1$H NMR (300 MHz, CDCl$_3$): δ 6.14 (s, 1H), 5.54 (s, 1H), 5.34 (d, 1H, J=12.0 Hz), 4.86 (d, 1H, J=1.8 Hz), 4.60 (dd, 1H, J=8.7 Hz, 1.8 Hz), 4.18 (d, 1H, J=9.3 Hz), 3.99 (d, 1H, J=9.3 Hz), 3.86 (dd, 1H, J=12.0 Hz, 8.7 Hz), 3.83 (dq, 1H, J=9.6 Hz, 6.9 Hz) 3.53 (dq, 1H, J=9.6 Hz, 7.2 Hz), 2.50 (m, 1H), 1.97 (m, 7H), 1.67 (m, 2H), 1.65 (s, 3H), 1.54 (m, 2H), 1.34 (s, 3H), 1.22 (t, 3H, J=7.2 Hz), 1.17 (s, 3H), 1.03 (s, 3H). $^{13}$C NMR (75 MHz, CDCl$_3$) δ 204.7, 150.9, 142.7, 120.0, 107.5, 100.9, 99.7, 95.4, 72.0, 70.1, 64.4, 63.9, 58.6, 56.4, 49.7, 44.7, 40.6, 40.3, 32.9, 30.8 (2C), 30.1, 28.4, 25.9, 25.3, 21.2, 20.4, 15.2. FIRMS Calcd for C$_{28}$H$_{38}$O$_7$: [M+H]$^+$ 487.2690; found 487.2684.

Example 37

Synthesis of (2R,6aR,7S,7aR,7a$^1$R,10aR,11S,13aS, 13bS)-7-hydroxy-2-isobutoxy-6,6,9,9-tetramethyl-16-methylene-2,3,4,5,6,6a,7,10a,11,12,13,13a-dodecahydro-7a,13b-(epoxy methano)-7a$^1$, 11-ethanol [1,3]dioxino[4',5',6':4,5]naphtho[2, 1-h]chromen-17-one (13) and (2S,6aR,7S,7aR,7a$^1$R,10aR, 11S,13aS, 13bS)-7-hydroxy-2-isobutoxy-6,6,9,9-tetrarnethyl-16-methylene-2,3,4,5,6,6a,7,10a,11,12,13,13a-dodecahydro-7a,13b-(epoxymethano)-7a$^1$,11-ethano [1,3] dioxino[4',5',6':4,5]naphtho[2,1-h] chromen-17-one (14).

With reference to FIG. 12, compounds 13 (3.6 mg) and 14 (31.0 mg) were prepared in 54% yield (2 steps) by a procedure similar to that used to prepare compounds 11 and 12. The title compounds were obtained as colorless amorphous gel.

13: $[\alpha]^{25}{}_D$+8 (c 0.10, CH$_2$Cl$_2$). $^1$H NMR (300 MHz, CDCl$_3$): δ 6.14 (s, 1H), 5.54 (s, 1H), 5.32 (d, 1H, J=12.0 Hz), 4.88 (m, 1H), 4.85 (d, 1H, J=0.9 Hz), 4.23 (d, 1H, J=10.2 Hz), 4.01 (d, 1H, J=9.9 Hz), 3.89 (dd, 1H, J=12.0 Hz, 9.0 Hz), 3.25 (dd, 1H, J=8.7 Hz, 7.2 Hz), 3.15 (dd, 1H, J=8.7 Hz, 6.0 Hz), 3.03 (d, 1H, J=9.0 Hz), 2.48 (m, 1H), 1.83 (m, 9H), 1.66 (s, 3H), 1.56 (m, 3H), 1.35 (s, 3H), 1.16 (s, 3H), 1.00 (s, 3H), 0.85 (d, 6H, J=6.6 Hz). $^{13}$C NMR (75 MHz, CDCl$_3$) δ 204.7, 150.9, 140.7, 119.9, 108.8, 100.9, 95.5, 95.4, 74.4, 72.0, 70.1, 64.2, 59.0, 56.5, 50.1, 45.2, 40.6, 40.3, 32.8, 30.8, 30.6, 30.1, 28.5, 26.8, 25.3, 21.8, 20.9, 20.6, 19.5, 19.3. HRMS Calcd for C$_{30}$H$_{42}$O$_7$: [M+H]$^+$ 515.3003; found 515.3011.

14: $[\alpha]^{25}{}_D$+90 (c 0.10, CH$_2$Cl$_2$). $^1$H NMR (300 MHz, CDCl$_3$): δ 6.14 (s, 1H), 5.54 (s, 1H), 5.34 (d, 1H, J=12.0 Hz), 4.87 (d, 1H, J=1.2 Hz), 4.57 (d, 1H, J=9.0 Hz), 4.17 (d, 1H, J=9.0 Hz), 3.99 (d, 1H, J=9.3 Hz), 3.89 (dd, 1H, J=12.0 Hz, 9.0 Hz), 3.53 (dd, 1H, J=9.3 Hz, 6.6 Hz), 3.20 (dd, 1H, J=9.3 Hz, 6.6 Hz), 3.03 (d, 1H, J=8.4 Hz), 2.50 (m, 1H), 1.94 (m, 9H), 1.66 (s, 3H), 1.53 (m, 3H), 1.34 (s, 3H), 1.17 (s, 3H), 1.03 (s, 3H), 0.91 (dt, 6H, J=0.6 Hz, 6.6 Hz). $^{13}$C NMR (75 MHz, CDCl$_3$) δ 204.7, 150.9, 142.7, 120.0, 107.4, 100.9, 100.0, 95.4, 75.8, 72.0, 70.1, 63.9, 58.6, 56.5, 49.8, 44.7, 40.5, 40.3, 32.8, 30.8 (2C), 30.1, 28.5, 28.3, 25.8, 25.4, 21.2, 20.4, 19.3 (2C). FIRMS Calcd for C$_{30}$H$_{42}$O$_7$: [M+H]$^+$ 515.3003; found 515.2992.

Example 38

Synthesis of (2R,6aR,7S,7aR,7a$^1$R, 10aR,11S,13aS, 13bS)-2-(tert-butoxy)-7-hydroxy-6,6,9,9-tetramethyl-16-methylene-2,3,4,5,6,6a,7,10a, 11,12,13, 13a-dodecahydro-7a,13b-(epoxymethano)-7a$^1$, 11-ethano[1,3] dioxino[4',5',6': 4,5]naphtho[2,1-h] chromen-17-one (15) and (2S,6aR,7S,7aR,7a$^1$R, 10aR,11S,13aS,13bS)-2-(tert-butoxy)-7-hydroxy-6, 6,9,9-tetramethyl-16-methylene-2,3,4,5,6,6a,7,10a, 11,12,13,13a-dodecahydro-7a,13b-(epoxymethano)-7a$^1$,11-ethano[1,3]dioxi no[4',5',6':4,5]naphtho[2,1-h] chromen-17-one (16).

With reference to FIG. 12, compounds 15 (3.5 mg) and 16 (29.6 mg) were prepared in 52% yield (2 steps) by a procedure similar to that used to prepare compounds 11 and 12. The title compounds were obtained as colorless amorphous gel.

15: $[\alpha]^{25}{}_D$+10 (c 0.10, CH$_2$Cl$_2$). $^1$H NMR (300 MHz, CDCl$_3$): δ 6.13 (s, 1H), 5.53 (s, 1H), 5.31 (d, 1H, J=11.7 Hz), 5.19 (s, 1H), 4.84 (s, 1H), 4.18 (d, 1H, J=9.6 Hz), 3.98 (d, 1H, J=9.6 Hz), 3.87 (dd, 1H, J=12.0 Hz, 9.0 Hz), 3.03 (d, 1H, J=9.0 Hz), 2.48 (m, 1H), 2.02 (m, 2H), 1.86 (m, 3H), 1.66 (s, 3H), 1.64 (m, 4H), 1.53 (m, 2H), 1.34 (s, 3H), 1.68 (s, 9H), 1.15 (s, 3H), 1.01 (s, 3H). $^{13}$C NMR (75 MHz, CDCl$_3$) δ 204.7, 151.0, 141.2, 119.8, 108.1, 100.8, 95.3, 89.8, 73.9, 72.0, 70.1, 64.4, 59.1, 56.6, 50.2, 45.4, 40.3 (2C), 32.9, 30.8, 30.5, 30.1, 28.8 (3C), 28.4, 25.4, 21.6, 20.8, 20.6. HRMS Calcd for C$_{30}$H$_{42}$O$_7$: [M+H]$^+$ 515.3003; found 515.3005.

16: [α]$^{25}_D$+96 (c 0.10, CH$_2$Cl$_2$). $^1$H NMR (300 MHz, CDCl$_3$): δ 6.13 (s, 1H), 5.54 (s, 1H), 5.34 (d, 1H, J=12.0 Hz), 4.86 (d, 1H, J=1.5 Hz), 4.75 (dd, 1H, J=2.1 Hz, 9.0 Hz), 4.14 (d, 1H, J=9.6 Hz), 3.98 (d, 1H, J=9.9 Hz), 3.88 (dd, 1H, J=12.0 Hz, 9.0 Hz), 3.03 (d, 1H, J=9.6 Hz), 2.48 (m, 1H), 1.92 (m, 7H), 1.66 (s, 3H), 1.64 (m, 2H), 1.52 (m, 2H), 1.34 (s, 3H), 1.23 (s, 9H), 1.17 (s, 3H), 1.04 (s, 3H). $^{13}$C NMR (75 MHz, CDCl$_3$) δ 204.7, 150.9, 143.2, 119.9, 107.0, 100.9, 95.4, 94.7, 75.0, 72.0, 70.1, 64.2, 58.5, 56.6, 49.9, 44.7, 40.3, 40.3, 32.8, 30.9, 30.7, 30.1, 29.9, 28.8 (3C), 26.7, 25.3, 21.2, 20.7. HRMS Calcd for C$_{30}$H$_{42}$O$_7$: [M+H]$^+$ 515.3003; found 515.3004.

Example 39

Synthesis of (2R,6aR,7S,7aR,7a$^1$R,10aR,11S,13aS, 13bS)-2-(allyloxy)-7-hydroxy-6,6,9,9-tetramethyl-16-methylene-2,3,4,5,6,6a,7,10a, 11,12,13,13 a-dodecahydro-7a,13b-(epoxymethano)-7a$^1$, 11-ethano[1,3]dioxino[4',5',6':4,5]naphtho[2, 1-h]chromen-17-one (17) and (2S,6aR,7S,7aR,7a$^1$R,10aR,11S,13aS, 13bS)-2-(allyloxy)-7-hydroxy-6,6,9,9-tetramethyl-16-methylene-2,3,4,5,6,6a,7,10a,11,12,13,13a-dodecahydro-7a,13b-(epoxymethano)-7a$^1$, 11-ethano[1,3]dioxino[4',5',6',4,5]naphtho[2,1-h]chromen-17-one (18)

With reference to FIG. 12, compounds 17 (3.5 mg) and 18 (31.8 mg) were prepared in 57% yield (2 steps) by a procedure similar to that used to prepare compounds 11 and 12. The title compounds were obtained as colorless amorphous gel.

17: [α]$^{25}_D$−12 (c 0.10, CH$_2$Cl$_2$). $^1$H NMR (300 MHz, CDCl$_3$): δ 6.14 (s, 1H), 5.83 (m, 1H), 5.54 (s, 1H), 5.32 (d, 1H, J=12.0 Hz), 5.24 (dd, 1H, J=17.1 Hz, 1.8 Hz), 5.15 (dd, 1H, J=10.2 Hz, 1.5 Hz), 4.96 (t, 1H, J=1.2 Hz), 4.85 (d, 1H, J=1.2 Hz), 4.23 (dd, 1H, J=9.9 Hz, 0.6 Hz), 4.08 (m, 1H), 4.01 (d, 1H, J=9.9 Hz), 3.95 (m, 1H), 3.90 (dd, 1H, J=12.0 Hz, 8.7 Hz), 3.04 (d, 1H, J=9.0 Hz), 2.49 (m, 1H), 1.86 (m, 9H), 1.65 (s, 3H), 1.52 (m, 2H), 1.34 (s, 3H), 1.16 (s, 3H), 1.00 (s, 3H). $^{13}$C NMR (75 MHz, CDCl$_3$) δ 204.7, 150.9, 140.7, 134.1, 120.0, 116.7, 109.1, 100.9, 95.4, 94.6, 72.0, 70.1, 67.9, 64.1, 59.0, 56.5, 50.0, 45.2, 40.6, 40.3, 32.9, 30.7, 30.6, 30.1, 26.7, 25.3, 21.9, 21.0, 20.5. HRMS Calcd for C$_{29}$H$_{38}$O$_7$: [M+H]$^+$ Exact Mass: 499.2690; found 499.2681.

18: [α]$^{25}_D$+106 (c 0.10, CH$_2$Cl$_2$). $^1$H NMR (300 MHz, CDCl$_3$): δ 6.14 (s, 1H), 5.89 (m, 1H), 5.54 (s, 1H), 5.34 (d, 1H, J=12.0 Hz), 5.28 (dd, 1H, J=17.1 Hz, 1.5 Hz), 5.21 (dd, 1H, J=10.8 Hz, 1.2 Hz), 4.86 (d, 1H, J=0.3 Hz), 4.64 (d, 1H, J=8.4 Hz), 4.27 (dd, 1H, J=12.6 Hz, 5.1 Hz), 4.18 (d, 1H, J=9.3 Hz), 4.05 (dd, 1H, J=12.9 Hz, 6.0 Hz), 3.99 (d, 1H, J=9.9 Hz), 3.89 (dd, 1H, J=12.0 Hz, 9.0 Hz), 3.04 (d, 1H, J=9.3 Hz), 2.49 (m, 1H), 1.95 (m, 7H), 1.71 (m, 2H), 1.66 (s, 3H), 1.54 (m, 2H), 1.34 (s, 3H), 1.17 (s, 3H), 1.03 (s, 3H). $^{13}$C NMR (75 MHz, CDCl$_3$) δ 204.7, 150.9, 142.6, 134.1, 120.0, 117.4, 107.7, 100.9, 99.0, 95.4, 72.0, 70.1, 69.6, 63.9, 58.6, 56.5, 49.7, 44.8, 40.6, 40.3, 32.9, 30.8 (2C), 30.1, 28.2, 25.8, 25.4, 21.3, 20.4. HRMS Calcd for C$_{29}$H$_{38}$O$_7$: [M+H]$^+$ 499.2690; found 499.2691.

Example 40

Synthesis of (2R,6aR,7S,7aR,7a$^1$R,10aR, 11S,13aS, 13bS)-2-(2-chloroethoxy)-7-hydroxy-6,6,9,9-tetramethyl-16-methylene-2,3,4,5,6,6a,7,10a, 11,12,13,13 a-dodecahydro-7a,13b-(epoxymethano)-7a$^1$, 11-ethano[1,3]dioxino[4',5',6':4,5]naphtho[2,1-h]chromen-17-one (19) and (2S,6aR,7S,7aR,7a$^1$R, 10aR,11S,13aS,13bS)-2-(2-chloroethoxy)-7-hydroxy-6,6,9,9-tetramethyl-16-methylene-2,3,4,5,6, 6a,7,10a,11,12,13,13a-dodecahydro-7a,13b-(epoxymethano)-7a$^1$, 11-ethano[1,3]dioxino[4',5',6': 4,5]naphtho[2 -h]chromen-1 7-one (20).

With reference to FIG. 12, compounds 19 (3.5 mg) and 20 (31.4 mg) were prepared in 54% yield (2 steps) by a procedure similar to that used to prepare compounds 11 and 12. The title compounds were obtained as colorless amorphous gel.

19: [α]$^{25}_D$−14 (c 0.10, CH$_2$Cl$_2$). $^1$H NMR (300 MHz, CDCl$_3$): δ 6.14 (s, 1H), 5.54 (s, 1H), 5.31 (d, 1H, J=12.0 Hz), 4.98 (t, 1H, J=2.1 Hz), 4.84 (d, 1H, J=1.5 Hz), 4.21 (dd, 1H, J=9.6 Hz, 1.2 Hz), 4.02 (d, 1H, J=9.3 Hz), 3.89 (dd, 1H, J=12.0 Hz, 8.7 Hz), 3.77 (dt, 1H, J=10.8 Hz, 5.4 Hz), 3.67 (m, 1H), 3.56 (t, 2H, J=5.7 Hz), 3.04 (d, 1H, J=9.3 Hz), 2.49 (m, 1H), 1.87 (m, 9H), 1.65 (s, 3H), 1.52 (m, 2H), 1.34 (s, 3H), 1.16 (s, 3H), 1.01 (s, 3H). $^{13}$C NMR (75 MHz, CDCl$_3$) δ 204.7, 150.9, 140.6, 120.0, 109.3, 100.9, 95.6, 95.4, 72.0, 70.1, 67.7, 64.0, 59.0, 56.5, 50.0, 45.2, 42.7, 40.5, 40.3, 32.9, 30.7, 30.6, 30.1, 26.5, 25.3, 21.6, 21.0, 20.6. HRMS Calcd for C$_{28}$H$_{37}$ClO$_7$: [M+H]$^+$ 521.2301; found 521.2296.

20: [α]$^{25}_D$+96 (c 0.10, CH$_2$Cl$_2$). $^1$H NMR (300 MHz, CDCl$_3$): δ 6.14 (s, 1H), 5.55 (s, 1H), 5.34 (d, 1H, J=12.0 Hz), 4.86 (d, 1H, J=1.2 Hz), 4.66 (dd, 1H, J=9.0 Hz, 1.8 Hz), 4.16 (dd, 1H, J=9.6 Hz, 0.9 Hz), 4.01 (m, 2H), 3.89 (dd, 1H, J=12.3 Hz, 9.0 Hz), 3.76 (m, 1H), 3.63 (t, 2H, J=6.0 Hz), 3.04 (d, 1H, J=9.3 Hz), 2.49 (m, 1H), 1.96 (m, 7H), 1.68 (m, 2H), 1.66 (s, 3H), 1.54 (m, 2H), 1.34 (s, 3H), 1.17 (s, 3H), 1.03 (s, 3H). $^{13}$C NMR (75 MHz, CDCl$_3$) δ 204.7, 150.9, 142.6, 120.1, 107.9, 100.9, 100.1, 95.4, 72.0, 70.1, 69.0, 63.9, 58.6, 56.4, 49.7, 44.7, 42.8, 40.5, 40.3, 32.9, 30.8 (2C), 30.1, 28.1, 25.6, 25.4, 21.2, 20.5. HRMS Calcd for C$_{28}$H$_{37}$ClO$_7$: [M+H]$^+$ 521.2301; found 521.2291.

Example 41

Synthesis of (2R,6aR,7S,7aR, 7a$^1$R,10aR,11S,13aS, 13bS)-7-hydroxy -2-(4-hydroxybutoxy)-6,6,9,9-tetramethyl-16-methylene-2,3,4,5,6,6a,7,10a, 11,12, 13,13 a-dodecahydro-7a,13b-(epoxymethano)-7a$^1$, 11-ethano[1,3]dioxino[4',5',6':4,5]n aphtho[2, 1-h] chromen-17-one (21) and (2S,6aR,7S,7aR,7a$^1$R, 10aR,11S,13aS,13bS)-7-hydroxy-2-(4-hydroxybutoxy)-6,6,9,9-tetramethyl-16-methylene-2,3,4,5,6,6a, 7,10a,11,12,13,13a-dodecahydro-7a,13b-(epoxymethano)-7a$^1$,11-ethano[1.,3]dioxino[4',5',6∝: 4,5]naphtho[2 1-h]chromen-17-one (22)

With reference to FIG. 12, compounds 21 (22.3 mg) and 22 (17.9 mg) were prepared in 61% yield (2 steps) by a procedure similar to that used to prepare compounds 11 and 12. The title compounds were obtained as colorless amorphous gel.

21: [α]$^{25}_D$ +8 (c 0.10, CH$_2$Cl$_2$). $^1$H NMR (300 MHz, CDCl$_3$): δ 6.14 (s, 1H), 5.54 (s, 1H), 5.32 (d, 1H, J=12.0 Hz), 4.91 (t, 1H, J=2.1 Hz), 4.84 (s, 1H), 4.22 (d, 1H, J=8.4 Hz), 4.00 (d, 1H, J=9.3 Hz), 3.89 (dd, 1H, J=12.0 Hz, 8.4

Hz), 3.62 (m, 3H), 3.44 (m, 1H), 3.03 (d, 1H, J=9.3 Hz), 2.49 (m, 1H), 1.87 (m, 9H), 1.65 (s, 3H), 1.62 (m, 5H), 1.52 (m, 2H), 1.34 (s, 3H), 1.16 (s, 3H), 1.01 (s, 3H). $^{13}$C NMR (75 MHz, CDCl$_3$) δ 204.7, 150.9, 140.7, 120.0, 108.9, 100.9, 95.5, 95.4, 72.0, 70.1, 67.6, 64.1, 62.6, 59.0, 56.5, 50.0, 45.2, 40.6, 40.3, 32.9, 30.7, 30.6, 30.1, 30.0, 26.7, 26.4, 25.3, 21.8, 21.0, 20.6. HRMS Calcd for C$_{30}$H$_{42}$O$_8$: [M+H]$^+$ 531.2952; found 531.2944.

22: $[α]^{25}_D$+72 (c 0.10, CH$_2$Cl$_2$). $^1$H NMR (300 MHz, CDCl$_3$): δ 6.14 (s, 1H), 5.55 (s, 1H), 5.35 (d, 1H, J=12.0 Hz), 4.86 (d, 1H, J=0.9 Hz), 4.60 (dd, 1H, J=9.0 Hz, 1.2 Hz), 4.17 (d, 1H, J=9.6 Hz), 3.99 (d, 1H, J=9.9 Hz), 3.89 (dd, 1H, J=12.0 Hz, 9.0 Hz), 3.83 (m, 1H), 3.66 (m, 2H), 3.50 (m, 1H), 3.04 (d, 1H, J=9.3 Hz), 2.50 (m, 1H), 1.94 (m, 8H), 1.66 (m, 9H), 1.54 (m, 2H), 1.34 (s, 3H), 1.17 (s, 3H), 1.03 (s, 3H). $^{13}$C NMR (75 MHz, CDCl$_3$) δ 204.8, 150.9, 142.7, 120.1, 107.8, 100.9, 99.8, 95.4, 72.0, 70.1, 68.9, 63.9, 62.6, 58.6, 56.5, 49.7, 44.7, 40.6, 40.3, 32.9, 30.8 (2C), 29.8, 28.3, 26.4, 25.8, 25.4, 21.2, 20.5. HRMS Calcd for C$_{30}$H$_{42}$O$_8$: [M+H]$^+$ 531.2952; found 531.2943.

When the reaction was catalyzed by Eu(fod)$_3$ at rt, 21 (43.4 mg) was obtained in 70% yield (2 steps) as the sole product.

Example 42

Synthesis of (2R,6aR,7S,7aR,7a$^1$R, 10aR,11S,13aS, 13b,S)-2-(ethylthio)-7-hydroxy-6,6,9,9-tetramethyl-16-methylene-2,3,4,5,6,6a,7, 10a, 11,12,13,13 a-dodecahydro-7a,13b-(epoxymethano)-7a$^1$, 11-ethano[1,3]dioxino[4',5',6':4,5]naphtho[2, 1-h]chromen-17-one (24)

With reference to FIG. 12, compound 24 (45 mg) was prepared in 72% yield (2 steps) by a procedure similar to that used to prepare compounds 11 and 12. The title compound was obtained as a colorless amorphous gel. $[α]^{25}_D$+112 (c 0.10, CH$_2$Cl$_2$). $^1$H NMR (300 MHz, CDCl$_3$): δ 6.14 (s, 1H), 5.55 (d, 1H, J=0.3 Hz), 5.34 (d, 1H, J=12.0 Hz), 4.86 (d, 1H, J=1.2 Hz), 4.75 (dd, 1H, J=9.9 Hz, 1.8 Hz), 4.16 (dd, 1H, J=9.6 Hz, 1.5 Hz), 3.99 (d, 1H, J=9.6 Hz), 3.89 (dd, 1H, J=12.0 Hz, 8.7 Hz), 3.03 (dd, 1H, J=9.6 Hz, 0.9 Hz), 2.67 (m, 2H), 2.50 (m, 1H), 1.97 (m, 9H), 1.65 (s, 3H), 1.55 (m, 2H), 1.34 (s, 3H), 1.28 (t, 3H, J=7.2 Hz), 1.17 (s, 3H), 1.04 (s, 3H). $^{13}$C NMR (75 MHz, CDCl$_3$) δ 204.7, 150.9, 144.6, 120.0, 107.8, 100.8, 95.4, 80.1, 72.0, 70.0, 63.8, 58.7, 56.4, 49.7, 45.0, 40.6, 40.3, 32.8, 30.8, 30.7, 30.1, 28.8, 26.7, 25.3, 24.7, 21.2, 20.4, 15.0. FIRMS Calcd for C$_{28}$H$_{38}$O$_6$S: [M+H]$^+$ 503.2462; found 503.2449.

Example 43

Synthesis of (3aR,3a$^1$R,4S,4aR,7aS, 11aR,12bS, 12cS,15S,15aR)-4-hydroxy-2,2,5,5-tetramethyl-16-methylene-4a, 5,6,7,7a,8,9,10,11a,12c,13,14,15,15a-tetradecahydro-4H-3a,12b-(epoxymethano)-3a$^1$,15-ethano[1,3]dioxino[4',5',6':4,5]naphtho[2,1-h]pyrano[2,3-b]chromen-17-one (27)

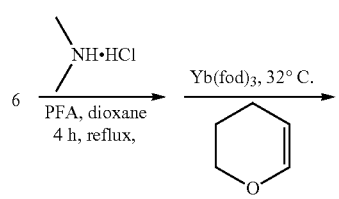

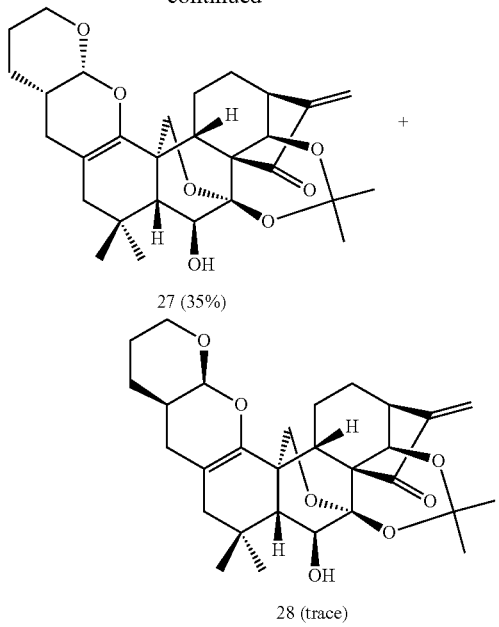

27 (35%)

28 (trace)

Compound 27 (21 mg) was prepared in 35% yield (2 steps) by a procedure similar to that used to prepare compounds 11 and 12. The title compound was obtained as a colorless amorphous gel. $[α]^{25}_D$+8 (c 0.10, CH$_2$Cl$_2$). $^1$H NMR (300 MHz, CDCl$_3$): δ 6.15 (d, 1H, J=0.6 Hz), 5.55 (d, 1H, J=0.6 Hz), 5.34 (d, 1H, J=12.0 Hz), 4.88 (d, 1H, J=2.1 Hz), 4.85 (d, 1H, J=1.2 Hz), 4.29 (dd, 1H, J=9.9 Hz, 1.5 Hz), 3.99 (d, 1H, J=9.6 Hz), 3.89 (dd, 1H, J=12.0 Hz, 9.0 Hz), 3.75 (m, 1H), 3.65 (dt, 1H, J=11.1 Hz, 4.2 Hz), 3.04 (d, 1H, J=9.6 Hz), 2.52 (m, 1H), 2.01 (m, 6H), 1.65 (m, 7H), 1.51 (m, 4H), 1.34 (s, 3H), 1.17 (s, 3H), 1.02 (s, 3H). $^{13}$C NMR (75 MHz, CDCl$_3$)δ 204.8, 150.9, 142.0, 120.0, 106.1, 100.9, 96.5, 95.3, 72.1, 70.1, 64.0, 62.6, 58.9, 56.6, 50.0, 44.8, 40.6, 40.4, 32.9, 32.8, 32.1, 30.8 (2C), 30.2, 25.4, 24.3, 24.0, 21.1, 20.7. HRMS Calcd for C$_{29}$H$_{38}$O$_7$: [M+H]$^+$ 499.2690; found 499.2686.

Example 44

Synthesis of (2R,6aR;7S,7aR,7a$^1$R,10aR,11S,13aS, 13bS)-2-(4-azidobutoxy)-7-dodecahydro-7a,13b-(epoxymethano)-7a$^1$,11-ethano[1,3]dioxino[4',5',6':4, 5]naphtho[2,1-h]chromen-17-one (26)

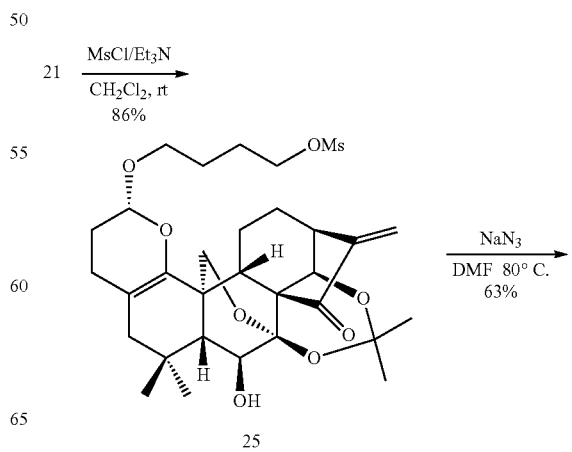

25

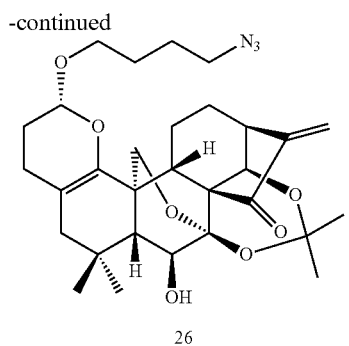

26

To a solution of compound 21 (61 mg, 0.12 mmol) in dichloromethane was added Et$_3$N (35 mg, 0.35 mmol) and MSCl (20 mg, 0.17 mmol) dropwise at 0° C. The mixture was stirred at rt overnight, and diluted with water and extracted with dichloromethane. The organic extract was washed with brine, dried over anhydrous Na$_2$SO$_4$, filtered, and evaporated to give an oily residue. The residue was further purified using preparative TLC developed by 25% EtOAc in hexanes to afford the desired product 25 as a colorless gel (62 mg, 86%). $^1$H NMR (300 MHz, CDCl$_3$): δ 6.14 (s, 1H), 5.54 (s, 1H), 5.32 (d, 1H, J=12.0 Hz), 4.89 (t, 1H, J=2.1 Hz), 4.85 (d, 1H, J=1.5 Hz), 4.23 (m, 3H), 3.98 (d, 1H, J=9.3 Hz), 3.88 (dd, 1H, J=12.0 Hz, 9.0 Hz), 3.58 (dt, 1H, J=9.3 Hz, 6.3 Hz), 3.44 (dt, 1H, J=9.3 Hz, 5.7 Hz), 3.01 (d, 1H, J=6.3 Hz), 3.00 (s, 3H), 2.48 (m, 1H), 1.90 (m, 9H), 1.66 (m, 8H), 1.52 (m, 2H), 1.34 (s, 3H), 1.16 (s, 3H), 1.00 (s, 3H). $^{13}$C NMR (75 MHz, CDCl$_3$) δ 204.7, 150.9, 140.7, 120.0, 108.9, 100.9, 95.5, 95.4, 72.0, 70.1, 69.7, 66.8, 64.1, 59.0, 56.5, 50.0, 45.2, 40.6, 40.3, 37.4, 32.9, 30.8, 30.6, 30.1, 26.7, 26.4, 25.7, 25.3, 21.9, 21.0, 20.6. HRMS Calcd for C$_{31}$H$_{44}$O$_{10}$S: [M+H]$^+$ 609.2728; found 609.2717.

A mixture of 25 (30 mg, 0.05 mmol) and NaN$_3$ (10 mg, 0.15 mmol) in the dried DMF (2 mL) was stirred at 65° C. under N$_2$ for 16 h. After the completion of the reaction, which was monitored by TLC, the mixture was diluted with water and extracted with dichloromethane. The organic extract was washed with brine, dried over anhydrous Na$_2$SO$_4$, filtered, and evaporated to give an oily residue, which was further purified using preparative TLC developed by 20% EtOAc in hexanes to afford the desired product 26 (16.8 mg, 63%) as a colorless amorphous gel. 1H NMR (300 MHz, CDCl$_3$): δ 6.14 (s, 1H), 5.54 (d, 1H, J=0.3 Hz), 5.32 (d, 1H, J=12.0 Hz), 4.90 (t, 1H, J=2.1 Hz), 4.84 (d, 1H, J=1.5 Hz), 4.22 (dd, 1H, J=9.3 Hz, 1.2 Hz), 3.99 (d, 1H, J=9.6 Hz), 3.89 (dd, 1H, J=9.0 Hz, 12.0 Hz), 3.56 (m, 1H), 3.42 (m, 1H), 3.27 (m, 2H), 3.04 (d, 1H, J=9.6 Hz), 2.49 (m, 1H), 1.88 (m, 9H), 1.64 (m, 8H), 1.52 (m, 2H), 1.34 (s, 3H), 1.16 (s, 3H), 1.01 (s, 3H). $^{13}$C NMR (75 MHz, CDCl$_3$) δ 204.7, 150.9, 140.7, 120.0, 109.0, 101.0, 95.5, 95.4, 72.1, 70.1, 67.0, 64.2, 59.0, 56.5, 51.3, 50.1, 45.2, 40.6, 40.3, 32.9, 30.8, 30.6, 30.2, 26.9, 26.8, 26.1, 25.4, 21.9, 21.0, 20.6. HRMS Calcd for C$_{30}$H$_{41}$N$_3$O$_7$: [M+H]$^+$ 556.3017; found 556.3010.

Example 45

Synthesis of (2R,6aR,7S,8S,8aR,11S,13aS,13bS,16R)-2-ethoxy-7,8,16-trihydroxy-6,6-dimethyl-10-methylene-3,4,5,6,6a,7,8,10,11,12,13,13a-dodecahydro-8,13b-(epoxymethano)-8a,11-methanocyclohepta[3,4]benzo[1,2-h]chromen-9(2H)-one (29) and 3-((2R,4aR,5S,6S,6aR,9S,11aS,11bS,14R)-5,6,14-trihydroxy-4,4-dimethyl-8-methylene-1,7-dioxododecahydro-1H-6,11b-(epoxymethano)-6a,9-methanocyclohepta[α]naphthalen-2-yl)propanal (31).

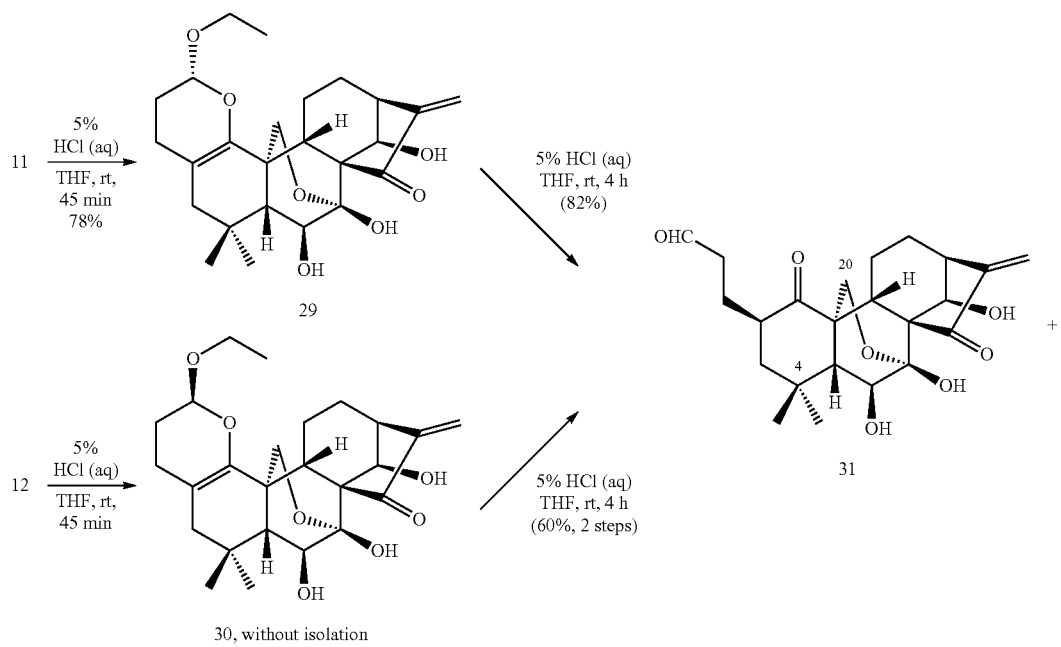

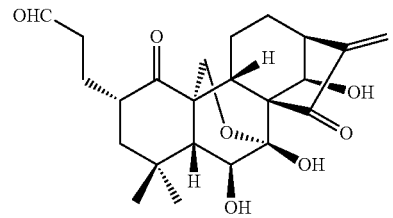

32 (None)

To a solution of 11 (10 mg, 0.02mmol) in THF (1.0 mL) was added 5% HCl aqueous solution (0.4 mL) at rt. The resulting mixture was stirred at rt for 45 min, and then diluted with water and extracted with dichloromethane. The extract was washed with saturated NaHCO$_3$ (aq) solution and brine, dried over anhydrous Na$_2$SO$_4$, filtered, and evaporated to give an oily residue. The residue was purified using preparative TLC developed by 2.5% methanol in dichloromethane to afford the desired product 29 (7.2 mg, 78%) as a colorless amorphous gel. $[\alpha]^{25}_D$+12 (c 0.10, CH$_2$Cl$_2$). $^1$H NMR (300 MHz, CDCl$_3$): δ 6.18 (s, 1H), 5.87 (dd, 1H, J=12.0 Hz, 4.2 Hz), 5.56 (s, 1H), 5.11 (m, 1H), 4.92 (s, 2H), 4.69 (s, 1H), 4.27 (dd, 1H, J=9.6 Hz, 0.9 Hz), 3.99 (d, 1H, J=9.9 Hz), 3.79 (dd, 1H, J=12.0 Hz, 9.0 Hz), 3.59 (dq, 1H, J=9.6 Hz, 6.9 Hz), 3.44 (dq, 1H, J=9.6 Hz, 6.9 Hz), 3.02 (d, 1H, J=9.9 Hz), 2.44 (m, 1H), 1.97 (m, 4H), 1.78 (m, 2H), 1.67 (m, 3H), 1.52 (m, 2H), 1.15 (t, 3H, J=7.2 Hz), 1.13 (s, 3H), 1.00 (s, 3H). $^{13}$C NMR (75 MHz, CDCl$_3$) δ 206.6, 151.6, 140.5, 120.9, 109.7, 97.7, 95.2, 73.5, 72.0, 64.7, 63.0, 62.5, 58.5, 53.3, 45.1, 42.6, 41.4, 33.0, 30.4, 30.2, 26.9, 22.2, 20.7, 20.5, 15.1. HRMS Calcd for C$_{25}$H$_{34}$O$_7$: [M+H]$^+$ 447.2377; found 447.2380.

To a solution of 29 (5.0 mg, 0.01mmol) in THF (1.0 mL) was added 5% HCl aqueous solution (0.2 mL) at rt. The resulting mixture was stirred at rt for 4 h, and then diluted with water and extracted with dichloromethane. The extract was washed with saturated NaHCO$_3$ (aq) solution and brine, dried over anhydrous Na$_2$SO$_4$, filtered, and evaporated to give an oily residue. The residue was purified using preparative TLC developed by 3% methanol in dichloromethane to afford the desired product 31 (3.8 mg, 82%) as a colorless amorphous gel. $[\alpha]^{25}_D$+172 (c 0.10, CH$_2$Cl$_2$). $^1$H NMR (300 MHz, CDCl$_3$): δ 9.71 (t, 1H, J=1.5 Hz), 6.26 (s, 1H), 5.89 (d, 1H, J=11.7 Hz), 5.65 (s, 1H), 5.41 (br s, 1H), 4.85 (s, 1H), 4.54 (br s, 1H), 4.34 (d, 1H, J=10.2 Hz), 4.01 (dd, 1H, J=10.5 Hz, 1.2 Hz), 3.78 (dd, 1H, J=12.0 Hz, 9.0 Hz), 3.06 (d, 1H, J=9.3 Hz), 2.59 (m, 1H), 2.43 (m, 3H), 2.13 (m, 3H), 1.88 (m, 2H), 1.65 (m, 1H), 1.55 (m, 1H), 1.28 (m, 1H), 1.18 (s, 3H), 0.98 (m, 1H), 0.92 (s, 3H). $^{13}$C NMR (75 MHz, CDCl$_3$) δ 212.9, 206.3, 201.7, 150.7, 122.3, 98.2, 73.3, 71.9, 64.5, 61.5, 59.0, 50.2, 48.9, 46.6, 42.6 (2C), 41.2, 32.7, 30.7, 29.4, 24.7, 21.9, 19.0. HRMS Calcd for C$_{23}$H$_{30}$O$_7$: [M+H]$^+$ 419.2064; found 419.2071.

To a solution of 12 (5.0 mg, 0.01mmol) in THF (1.0 mL) was added 5% HCl aqueous solution (0.3 mL) at rt. The resulting mixture was stirred at rt for 5 h, and then diluted with water and extracted with dichloromethane. The extract was washed with saturated NaHCO$_3$ (aq) solution and brine, dried over anhydrous Na$_2$SO$_4$, filtered, and evaporated to give an oily residue. The residue was purified using preparative TLC developed by 3% methanol in dichloromethane to afford the desired product 31 (2.5 mg, 60%) as a colorless amorphous gel.

Example 46

(1aR,3aR,4S,4aR,4a$^1$R,7aR,8S, 10aS,10bS, 10cS)-4-hydroxy-3,3,6,6-tetramethyl-3-methylenedecahydro-1aH-4a, 10b-epoxymethano)-4a$^1$, 8-ethanooxireno[2',3':5,6]phenanthro[1,1 0-de] [1,3]dioxin-14-one (CYD-7-9)

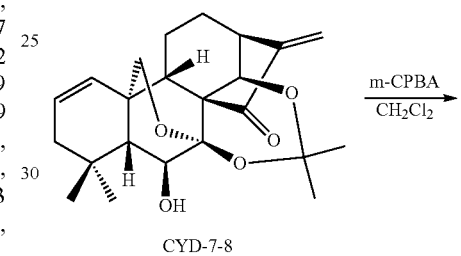

CYD-7-8

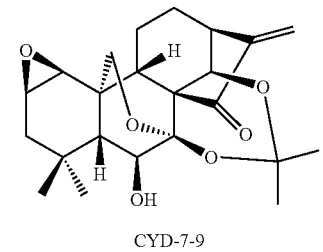

CYD-7-9

To solution of CYD-7-8 (16 mg, 0.04 mmol) in dichloromethane (4 mL) was added m-CPBA (9.0 mg, 0.04 mmol) at 0° C. The resulting mixture was stirred at rt for 1 h. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to give an oily residue. The residue was further purified using preparative TLC developed by 50% EtOAc in hexane to afford the desired product CYD-7-9 as a colorless gel (13 mg, 78%).$^1$H NMR (600 MHz, CDCl$_3$) δ 6.18 (s, 1H), 5.90 (s, 1H), 5.58 (br s, 1H), 4.83 (s, 1H), 4.14 (d, 1H, J=9.6 Hz), 4.02 (d, 1H, J=9.6 Hz), 3.82 (br s, 1H), 3.25 (br s, 1H), 3.08 (d, 1H, J=9.0 Hz), 2.58 (m, 1H), 2.55 (m, 1H), 2.09 (m, 1H), 1.83 (m, 3H), 1.72 (m, 1H), 1.65 (s, 3H), 1.52 (d, 1H, J=15.0 Hz), 1.34 (s, 3H), 1.19 (d, 1H, J=7.8 Hz), 1.08 (s, 3H), 1.04 (s, 3H). $^{13}$C NMR (150 MHz, CDCl$_3$) δ 204.4, 150.2, 120.7, 101.4, 95.3, 71.9, 70.0, 64.9, 55.7, 54.4, 53.1, 52.3, 45.5, 40.4, 40.2, 36.0, 32.4, 30.3, 30.1 (2C), 25.5, 23.5, 16.6.

Example 47

(1aR,3aR,4S,5S,5aR,8S,10aS, 10bS, 10cS,13R)-4,5, 13-trihydroxy-3,3-dimethyl-7-methylenedecahydro-1aH-5,10b-(epoxymethano)-5a,8-methanocyclohepta[7,8]naphtho[,2-b]oxiren-6(2H)-one (CYD-7-23-1) and (1S,2S,4aR,5S,6S,6aR,9S,11aS,11bS,14R)-1,2,5, 6,14-pentahydroxy-4,4-dimethyl-8-methylenedecahydro-1H-6,11b-(epoxymethano)-6a,9-methanocyclohepta[a]naphthalen-7(8H)-one (CYD-7-23-2)

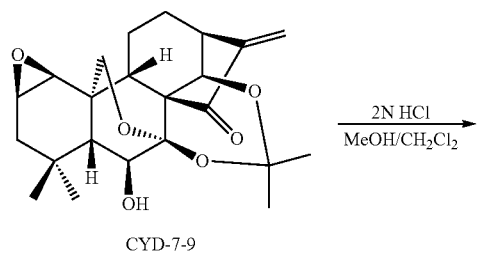

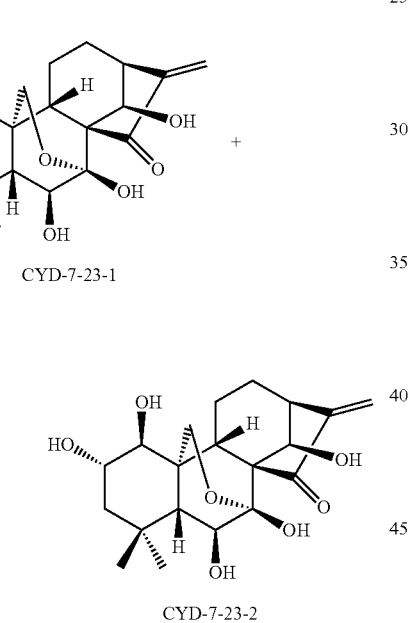

To a solution of CYD-7-9 (10 mg, 0.024 mmol) in a mixture of MeOH (2 mL) and CH$_2$Cl$_2$ (0.5 mL) was added 5% HCl aqueous solution (0.5 mL) at rt. The resulting mixture was stirred at rt for 2 hrs. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to give an oily residue. The residue was purified using preparative TLC developed by 10% methanol in dichloromethane to afford the desired product CYD-7-23-1 (4 mg, 44.4%) as a colorless gel and CYD-7-23-2 (5 mg, 52.8%) as a white solid, respectively. It was noted that longer reaction time resulted in CYD-7-23-2 as solely product. CYD-7-23-1: $^1$H NMR (600 MHz, CDCl$_3$) δ 6.21 (s, 1H), 6.04 (d, 1H, J=12.0 Hz), 5.60 (d, 1H, J=0.9 Hz), 5.18 (br s, 1H), 4.90 (d, 1H, J=0.9 Hz), 4.46 (br s, 1H), 4.10 (m, 2H), 3.69 (dd, 1H, J=8.4 Hz, 11.7 Hz), 3.25 (m, 1H), 3.06 (m, 1H), 2.58 (d, 1H, J=4.2 Hz), 2.50 (m, 1H), 2.05 (m, 1H), 1.76 (m, 4H), 1.52 (m, 1H), 1.20 (dd, 1H, J=0.6 Hz, 8.1 Hz), 1.05 (s, 3H), 1.02 (s, 3H). $^{13}$C NMR (150 MHz, CDCl$_3$) δ 206.3, 150.9, 121.6, 97.6, 73.5, 72.0, 65.6, 61.7, 53.8, 53.3, 52.6, 48.9, 42.8, 40.0, 36.6, 32.4, 30.0, 29.6, 23.2, 16.8.

CYD-7-23-2: $^1$H NMR (600 MHz, CD$_3$OD+CD$_3$Cl) δ 6.16 (s, 1H), 5.58 (s, 1H), 4.89 (d, 1H, J=1.2 Hz), 4.74 (dd, 1H, J=1.8 Hz, 10.2 Hz), 4.44 (br s, 1H), 4.17 (m, 1H), 4.00 (d, 1H, J=1.2 Hz, 10.2 Hz), 3.85 (d, 1H, J=6.0 Hz), 3.50 (d, 1H, J=2.4 Hz), 3.04 (d, 1H, J=9.6 Hz), 2.54 (m, 1H), 2.26 (dd, 1H, J=4.2 Hz, 15.0 Hz), 2.20 (m, 1H), 1.87 (m, 1H), 1.79 (m, 2H), 1.67 (m, 2H), 1.38 (s, 3H), 1.13 (s, 3H).

Example 48

(1aR,2R,3aR,4S,4aR,4a$^1$R,7aR,8S,10aS,10bS,10cS)-2,4-dihydroxy-3,3,6,6-tetramethyl-13-methylenedecahydro-1aH-4a,10-(epoxymethano)-4a$^1$,8-ethanooxireno[2',3':5,6]phenanthro[1,10-de][1,3]dioxin-14-one (CYD-7-19)

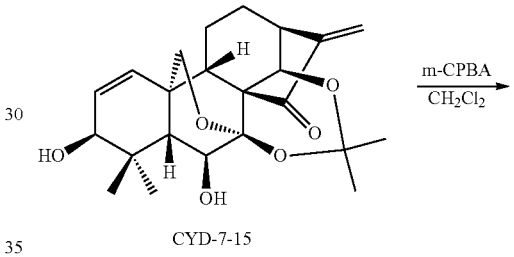

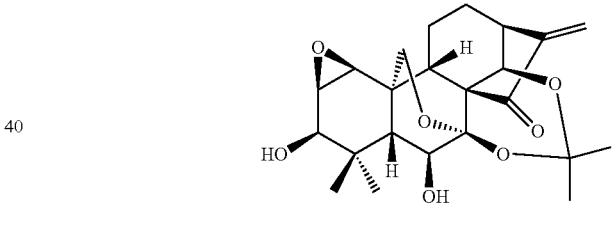

To a solution of CYD-7-15 (20 mg, 0.049 mmol) in dichloromethane (4 mL) was added m-CPBA (9.4 mg, 0.054 mmol) at 0° C. The resulting mixture was stirred at rt for 1 h. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to give an oily residue. The residue was further purified using preparative TLC developed by EtOAc to afford the desired product CYD-7-19 as a colorless gel (15 mg, 72%). $^1$H NMR (600 MHz, CD$_3$Cl) δ 6.20 (s, 1H), 5.61 (d, 1H, J=0.6 Hz), 5.44 (d, 1H, J=12.6 Hz), 4.82 (d, 1H, J=1.2 Hz), 4.11 (m, 1H), 4.01 (m, 1H), 3.83 (m, 1H), 3.60 (m, 1H), 3.54 (m, 1H), 3.10 (d, 1H, J=9.0 Hz), 2.83 (d, 1H, J=3.6 Hz), 2.58 (m, 1H), 2.17 (m, 1H), 2.04 (m, 1H), 1.84 (m, 2H), 1.70 (m, 1H), 1.65 (s, 3H), 1.35 (s, 3H), 1.14 (s, 3H), 0.98 (s, 3H). $^{13}$C NMR (150 MHz, CDCl$_3$) δ 204.2, 150.1, 121.0, 101.4, 95.3, 71.5, 70.9, 69.9, 64.7, 55.6 (2C), 47.2, 45.6, 40.3, 37.3, 35.9, 30.1 (2C), 25.5, 25.1, 21.4, 16.6.

Example 49

(1aR,2R,3aR,4S,5S,5aR,8S,10aS,10bS,10cS,13R)-2,4,5,13-tetrahydroxy-3,3-dimethyl-7-methylenedecahydro-1aH-5,10b-(epoxymethano)-5a,8-methanocyclohepta[7,8]naphtho[1,2-]oxiren-6(2H)-one (CYD-7-27)

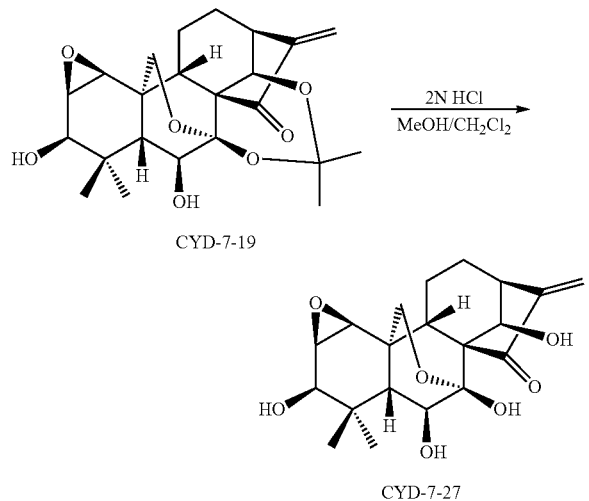

To a solution of CYD-7-19 (12 mg, 0.028 mmol) in a mixture of MeOH (2 mL) and CH$_2$Cl$_2$ (0.5 mL) was added 5% HCl aqueous solution (0.5 mL) at rt. The resulting mixture was stirred at rt for 2 hrs. After that, the reaction mixture was diluted with water and extracted with dichloromethane. The extract was washed with saturated NaHCO$_3$ (aq.) solution and brine, dried over anhydrous Na$_2$SO$_4$, filtered, and evaporated to give an oily residue. The residue was purified using preparative TLC developed by 5% methanol in dichloromethane to afford the desired product CYD-7-27 (8 mg, 74%) as colorless gel. $^1$H NMR (600 MHz, CD$_3$Cl) δ 6.23 (s, 1H), 6.04 (d, 1H, J=12.0 Hz), 5.63 (d, 1H, J=0.6 Hz), 5.37 (br s, 1H), 5.30 (s, 1H), 4.90 (d, 1H, J=1.2 Hz), 4.52 (br s, 1H), 4.12 (dd, 1H, J=1.8 Hz, 10.2 Hz), 4.04 (dd, 1H, J=1.2 Hz, 10.2 Hz), 3.72 (dd, 1H, J=8.4 Hz, 12.0 Hz), 3.62 (dd, 1H, J=6.0 Hz, 8.4 Hz), 3.55 (dd, 1H, J=3.6 Hz, 6.0 Hz), 3.08 (d, 1H, J=9.0 Hz), 2.83 (d, 1H, J=3.6 Hz), 2.52 (m, 1H), 2.19 (d, 1H, J=8.4 Hz), 2.02 (m, 1H), 1.90 (m, 1H), 1.72 (m, 3H), 1.37 (d, 1H, J=8.4 Hz), 1.11 (s, 3H), 0.98 (s, 3H). $^{13}$C NMR (150 MHz, CDCl$_3$) δ 206.2, 150.7, 121.9, 97.6, 73.0, 72.1, 70.6, 65.3, 61.6, 55.8, 55.7, 48.9, 46.8, 42.7, 37.3, 36.5, 29.5, 24.7, 21.1, 16.7.

Example 50

(3S,3aR,3a$^1$R,6aR,7S,7aR,10S,11S,11aS,11bS)-10-azido-7,11-dihydroxy-5,5,8,8-tetramethyl-15-methylenedecahydro-1H-6a,11a-(epoxymethano)-3,3 a$^1$-ethanophenanthro[1,10-de] [1,3]dioxin-14-one (CYD-7-42)

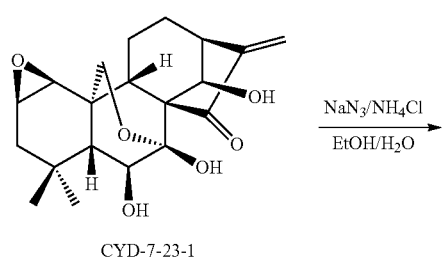

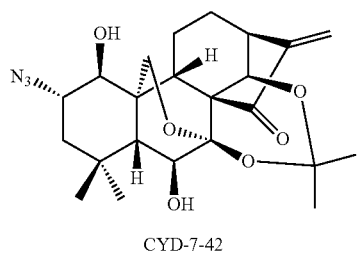

To a solution of CYD-7-23-1 (25 mg, 0.062 mmol) in a mixture of ethanol (2 mL) and water (2 mL) was added NH$_4$Cl (7 mg, 0.124 mmol) and NaN$_3$ (32 mg, 0.496 mmol) at rt. The resulting mixture was stirred at 85° C. for 16 hrs. After that, the reaction mixture was diluted with water and extracted with dichloromethane. The extract was washed with brine, dried over anhydrous Na$_2$SO$_4$, filtered, and evaporated to give an oily residue. The residue was purified using preparative TLC developed by 5% ethyl acetate in dichloromethane to afford the desired product CYD-7-42 (10 mg, 64%), and 11 mg of CYD-7-23-1 was recovered. $^1$H NMR (600 MHz, CD$_3$Cl) δ 6.19 (s, 1H), 6.02 (d, 1H, J=12.0 Hz), 5.59 (s, 1H), 4.78 (s, 1H), 4.48 (d, 1H, J=10.2 Hz), 3.99 (dd, 1H, J=7.2 Hz, 12.0 Hz), 3.83 (m, 2H), 3.36 (s, 1H), 3.09 (d, 1H, J=9.0 Hz), 2.54 (m, 1H), 2.25 (m, 1H), 1.96 (m, 2H), 1.77 (m, 2H), 1.68 (m, 2H), 1.66 (s, 3H), 1.62 (d, 1H, J=6.6 Hz), 1.37 (s, 3H), 1.35 (s, 3H), 1.23 (s, 3H).

Example 51

(3S,3aR,3a$^1$R,6aR,7S,7aR,10S,11S,11aS,11bS)-7,11-dihydroxy-5,5,8,8-tetramethyl-15-methylene-10-(4-phenyl-1/1-1,2,3-triazol-1-yl)decahydro-1H-6a,11a-(epoxymethano)-3,3 a$^1$-ethanophenanthro[1,10-de] [1,3]dioxin-14-one (CYD-7-54)

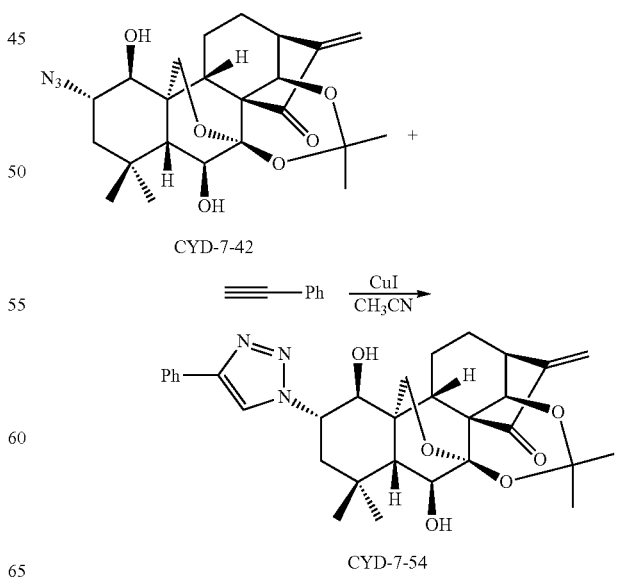

Copper (I) iodide (3.8 mg, 0.02 mmol) was added to a solution of CYD-7-42 (9 mg, 0.02 mmol) and phenyl acetylene (2.4 mg, 0.024 mmol) in acetonitrile (2 mL). The reaction mixture was stirred at rt for 16 hrs. After that, the reaction mixture was diluted with water and extracted with dichloromethane. The extract was washed with brine, dried over anhydrous $Na_2SO_4$, filtered, and evaporated to give an oily residue. The residue was purified using preparative TLC developed by 5% ethyl acetate in dichloromethane to afford the desired product CYD-7-54 (4 mg, 65%), and 4 mg of CYD-7-42 was recovered. $^1$H NMR (600 MHz, $CD_3Cl$) δ 7.75 (m, 3H), 7.39 (m, 3H), 6.19 (s, 1H), 5.59 (s, 1H), 5.57 (d, 1H, J=12.0 Hz), 4.82 (d, 1H, J=1.2 Hz), 4.60 (m, 1H), 4.43 (m, 1H), 4.00 (m, 3H), 3.07 (d, 1H, J=9.0 Hz), 2.99 (m, 1H), 2.50 (m, 1H), 2.33 (m, 1H), 2.18 (d, 1H, J=7.2 Hz), 1.88 (m, 2H), 1.70 (m, 2H), 1.63 (s, 3H), 1.34 (s, 3H), 1.30 (s, 3H), 1.17 (s, 3H). $^{13}$C NMR (150 MHz, $CDCl_3$) δ 205.1, 150.6, 147.5, 130.1, 128.9 (2C), 128.4, 125.6 (2C), 120.4, 119.5, 101.1, 95.3, 72.4, 70.1, 68.7, 66.1, 62.0, 55.8, 54.4, 45.3, 40.8, 40.4, 33.9, 32.6, 30.4, 30.1, 29.7, 27.2, 25.4, 18.3.

Example 52

Synthesis of (3S, 4aR,5S,6aR,9S,11aS,11bS,14R,E)-5,14-Dihydroxy-2-(methoxymethylene)-4,4-dimethyl-8-methyleneoctahydro-1H-3,11b-(epoxymethano)-6a,9-methanocyclohepta[α]-naphthalene-1,6,7(2H,8H)-trione.

To a solution of 10 (5 mg, 0.011 mmol) in a mixture of MeOH (2 mL) and CH2Cl2 (0.5 mL) was added 5% HCl aqueous solution (0.2 mL) at room temperature. The resulting mixture was stirred at room temperature for 2 h. The reaction mixture was then diluted with water and extracted with dichloromethane. The extract was washed with saturated NaHCO3 (aqueous) solution and brine, dried over anhydrous Na2SO4, filtered, and evaporated to give an oily residue. The residue was purified using preparative TLC developed by EtOAc to afford the desired product 13 as a colorless amorphous gel (3.5 mg, 78%). [α]25 D-110 (c 0.10, CH2Cl2); HPLC purity 98.3% (tR=14.58 min); 1H NMR (300 MHz, CDCl3) δ 7.59 (s, 1H), 6.18 (s, 1H), 5.47 (s, 1H), 4.67 (m, 2H), 4.43 (d, 1H, J=0.9 Hz), 4.33 (s, 1H), 4.22 (m, 1H), 3.94 (s, 3H), 3.91 (m, 1H), 3.09 (m, 1H), 2.92 (m, 1H), 1.62 (m, 3H), 1.57 (m, 1H), 1.52 (s,3H), 0.99 (s, 3H); 13C NMR (75 MHz, CDCl3) δ 205.5, 201.4, 196.7, 156.3, 146.0, 118.6, 115.4, 75.1, 74.2, 71.7, 66.3, 62.1, 61.5, 51.7, 51.0, 45.3, 42.0, 38.2, 30.9, 28.5, 21.8, 20.1; HRMS calcd for C22H27O7, [M+H]+ 403.1751; found 403.1768.

Example 53

Synthesis of (3S,4aR,5S,6aR,9S,11aS,11bS,14R,Z)-5,14-Dihydroxy-2-(hydroxymethylene)-4,4-dimethyl-8-methyleneoctahydro-1H-3,11b -(epoxy methano)-6a,9-methanocyclohepta[α]-naphthalene-1,6, 7(2H, 8H)-trione.

To a solution of 10 (15 mg, 0.035 mmol) in THF (2 mL) was added 5% HCl (aqueous) solution (0.3 mL) at room temperature. The resulting mixture was stirred at room temperature for 4 h. The reaction mixture was then diluted with water and extracted with dichloromethane. The extract was washed with saturated NaHCO3 (aqueous) solution and brine, dried over anhydrous Na2SO4, filtered, and evaporated to give an oily residue. The residue was purified using preparative TLC developed by 5% methanol in dichloromethane to afford the desired product 14 as a pale pink amorphous gel (11 mg, 80%). [α]25 D-104 (c 0.1, CH2Cl2); HPLC purity 96.6% (tR=4.47 min); 1H NMR (300 MHz, CDCl3) δ 7.99 (br s, 1H), 7.13 (s, 1H), 6.26 (s, 1H), 5.49 (s, 1H), 4.61 (d, 1H, J=6.0 Hz), 4.54 (d, 1H, J=4.5 Hz), 4.47 (s, 1H), 3.83 (m, 4H), 3.11 (d, 1H, J=1.2 Hz), 3.05 (d, 1H, J=3.9 Hz), 1.89 (m, 1H), 1.75 (m, 2H), 1.57 (m, 2H), 1.48 (s, 3H), 0.96 (s, 3H); 13C NMR (75 MHz, CDCl3) δ 205.1, 200.4, 199.4, 160.1, 144.8, 120.3, 113.2, 71.6, 65.8, 60.9, 51.4, 50.6, 45.6, 41.2, 38.7, 31.1, 29.6 (2C), 22.5, 20.0. HRMS calcd for C21H25O7, [M+H]+ 389.1595; found 389.1591.

Example 54

Synthesis of Aziridine Derivatives of Oridonin

Scheme 1. Regio- and stereoselective aziridination on the oridonin skeleton.

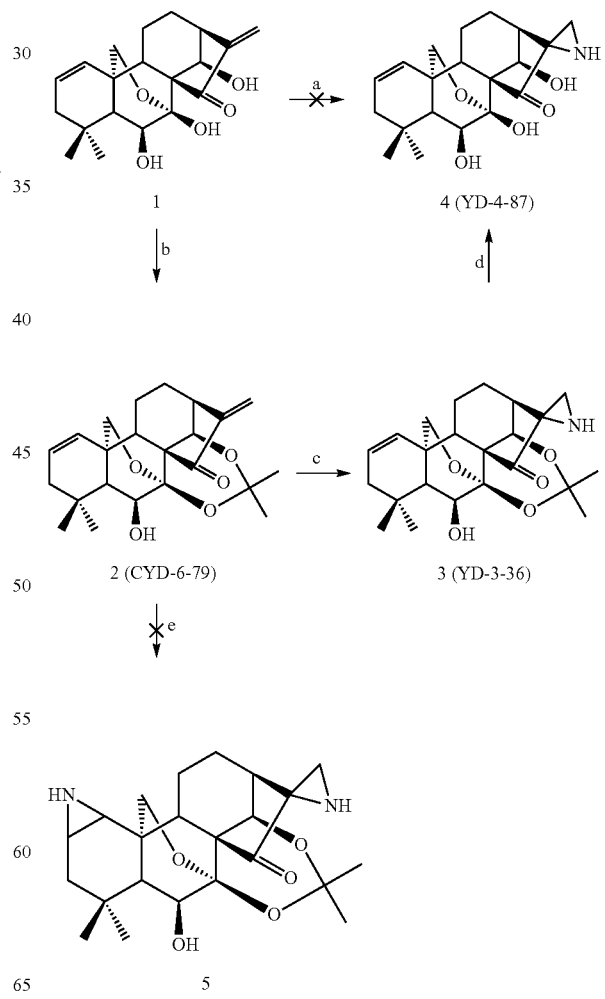

TABLE 5

Optimization of oridonin-based aziridination conditions

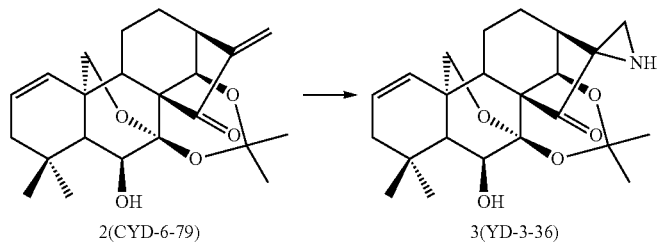

| Entries | Aminating agents/eqv. | Catalyst/ eqv. | Temp./ Time | Result |
|---|---|---|---|---|
| 1 | DPH/1.1 eqv. | $Rh_2(esp)_2$/ 5% mmol | r.t./24 h | CYD-6-79 (28%) YD-3-36 (54%) |
| 2 | DPH/2.2 eqv. | $Rh_2(esp)_2$/ 5% mmol | r.t./24 h | CYD-6-79 (trace) YD-3-36 (69%) |
| 3 | DPH/4.4 eqv. | $Rh_2(esp)_2$/ 5% mmol | r.t./24 h | CYD-6-79 (NA) YD-3-36 (71%) |
| 4 | DPH/4.4 eqv. | $Rh_2(esp)_2$/ 5% mmol | 50° C./24 h | CYD-6-79 (NA) YD-3-36 (66%) |
| 5 | DPH/4.4 eqv. | $Rh_2(esp)_2$/ 5% mmol | 50° C./>48 h | CYD-6-79 (NA) YD-3-36 (56%) |
| 6 | DPH/2.2 eqv. | $Rh_2(OAc)_4$/ 5% mmol | r.t./24 h | CYD-6-79 (trace) YD-3-36 (68%) |
| 7 | DPH/2.2 eqv. | $Rh_2(TPA)_4$/ 5% mmol | r.t./24 h | CYD-6-79 (predominance) YD-3-36 (trace) |
| 8 | DPH/2.2 eqv. | $Rh_2(R\text{-}DOSP)_4$/ 5% mmol | r.t./24 h | CYD-6-79 (predominance) YD-3-36 (NA) |
| 9 | DPH/2.2 eqv. | $Rh_2(S\text{-}DOSP)_4$/ 5% mmol | r.t./24 h | CYD-6-79 (predominance) YD-3-36 (NA) |

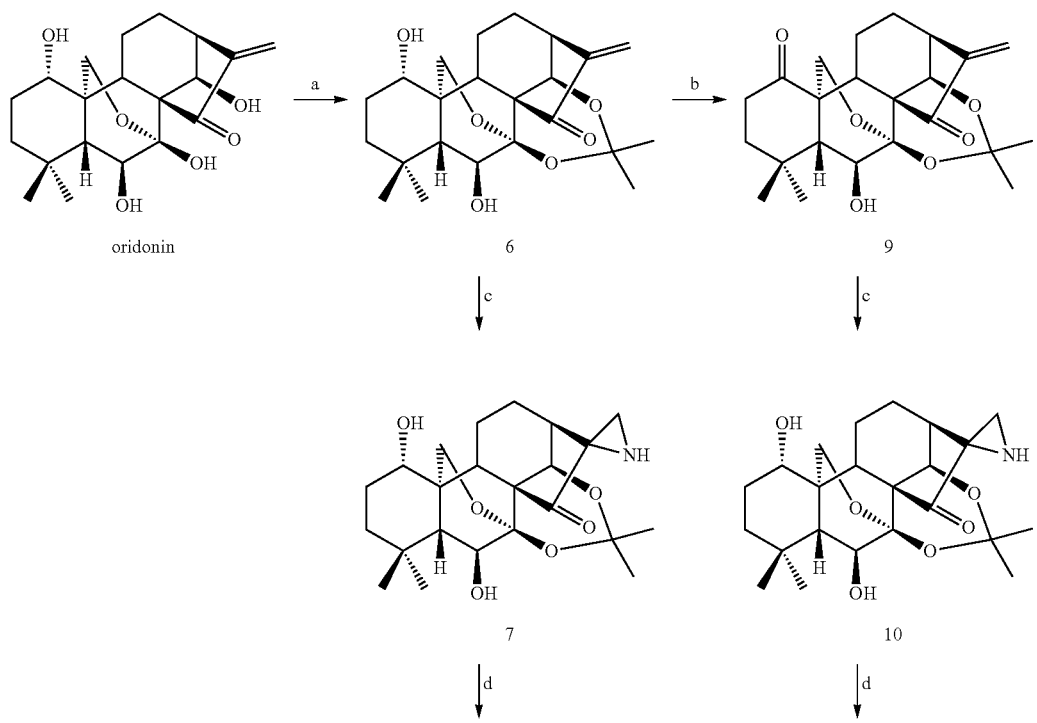

Scheme 2. Synthesis of aziridine analogues 7, 8, 10, and 11.

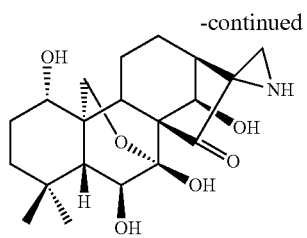

8

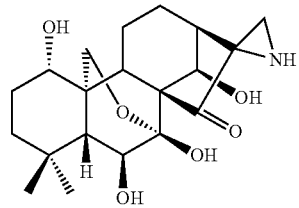

11

Reagents and conditions: (a) 2,2-dimethoxypropane, cat. p-TsOH, acetone, 1 h, rt, 90%; (b) Jones reagent, acetone, 2 hr, rt, 82%; (c) DPH, Rh$_2$(esp)$_2$, CF$_3$OH, rt, 12 h; (d) 5% HCl (aq). MeOH, CH$_2$Cl$_2$, 30 min, 89%.

Scheme 3. Synthesis of aziridine analogues 13 and 14.

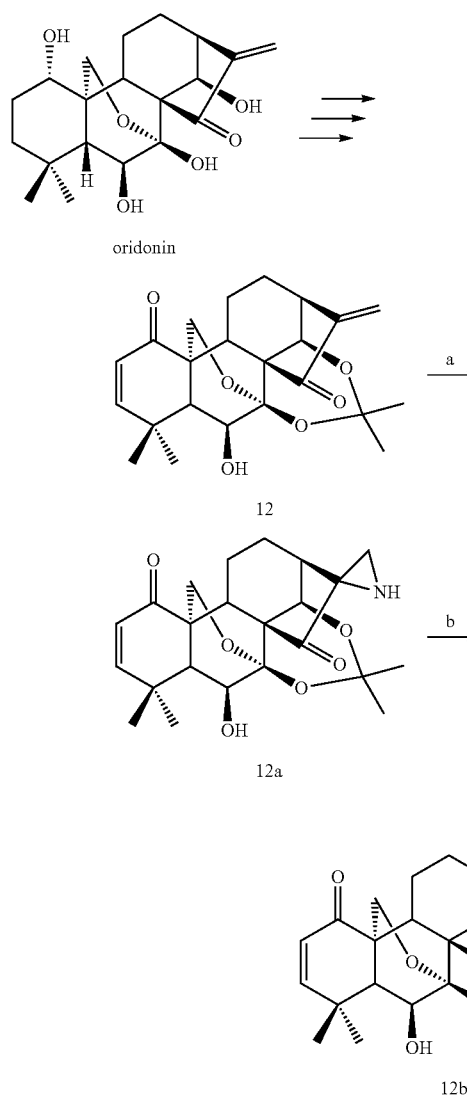

Reagents and conditions: (a) DPH, Rh$_2$(esp)$_2$, CF$_3$OH, rt, 12 h; (b) 5% HCl (aq), MeOH, CH$_2$Cl$_2$, 30 min, 89%.

Scheme 4. Synthesis of aziridine analogues 23-30.

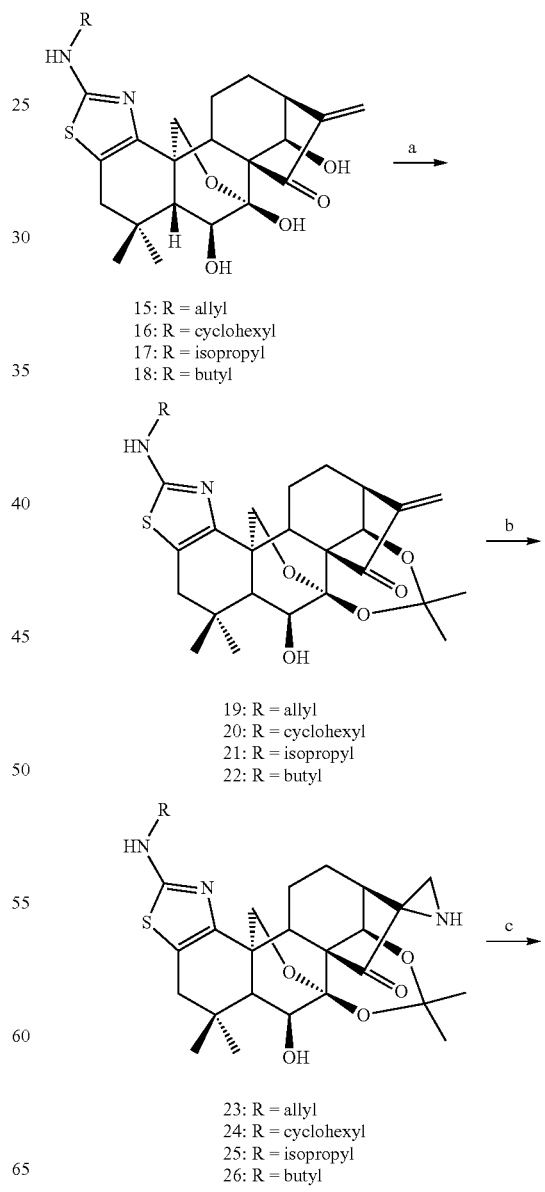

15: R = allyl
16: R = cyclohexyl
17: R = isopropyl
18: R = butyl

19: R = allyl
20: R = cyclohexyl
21: R = isopropyl
22: R = butyl

23: R = allyl
24: R = cyclohexyl
25: R = isopropyl
26: R = butyl

-continued

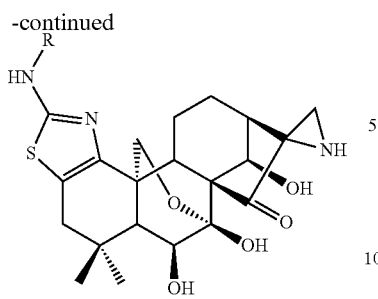

27: R = allyl
28: R = cyclohexyl
29: R = isopropyl
30: R = butyl

Reagents and conditions: (a) 2,2-dimethoxylpropane, cat. p-TsOH, acetone, 1 h, rt, 90%; (b) DPH, Rh$_2$(esp)$_2$, CF$_3$OH, rt, 12 h; %; (c) 5% HCl (aq), MeOH, CH$_2$Cl$_2$, 30 min, %.

The invention claimed is:

1. An oridonin derivative compound having the general formula of Formula Ia or a salt thereof:

Formula Ia

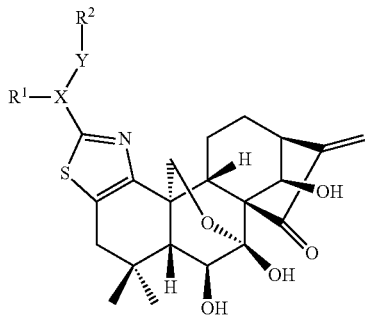

where X is CH, C or N;
Y is (CH)$_n$ and n is 0, 1, 2, 3, 4, or 5; and
R$^1$ and R$^2$ are independently hydrogen, oxo, nitro, halo, mercapto, cyano, azido, amino, imino, azo, —C(NH)(NH$_2$), sulfonyl, sulfinyl, sulfo, thioyl, methyl, ethyl, C2-C6 alkyl, C1-C6 alkoxy, C1-C6 hydroxyalkyl, C1-C6 carboxylate, C1-C6 carboxyl, C3-C5 alkenyl, C2-C4 carbonyl, C2-C4 aldehyde, C2-C8 heteroalkyl, C1-C6 alkylsulfonyl, C1C6 alkylhalide, substituted or unsubstituted 3 to 8 membered cycloalkyl, substituted or unsubstituted 3 to 8 membered heterocycle, substituted or unsubstituted aryl, substituted or unsubstituted heteroaryl, wherein R$^1$and R$^2$ can form a substituted or unsubstituted 5 to 9 membered heterocyle or cycloalkyl.

2. The compound of claim 1, wherein X is N, R$^1$ is hydrogen, and n is 0.

3. The compound of claim 2, wherein R$^2$ is C1-C4 alkyl, C2-C4aldehyde, or C3-C7 cycloalkyl.

4. The compound of claim 1, wherein the compound is (6S,7S,7aR,10R,12bR,15R)-6,7,15-trihydroxy-2,5,5-trimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-19);

(5aR,6S,7S,7aR,10S,12aS,12bR,15R)-2-amino-6,7,15-trihydroxy-5,5-dimethyl-9- methylene-5,5a,6,7,10,11,12,12a-octahydro-4H-7,12b-(epoxymethano)-7a,10-methanocyclohepta[7,8]naphtho[1,2-d]thiazol-8(9H)-one(CYD-5-41);

(5aR,6S,7S,7aR,10S,12aS,12bR,15R)-6,7,15-trihydroxy-5,5-dimethyl-2-(methylamino)-9-methylene-5,5a,6,7,10,11,12,12a-octahydro-4H-7,12b-(epoxymethano)-7a,10-methanocyclohepta[7, 8]naphtho[1,2-d]thiazol-8(9H)-one (CYD-5-54);

(6S,7S,7aR, 10R,12bR,15R)-2-(cyclohexylamino)-6,7,15-trihydroxy-5,5-dimethyl-9-methylene-5,5a,6,7,10,11,12,12a-octahydro-4H-7,12b-(epoxymethano)-7a,10-methanocyclohepta[7, 8]naphtho[1,2-d]thiazol-8(9H)-one (CYD-6-17-2);

(5aR,6S,7S,7aR,10S,12aS,12bR,15R)-2-(allylamino)-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CTD-6-18);

(6S,7S,7aR, 10R,12bR,15R)-6,7,15-trihydroxy-5,5-dimethyl-9-methylene-2-((2-(piperidin-1-yl)ethyl)amino)-5,5a,6,7,10,11,12,12a-octahydro-4H-7,12b(epoxymethano)-7a,10-methanocyclohepta[7, 8]naphtho[1,2-d]thiazol-8(9H)-one (CYD-6-21);

N-((6S,7S,7aR,10R,12bR,15R)-6,7,15-trihydroxy-5,5-dimethyl-9-methylene-8-oxo-5,5a,6,7,8,9,10,11,12,12a-decahydro-4H-7,12b-(epoxymethano)-7a,10-methanocyclohepta[7,8]naphtho[1,2-d]thiazol-2-yl)acetamide (CYD-6-21);

(6S,7S,7aR,10R,12bR,15R)-2-(azepan-1-yl)-6,7,15-trihydroxy-5,5-dimethyl-9-methylene-5,5a,6,7,10,11,12,12a-octahydro-4H-7,12b-(epoxymethano)-7a,10-methanocyclohepta[7, 8]naphtho[1,2-d]thiazol-8(9H)-one (CYD-6-26-2);

(5aR,6S,7S,7aR,10S,12aS,12bR,15R)-2-(butylamino)-6,7,15-trihydroxy-5,5-dimethyl-9-methylene-5,5a,6,7,10,11,12,12a-octahydro-4H-7,12b-(epoxymethano)-7a,10-methanocyclohepta[7, 8]naphtho[1,2-d]thiazol-8(9H)-one (CYD-6-28);

1-((5aR,6S,7S,7aR,10S,12aS,12bR,15R)-6,7,15-trihydroxy-5,5-dimethyl-9-methylene-8-oxo-5,5a,6,7,8,9,10,11,12,12a-decahydro-4H-7,12b-(epoxymethano)-7a,10-methanocyclohepta[7, 8]naphtho[1,2-d]thiazol-2-yl)guanidine (CYD-6-29); or (5aR,6S,7S,7aR,10S,12aS,12bR,15R)-6,7,15-trihydroxy-2-(isopropylamino)-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-30).

5. The compound of claim 1, wherein the compound is (6S,7S,7aR,10R,12bR,15R)-2-(cyclohexylamino)-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-17-2).

6. The compound of claim 1, wherein the compound is (5aR,6S,7S,7aR,10S,12aS,12bR,15R)-2-(allylamino)-6,7,15-trihydroxy-5,5-dimethyl-9-methylene-5,5a,6,7,10,11,12,12a-octahydro-4H-7,12b-(epoxymethano)-7a,10-methanocyclohepta[7,8]naphtho[1,2-d]thiazol-8(9H)-one (CYD-6-18).

7. The compound of claim 1, wherein the compound is (5aR,6S,7S,7aR,10S,12aS,12bR,15R)-2-(butylamino)-6,7, 15-trihydroxy-5,5-dimethyl-9-methylene-5,5a,6,7,10,11,12,12a-octahydro-4H-7,12b-(epoxymethano)-7a,10-methano-cyclohepta[7,8]naphtho[1,2-d]thiazol-8(9H)-one (CYD-6-28).

8. A method of treating cancer comprising administering an effective amount of a compound of claim 1 to patient in need thereof.

* * * * *